US011826081B2

(12) United States Patent
Lowry et al.

(10) Patent No.: US 11,826,081 B2
(45) Date of Patent: *Nov. 28, 2023

(54) IMPLANTABLE VERTEBRAL FRAME SYSTEMS AND RELATED METHODS FOR SPINAL REPAIR

(71) Applicant: GLOBUS MEDICAL, INC., Audubon, PA (US)

(72) Inventors: David Lowry, Holland, MI (US); Desmond O'Farrell, Grand Rapids, MI (US); Scott Tuinstra, Holland, MI (US); Roger Veldman, Hudsonville, MI (US)

(73) Assignee: Globus Medical, Inc., Audubon, PA (US)

( * ) Notice: Subject to any disclaimer, the term of this patent is extended or adjusted under 35 U.S.C. 154(b) by 7 days.

This patent is subject to a terminal disclaimer.

(21) Appl. No.: 17/839,533

(22) Filed: Jun. 14, 2022

(65) Prior Publication Data
US 2022/0304729 A1    Sep. 29, 2022

Related U.S. Application Data

(60) Continuation of application No. 16/720,330, filed on Dec. 19, 2019, now Pat. No. 11,389,210, which is a
(Continued)

(51) Int. Cl.
A61B 17/70     (2006.01)
A61B 17/80     (2006.01)
(Continued)

(52) U.S. Cl.
CPC ...... *A61B 17/7059* (2013.01); *A61B 17/1671* (2013.01); *A61B 17/1757* (2013.01);
(Continued)

(58) Field of Classification Search
CPC ............ A61B 17/7059; A61B 17/8004; A61B 17/8019; A61B 17/8042; A61B 17/8033;
(Continued)

(56) References Cited

U.S. PATENT DOCUMENTS 6,663,637 B2 * 12/2003 Dixon .................. A61B 17/025
606/86 R
7,153,304 B2 * 12/2006 Robie ................ A61B 17/1757
606/90
(Continued)

*Primary Examiner* — Tracy L Kamikawa

(57) ABSTRACT

A system for performing surgical repair of the spine includes a distractor and a permanently implanted bone plate system. A surgical repair methodology is also disclosed that employs an implanted bone plate system with a substantially void internal volume which is attached to adjacent vertebrae subsequent to the distraction and adjustment of curvature of the vertebrae and prior to the excision of disc and/or end plate tissue through the bone plate. The device further facilitates the subsequent delivery of an interbody repair device for the purpose of either fusion or dynamic stabilization, such as by disc arthroplasty. The plate may be permanently implanted, such as when a fusion between the attached vertebral bodies is desired, but it need not be permanently implanted.

11 Claims, 56 Drawing Sheets

Related U.S. Application Data continuation of application No. 14/265,166, filed on Apr. 29, 2014, now Pat. No. 10,548,645, which is a division of application No. 12/616,762, filed on Nov. 11, 2009, now Pat. No. 8,709,054.

(51) Int. Cl.

| | | |
|---|---|---|
| *A61F 2/44* | (2006.01) | |
| *A61F 2/46* | (2006.01) | |
| *A61B 17/17* | (2006.01) | |
| *A61B 17/86* | (2006.01) | |
| *A61B 17/16* | (2006.01) | |
| *A61B 90/94* | (2016.01) | |
| *A61B 17/88* | (2006.01) | |
| *A61F 2/30* | (2006.01) | |
| *A61B 17/02* | (2006.01) | |

(52) U.S. Cl.
CPC ........ *A61B 17/808* (2013.01); *A61B 17/8028* (2013.01); *A61B 17/8042* (2013.01); *A61B 17/8605* (2013.01); *A61B 17/885* (2013.01); *A61B 90/94* (2016.02); *A61F 2/4455* (2013.01); *A61B 17/1728* (2013.01); *A61B 2017/0256* (2013.01); *A61F 2/4611* (2013.01); *A61F 2002/30121* (2013.01); *A61F 2002/30123* (2013.01); *A61F 2002/30578* (2013.01)

(58) Field of Classification Search
CPC ........... A61B 17/885; A61B 2017/0256; A61F 2/4455; A61F 2/46; A61F 2/4611; A61F 2002/4615
See application file for complete search history.

(56) References Cited

U.S. PATENT DOCUMENTS

| | | | |
|---|---|---|---|
| 10,548,645 B2* | 2/2020 | Lowry | ................. A61B 17/885 |
| 2007/0123884 A1* | 5/2007 | Abdou | ............... A61B 17/7059 |
| | | | 606/279 |
| 2010/0152781 A1* | 6/2010 | Nehls | ................. A61B 17/7074 |
| | | | 606/301 |

* cited by examiner

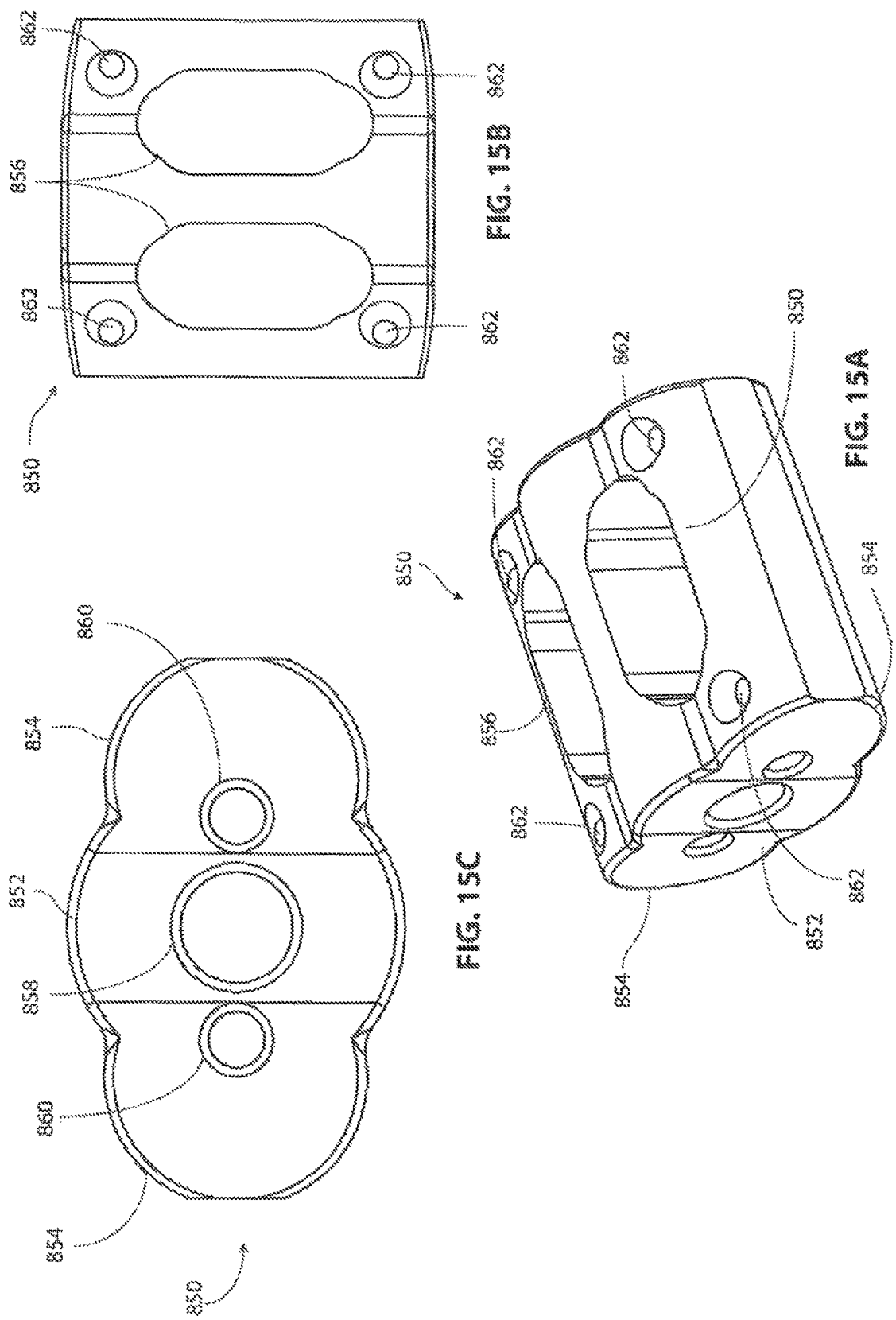

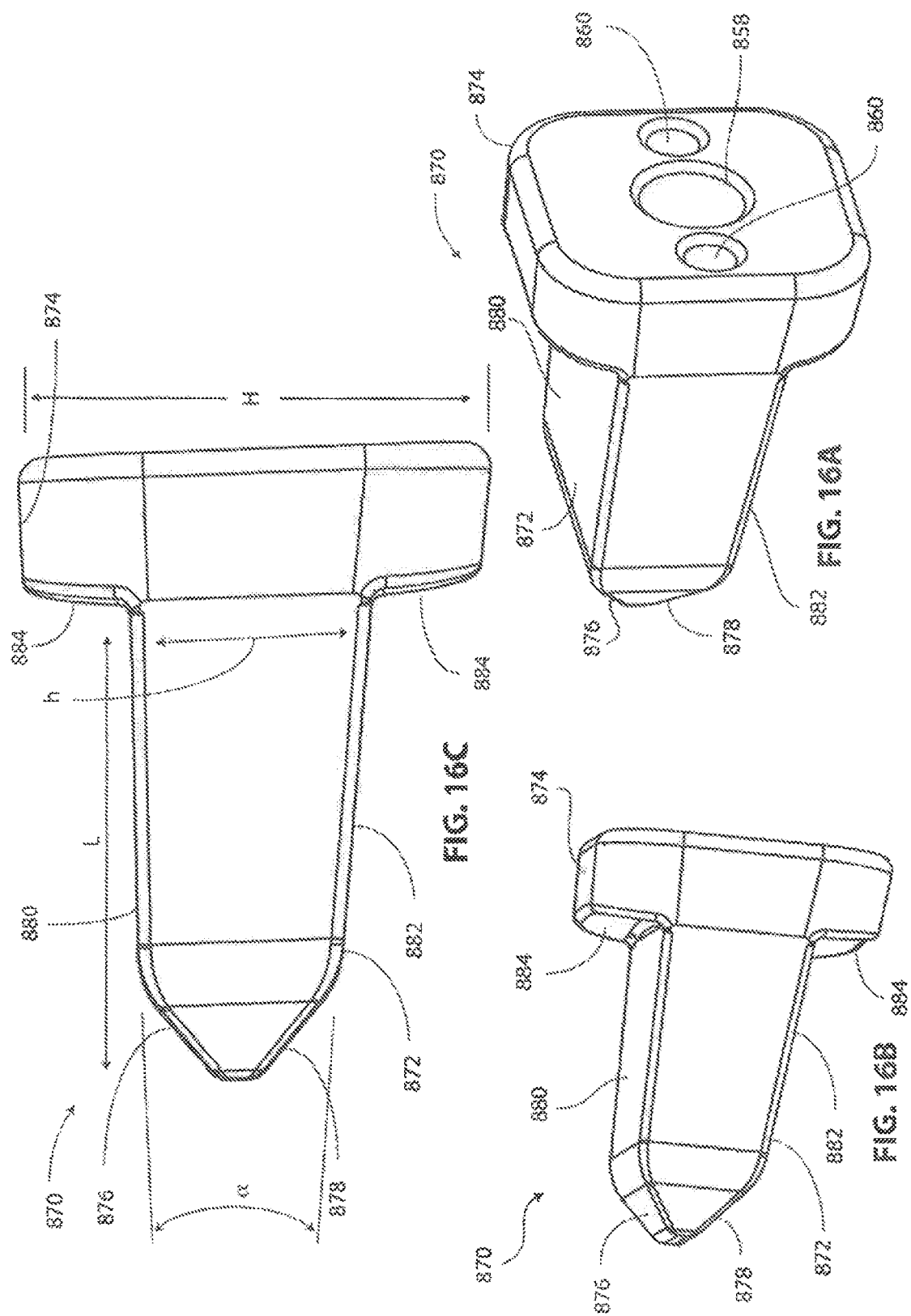

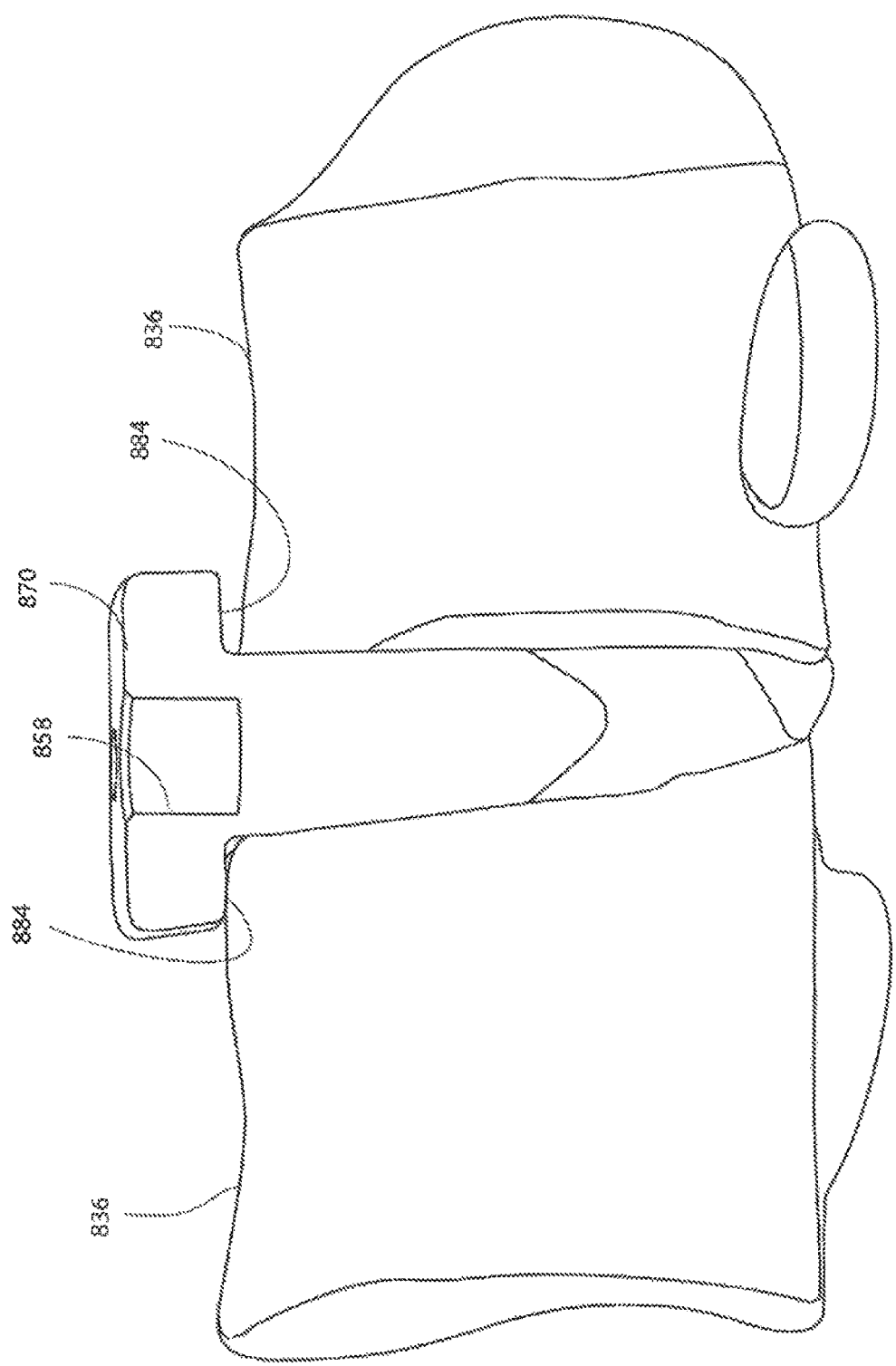

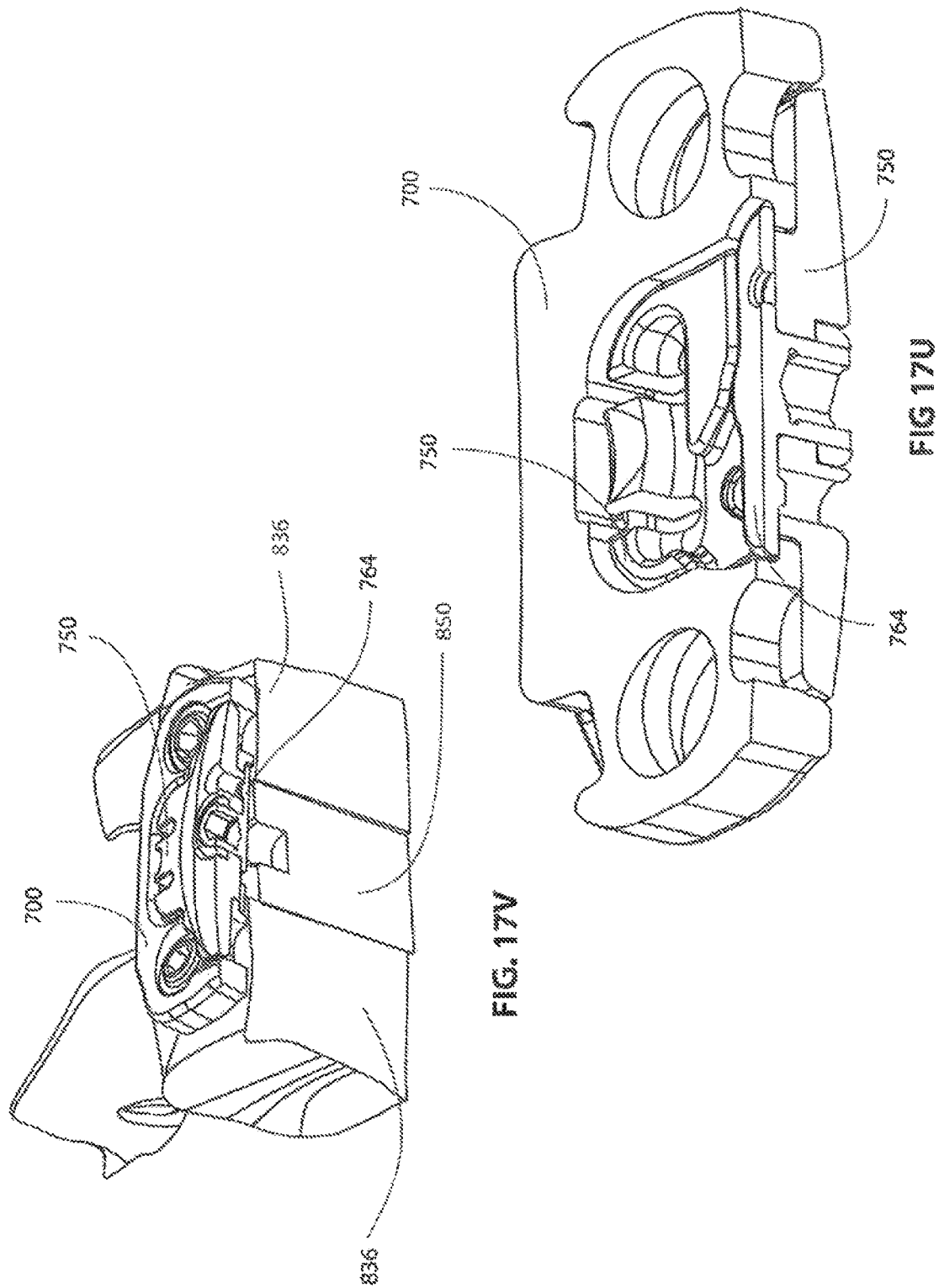

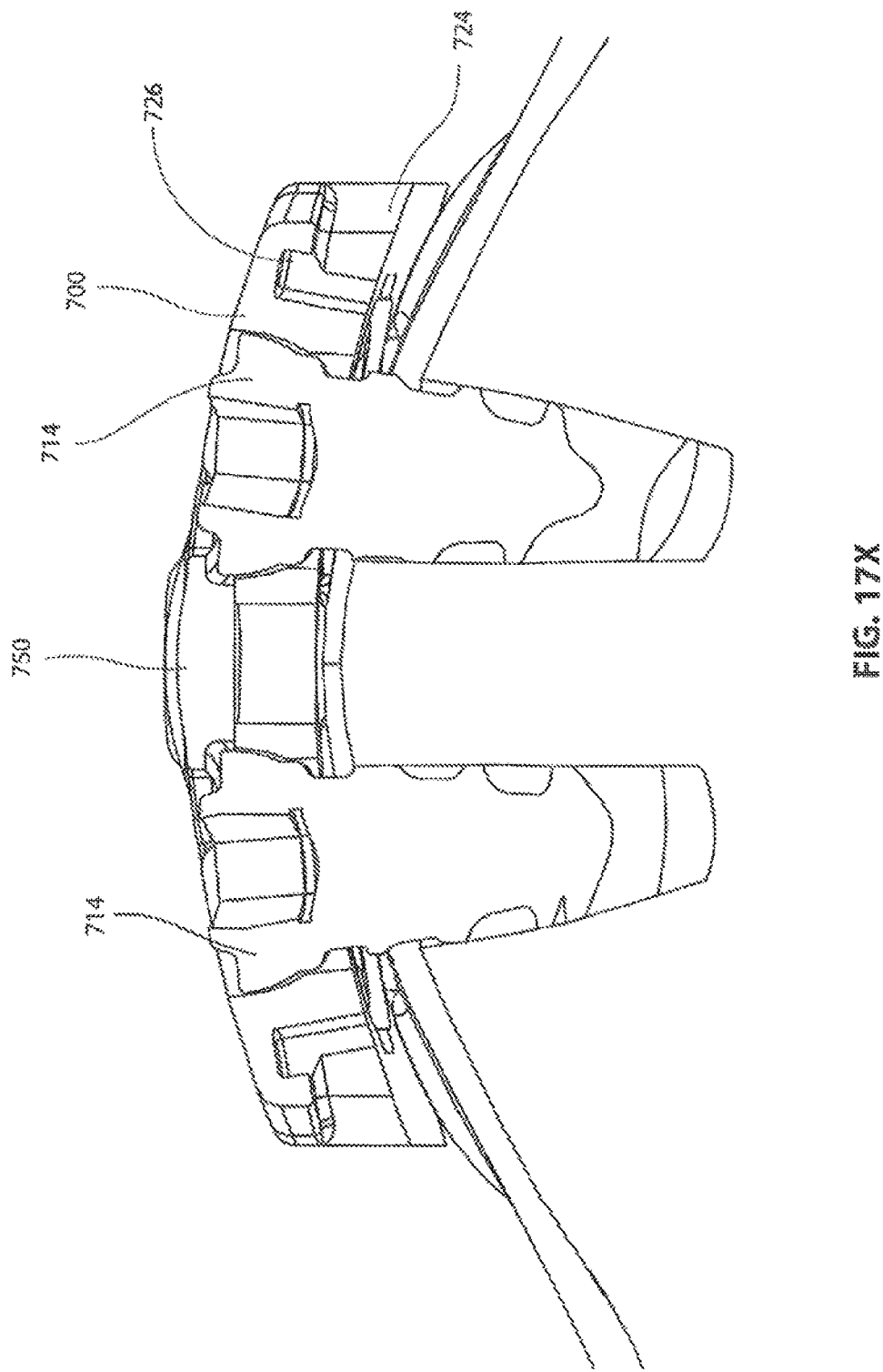

IMPLANTABLE VERTEBRAL FRAME SYSTEMS AND RELATED METHODS FOR SPINAL REPAIR

CROSS-REFERENCE TO RELATED APPLICATIONS

This application is a continuation of U.S. patent application Ser. No. 16/720,330, filed on Dec. 19, 2019, now U.S. Pat. No. 11,389,210, which is a continuation of U.S. patent application Ser. No. 14/265,166 filed on Apr. 29, 2014, now U.S. Pat. No. 10,548,645, which is a divisional application of U.S. application Ser. No. 12/616,762 filed Nov. 11, 2009, now U.S. Pat. No. 8,709,054. Each patent application is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The present invention relates to a system for performing surgical repair of the spine, such as for but not limited to the delivery of an interbody repair device for the purpose of either fusion or dynamic stabilization. It is current practice in spinal surgery to use bone fixation devices to improve the mechanical stability of the spinal column and to promote the proper healing of injured, damaged or diseased spinal structures. Typically, corrective surgery entails the removal of damaged or diseased tissue, a decompression of one or more neural elements, followed by the insertion of an intervertebral implant for the purposes of a fusion or disc arthroplasty. In cases where spinal fusion is the desired surgical outcome, the final step is often to apply a bone plate in order to immobilize adjacent vertebral bones to expedite osteogenesis across said vertebral segments.

Most current surgical techniques require that damaged vertebral tissue be placed under rigid axial distraction throughout much of the procedure. This allows for greater ease in the removal of tissue, provides a larger working space for instrument maneuverability, enhances the surgeon's visibility and assists with the fit of the interbody implant once the distractor apparatus is removed. Conventional distraction of the spine typically employs the use of temporary "distractor pins" placed directly into the bone tissue adjacent to the disc space to be repaired, which are subsequently induced to move axially by the attachment and adjustment of a secondary tool. An alternative method employs the use of a ratcheting spreader device which is inserted directly into the vertebral interspace and is adjusted thereafter to achieve desired distraction. These distraction methods offer an imprecise means to restore preferred vertebral alignment, add several steps, require more time to install and remove, increase the risk for entwining of surrounding vascular structures or peripheral nerves and can present significant physical impediments and technical challenges to the surgeon. Additionally, because the distractor device remains temporarily inserted during the decompression and fusion portions of the procedure, the surgeon must essentially work around the obtrusive projecting devices while completing the majority of the surgery.

It is also known that current distraction methods, while generally not designed or intended for this purpose, are often employed to adjust or maintain the angular alignment of adjacent vertebra in an attempt to restore normal lordotic curvature. The outcomes are varied, the degree of distraction and the angular correction produced by current distraction methods are often imprecise, require substantial subjective assessment by the surgeon and can vary significantly from patient to patient. Further, excessive distraction can result in a negative surgical outcome which can result in nerve damage or on-going post surgical pain for the patient.

There is a high degree of dimensional variability in the resulting intervertebral volume after distraction has been achieved using these devices. As a result, the surgeon must often make "trial and error" assessments as to the size and shape of the interbody implant to be inserted and may be required to customize the implant intraoperatively prior to final insertion.

In the conventional method, once the implant has been inserted, the distractor device is removed and the vertebrae can be secured by the attachment of a bone plate. Such bone plates, including a plurality of bone screws, are applied near the completion of the procedure to provide vertebral fixation and prohibit undesirable migration of the intervertebral implant.

Several design constructs have already been proposed in which a device is applied to adjacent vertebrae at the start of a procedure, prior to tissue removal, for the purposes of achieving and maintaining preferred vertebral alignment while serving also to constrain tissue removal throughout the procedure. The disclosed or published art in this method can generally be categorized into two broad categories: removable devices and permanently implantable devices.

The removable devices differ from the present proposed invention in that the devices used to maintain preferred vertebral alignment are temporary inserts and are subsequently removed after tissue removal so that a repair device may be delivered thereafter. The prior art which discloses permanently implantable devices differs in that the devices function solely to maintain preferred vertebral alignment and are not part of a comprehensive system and related method to precisely control and permanently maintain the preferred spatial relationship of adjacent vertebral members for controlled tissue removal and delivery of a repair device.

Removable Devices

U.S. Pat. No. 7,153,304 entitled Instrument System for Preparing a Disc Space Between Adjacent Vertebral Bodies to Receive a Repair Device, issued Dec. 26, 2006 to Roble et al., discloses a removable instrument system for preparing a disc space between adjacent vertebral bodies using a series of distracters that restore natural lordosis before a temporary template is attached for vertebral immobilization and to function as a guide for an insertable reamer meant for tissue removal.

U.S. Pat. No. 7,083,623 to Michelson, entitled Milling instrumentation and Method for Preparing a Space Between Adjacent Vertebral Bodies, issued Aug. 1, 2006, discloses a removable milling device and method for preparing a space between adjacent vertebral bodies which essentially maintains preferred vertebral alignment while functioning as a saw guide to control hone and soft tissue removal.

US Pat. App. 2005/0043740 to Haid, entitled Technique and Instrumentation for Preparation of Vertebral Members, published Feb. 24, 2005, discloses a removable instrumentation set and technique for preparation of vertebral members utilizing a docking ring which is temporarily applied to the anterior spine to maintain preferred vertebral alignment and to function as a docking plate for an articulating bone removal device.

U.S. Pat. No. 7,033,362 to McGahan, entitled Instruments and Techniques for Disc Space Preparation, issued Apr. 25, 2006, discloses a removable instrumentation set and method for disc space preparation whereby an intervertebral device is temporarily inserted for the purpose of constraining tissue removal and guiding the position of an intervertebral repair device.

US Pat. App. 2003/0236526 to Van Hoeck, entitled Adjustable Surgical Guide and Method of Treating Vertebral Members, published Dec. 25, 2003, discloses a removable surgical guide and method with adjustable functionality for the preparation of adjacent vertebra.

US Pat. App. No. 2006/0247654 to Berry, entitled Instruments and Techniques for Spinal Disc Space Preparation, published Nov. 2, 2006, discloses a removable milling instrument assembly for vertebral endplate preparation which constrains a cutting path obliquely oriented to the axis of the vertebra.

Permanently Implanted Devices

US Pat. App. 2004/0097925 to Boehm, entitled Cervical Spine Stabilizing System and Method, published May 20, 2004, discloses a permanently implantable spine stabilizing system and method whereby a plate configured to be positively centered along the midline is placed to retain adjacent vertebra in a desired spatial relationship during discectomy and fusion procedures. The disclosed invention uses a series of temporary implants and removable drill templates in an attempt to assure the alignment of the implanted device along the midline of the spinal column. This alignment is typically not considered to be significant in determined the clinical outcome of the procedure and is further considered impractical for the purposes of performing repair procedures on multiple adjacent disk spaces due to the normal scoliotic curvature of the spine.

US Pat. App. 2005/0149026 to Butler et al., entitled Static and Dynamic Cervical Plate Constructs, published Jul. 7, 2005, describes an implanted cervical bone plate having a graft window located between the bone screw holes for the purposes of providing visualization and access to an intervertebral implant. The device described is applied after the intervertebral space has been repaired and after the implant has been positioned. The specification states specifically, that an appropriately "sized dynamic plate is placed over the inserted bone implant"; thereafter the bone plate is located with respect to the implant by viewing the implant through the graft window and secured in place using bone screws.

Additional bone plate devices are disclosed in U.S. Pat. No. 3,741,205 to Markolf et al, and US Pat. Apps. 2005/0149026 to Butler et al. and 2007/0233107 to Zielinski.

Accordingly, it is apparent that there remains a need for and advantage to a permanently implantable spinal repair system and related method whereby the final preferred vertebral alignment and fixation occurs prior to the surgical removal of damaged tissue, without the use of temporary implants or fasteners and where the surgical procedures can be performed there-through in the minimum amount of time with the minimum number of entries into the surgical field. It is further apparent that there is a need for a system wherein subsequent recovery procedures can be performed with minimal effort should implantation fail or should subsequent surgery be required.

SUMMARY OF THE DISCLOSURE

The invention relates generally to systems and methods for establishing and securing adjacent vertebrae in a defined spacial relationship prior to the excision and repair of damaged tissue. In one embodiment, the system includes at least one distraction device, at least one implantable vertebral frame, at least one interbody repair implant, and at least one retention member. In this embodiment, the distraction device is configured for temporary placement between adjacent vertebrae for achieving a desired spatial relationship between the vertebrae. In this embodiment, the implantable vertebral frame is configured to span between the adjacent vertebrae, the frame being configured to attach to each of the adjacent vertebra while the distraction device is in place to postoperatively maintain the desired spatial relationship between the vertebrae after the distraction device is removed, the frame also having at least one internal operating aperture there-through for providing access to at least one intervertebral disk space. In this embodiment, the interbody repair implant is sized in relationship to the aperture of the frame to fit these-through and into the intervertebral space. And finally, in this embodiment, the retention member is attachable to the frame to cover at least a portion of the aperture.

In various embodiments of the above summarized system, the frame may assume various forms and include various features that will now be summarized. In some embodiments of the system, the frame may be configured to span between and remain postoperatively attached to at least three adjacent vertebrae. In some embodiments of the system, the frame may include external walls having integrally manufactured retractor blade engaging features. In some embodiments of the system, the frame may have a plurality of through holes to facilitate attachment of the frame to adjacent vertebrae by means of bone screws. In some of these particular embodiments, the holes may be a combination of elongated slots and circular holes to accommodate the insertion of bone screws there-through into vertebral bone tissue. In some embodiments of the system, the frame may have a plurality of protrusions to facilitate attachment of the frame to the adjacent vertebrae by means of impingement into the bone tissue of the adjacent vertebrae.

Further, in some embodiments of the system, the frame may have one or more receiving elements to accept a locking member for securing the retention member. In various of these particular embodiments, the locking member may be any of a threaded screw device, a snap lock device, or a cam lock device, and further in some of these particular embodiments, the one or more receiving elements for the retention member may accommodate the temporary location of at least one tissue retractor pin.

Still further, in some embodiments of the system, the frame may be configured to receive bone screws there-through to attach the frame to the vertebrae, the retention member being adapted to cover the bone screws when the member is attached to the frame to prevent back-out of the screws.

In some embodiments of the system, the retention member may be configured to retain the interbody implant in its surgically established position.

According to an aspect of the invention, a vertebral implant may be provided. Embodiments of the implant are configured to rigidly interconnect at least two vertebrae, the implant being manufactured from a generally rigid material having thereon contact surfaces for engaging on vertebral bone material, the contact surfaces including a biocompatible, compressible, polymeric material. In some of these embodiments, the generally rigid material may also include a biocompatible metallic material.

In another aspect of the invention, various embodiments of methods are provided for applying the system and/or the vertebral implant, as summarized above. In one method of applying the system, the adjacent vertebrae are distracted and spacially oriented with the distraction device, the vertebral frame is secured to the adjacent vertebrae, the damaged tissue is excised through the operating aperture in the vertebral frame, the vertebral interspace is prepared to receive the repair implant, said implant being placed through the operating aperture into said prepared interspace, and the retention member is then installed onto the vertebral frame.

Another embodiment of a method for applying the system is also provided. In this embodiment, the vertebral frame is attached to one or more vertebrae, the vertebrae are then distracted and spacially oriented by operating through the operating aperture in the vertebral frame, the vertebral frame is secured to each adjacent vertebrae, the damaged tissue is excised through the operating aperture in the vertebral frame, the vertebral interspace is prepared through the operating aperture to receive the repair implant, the interbody implant is inserted through the operating aperture into the prepared interspace and the retention member is installed onto the vertebral frame.

In another aspect of the invention, a method for treating a portion of a spinal column is provided. The method includes distracting and spatially orienting adjacent vertebral bodies of the spinal column, securing a vertebral frame to the adjacent vertebral bodies, the vertebral frame having at least one operating aperture there-through, preparing a vertebral interspace to receive an interbody implant, inserting the interbody implant through the operating aperture and into the prepared interspace, and maintaining the vertebral frame in place on the vertebral bodies postoperatively.

In some embodiments of this method for treating a portion of a spinal column, the distracting step is performed using a distraction device placed between the vertebral bodies, and the distraction device is removed from between the vertebral bodies through the operating aperture in the vertebral frame after the vertebral frame is secured to the vertebral bodies. In some of these methods for treating a portion of the spinal column, the method may further include the step of excising damaged tissue through the operating aperture in the vertebral frame. In another embodiment, the method may further include the step of installing a retention member onto the vertebral frame after inserting the interbody implant. In still other embodiments, the step of preparing a vertebral interspace to receive an interbody implant may be performed through the operating aperture of the vertebral frame.

In some embodiments of the method for treating a portion of the spinal column, the vertebral frame may have particular features or aspects. Thus, in some embodiments, the vertebral frame may be attached to at least one of the vertebral bodies before the distraction step, the distraction step being performed through the operating aperture in the vertebral frame. In other embodiments, the vertebral frame may be secured to more than two adjacent vertebral bodies. In still other embodiments, the vertebral frame may be maintained in place permanently, generally from the time it is first secured to the vertebral bodies.

According to some aspects of the present invention, a means and method to precisely control and permanently maintain the preferred spatial relationship of adjacent vertebral members prior to the surgical removal of damaged tissue may be provided.

According to some aspects of the invention, a means may be provided whereby preferred spatial relationship of adjacent vertebra can be achieved and permanently maintained using conventional vertebral distraction methods or in conjunction with a novel intervertebral distractor apparatus disclosed separately in the co-pending patent application Ser. No. 60/954,507 titled "Device and Method for Variably Adjusting Intervertebral Distraction and Lordosis" filed on Aug. 7, 2007.

According to some aspects of the invention, the surgical removal of damaged tissue may be constrained in order to minimize the risk of damage to the adjacent tissue.

According to some aspects of the invention, the preferred spatial relationship of adjacent vertebral members may be precisely controlled and permanently maintained with a device having a low profile, allowing the surgeon to work in an unrestricted manner, within, around, above and below the device.

According to some aspects of the invention, the preferred spatial relationship of adjacent vertebral members may be precisely controlled and permanently maintained for the insertion of a spinal repair device.

According to some aspects of the invention, the insertion of a spinal repair device may be spatially controlled.

According to some aspects of the invention, a locking member may be accommodated to prevent undesirable migration of the spinal repair device and bone screws.

According to some aspects of the invention, the method and device may be utilized across one or multiple vertebral segments.

According to some aspects of the invention, a permanent rigid internal fixation may be provided across one or multiple vertebral segments.

In one particular embodiment, a permanent semi-rigid fixation is provided across one or multiple vertebral segments.

In one particular embodiment, a retractor apparatus is accommodated by providing integrally manufactured receiving and engaging means for the tissue control blades of said retractor.

In one particular embodiment, removable templates which locate and constrain the surgical removal of tissue to the desired vertebral area are accommodated.

In one particular embodiment the vertebral fixation element in the system is manufactured using two biocompatible materials, the structural component being manufactured from a high modulus rigid material such as Titanium, Stainless steel or other metal and having therein contact elements for engaging on the vertebral tissue, said contact pads being manufactured from a bio-compatible compliant material such as polyethylene or a silicone. These contact pads are intended to be plastically deformed under compressive loads and to be compressed and deformed by the insertion of the bone screws in order to act as damping elements to absorb vibration during bone tissue removal and consequently to minimize the risk of associated screw dislocation. These pads further increase the initial friction between the vertebral fixing element and the vertebrae thereby reducing premature dynamic compression of the distracted vertebrae. Finally, the compliant elements act as shock absorbers during patient healing and promote osteogenesis within the implanted repair device.

In one particular embodiment, the inventive device may be coupled with a stereotactic navigational system for preferred device positioning and to constrain the surgical removal of tissue.

According to aspects of the invention, a system and surgical method for use in surgical spinal repair or reconstruction procedures are described herein, whereby preferred and final vertebral axial and angular positioning and fixation occurs prior to the cutting and removal of the tissue.

In one embodiment, the system can generally be described as a combination of:

1) An intervertebral distraction device placed temporarily between adjacent vertebrae for purposes of achieving a desired spatial relationship between adjacent vertebrae.

2) A vertebral plate.

3) A locking and retention member engaging with said vertebral plate.

4) An implantable interbody repair device.

5) Bone screws.

6) The vertebral plate having through holes for the purposes of accommodating attachment to the vertebrae using the bone screws.

7) Said vertebral plate having a generally open interior volume through which the removal of damaged tissue is performed.

8) Said vertebral plate having a generally open interior volume which constrains the insertion and prevents migration of an intervertebral repair device.

9 Said vertebral plate having accommodation means for attaching the locking and retention member for retention of the implanted repair device and the bone screws.

10) One embodiment of the surgical method may be generally described as the sequence of spacially orienting adjacent vertebrae, locking said vertebrae in their prescribed relative positions using the vertebral plate and bone screws, preparing and repairing the intervertebral space through the operating window in the installed vertebral plate and securing the implant in place by securing a locking member to the vertebral plate.

1) An alternate surgical method may be generally described as the sequence of attaching the vertebral plate to one of the adjacent vertebrae, spatially orienting the adjacent vertebrae through the operating window in the vertebral plate, locking said vertebrae in their prescribed relative positions using the vertebral plate and bone screws, preparing and repairing the intervertebral space through the operating window in the installed vertebral plate and securing the implant in place by securing a locking member to the vertebral plate.

2) In an alternate surgical method, the vertebrae are partially distracted and held in this position by the insertion of bone screws through slots in the vertebral plate. In this instance the final distraction is achieved by the forcible insertion of an interbody repair device which has a craniocaudal dimension that is larger than the dimension of the receiving intervertebral space. The differences in the two dimensions results in a further, final distraction of the adjacent vertebrae. This final movement of the vertebrae is accommodated by the movement of the screws within the slots in the vertebral plate.

In an anticipated procedure a conventional intervertebral distractor apparatus is manually inserted into or between the vertebrae resulting in axial distraction of the vertebrae. In the case of a standard wedge style distractor the degree of distraction results from a combination of the included angle and the depth to which it is inserted between the vertebrae. In the case of a distractor pin system the distraction results from the manipulation of a secondarily applied axial adjustment device.

In a further embodiment the included angle of the distractor device is variably adjustable by the surgeon after insertion between the vertebrae, this adjustment being achieved mechanically by means of a screw adjustment or the use of another adjusting tool. Such a distractor device is disclosed in application Ser. No. 60/954,507 titled "Device and Method for Variably Adjusting Intervertebral Distraction and Lordosis" filed Aug. 7, 2007.

In a further embodiment the distractor apparatus can be mated with a stereotactic navigational device to establish, monitor and control the positioning of the device relative to the adjacent vertebra.

After distraction and lordotic adjustment has been achieved the spinal bridge is located on the vertebrae relative to the distractor device and attached to the adjacent vertebra by at least two bone screws, securing the vertebrae in their prescribed positions.

If intervertebral distractor devices have been employed they are removed, exposing a predefined accessible and constrained operating field allowing the controlled cutting and removal of tissue to occur.

In a further embodiment the vertebral plate can accommodate insertable control templates which can be placed within it by the surgeon to further assist precise tissue removal.

In a further embodiment the vertebral plate can serve as a mounting base for the attachment of soft tissue retractors, further aiding the surgeon by assuring an un-impeded surgical field.

In a further embodiment the vertebral plate can be removed after the placement of a disc arthroplasty device.

The intervertebral repair device may be generally wedge shaped, it may have an initial radius or taper for engagement with the adjacent vertebrae or it may be conically or cylindrically shaped.

Further, this device may have surface contours thereon which are intended to increase the surface area of contact between said surfaces and the exposed cancellous hone tissue and to increase the intimate compressive engagement with said cancellous tissue so as to induce and encourage osteogenesis therein.

BRIEF DESCRIPTION OF THE DRAWINGS

FIGS. 15A-15C show an exemplary interbody repair implant.

FIGS. 16A-16C show an exemplary intervertebral distraction device.

DETAILED DESCRIPTION

Figure 1A:
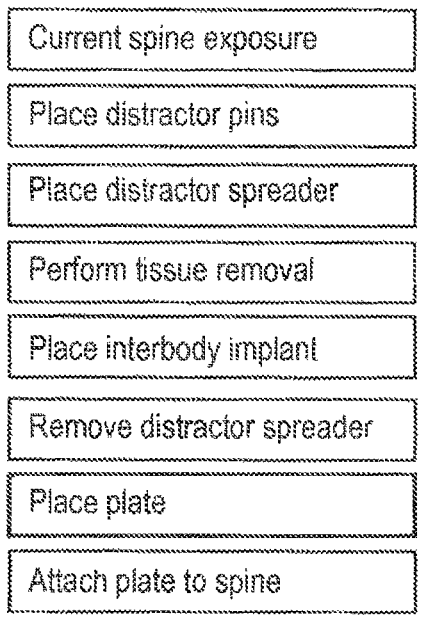
FIG. 1A shows the typical sequence of steps in a current surgical procedure.
Figure 1B:
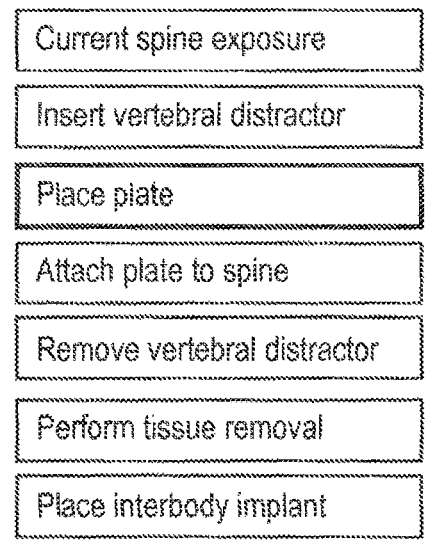
FIG. 1B shows the sequence of one embodiment of the inventive method herein.

FIG. 1A describes the typical operational sequence currently employed, wherein vertebrae are distracted, tissue is excised, an implant in placed between adjacent vertebrae and a bone plate is attached. FIG. 1B describes the preferred operational sequence associated with this invention, wherein vertebrae are distracted and placed in their preferred relative angular positions and a vertebral frame is attached to adjacent vertebrae using bone screws to maintain the prescribed spatial relationship during the subsequent steps. In an alternative sequence, the vertebral frame may be attached to adjacent vertebrae prior to distraction and preferred positioning. Thereafter tissue is excised though the aperture in the frame, the implant is inserted through said aperture. A retaining member may be attached to said vertebral frame to maintain the position of the implanted insert and to prevent back-out of the bone screws.

Figure 2A:
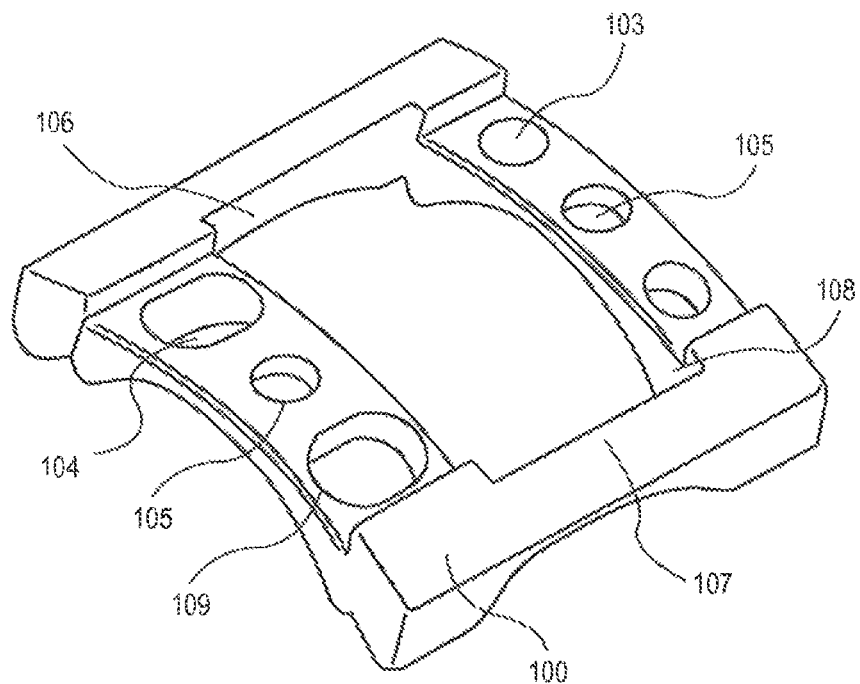
FIG. 2A is an anterolateral isometric view of a single level implantable bone plate.
Figure 2B:
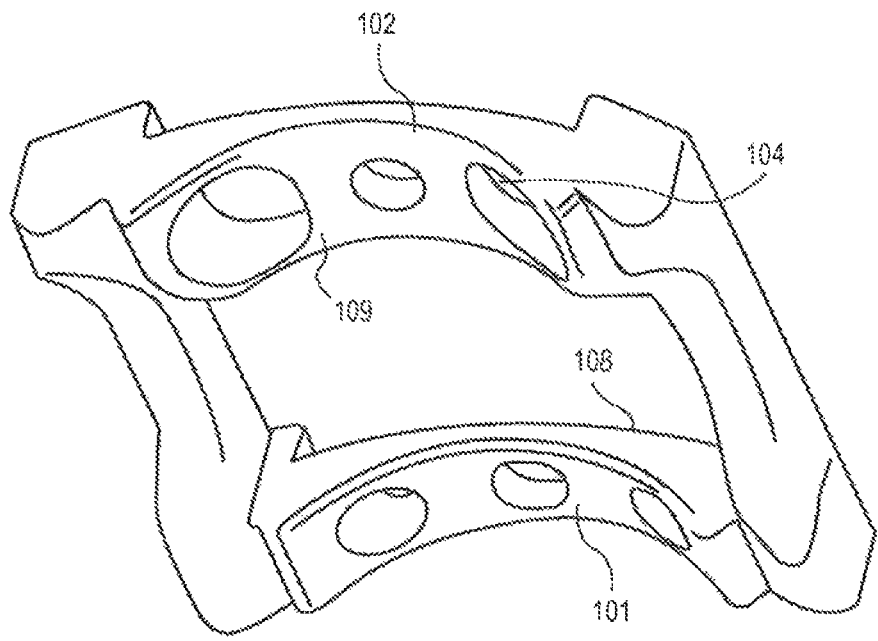
FIG. 2B is a posterolateral isometric view of a single level implantable bone plate.

FIGS. 2A and 2B depict a single level vertebral frame 100, intended to secure two adjacent vertebrae. The device has surfaces 101 and 102 which are generally contoured to engage positively with the anterior surfaces of the adjacent vertebrae. The device has through holes 103 and 104 intended to accommodate the insertion of bones screws into the vertebral tissue. Holes 104 may be elongated to accommodate post surgery dynamic settling of the vertebrae. The device further has one or more holes 105 intended for receiving screws (or other fixation devices) securing the retaining member thereto or there-through. The receiving holes 105 also provide a mounting means for the insertion of temporary soft tissue retractor pins. The device has an operating window defined by the side walls 106, 107, 108 and 109. This window is intended to allow unimpaired access to the intervertebral space in order to excise tissue and subsequently to allow the insertion of the interbody repair device there-through.

Figure 3A:
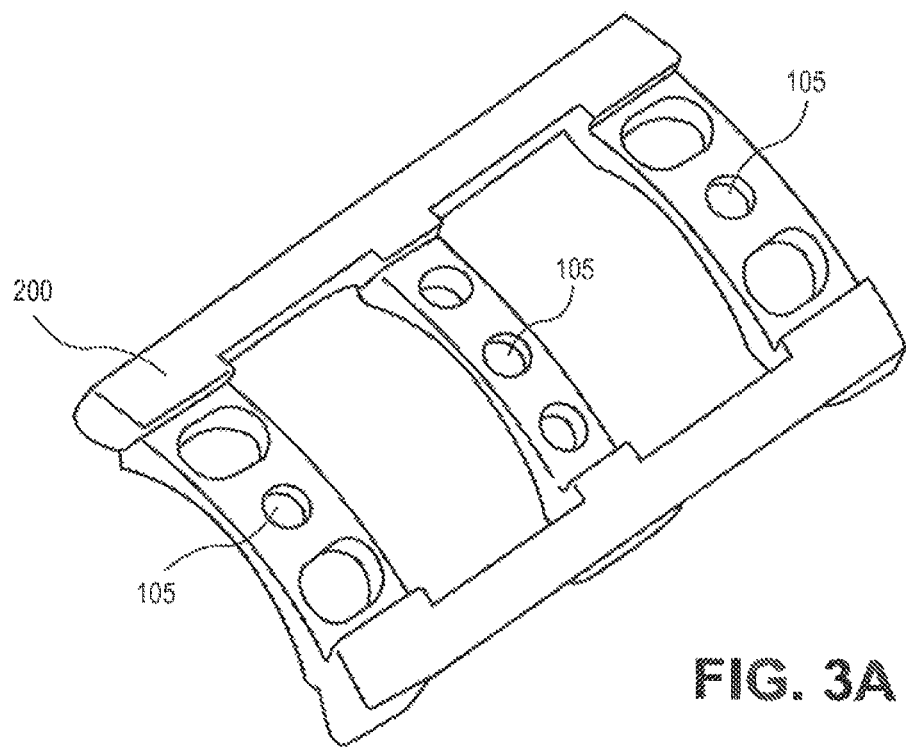
FIG. 3A is an anterior isometric view of a multi-level implantable bone plate.

FIG. 3A depicts a multi-level vertebral frame 200, intended to facilitate the orientation, fixation and repair of three or more vertebrae.

Figure 3B:
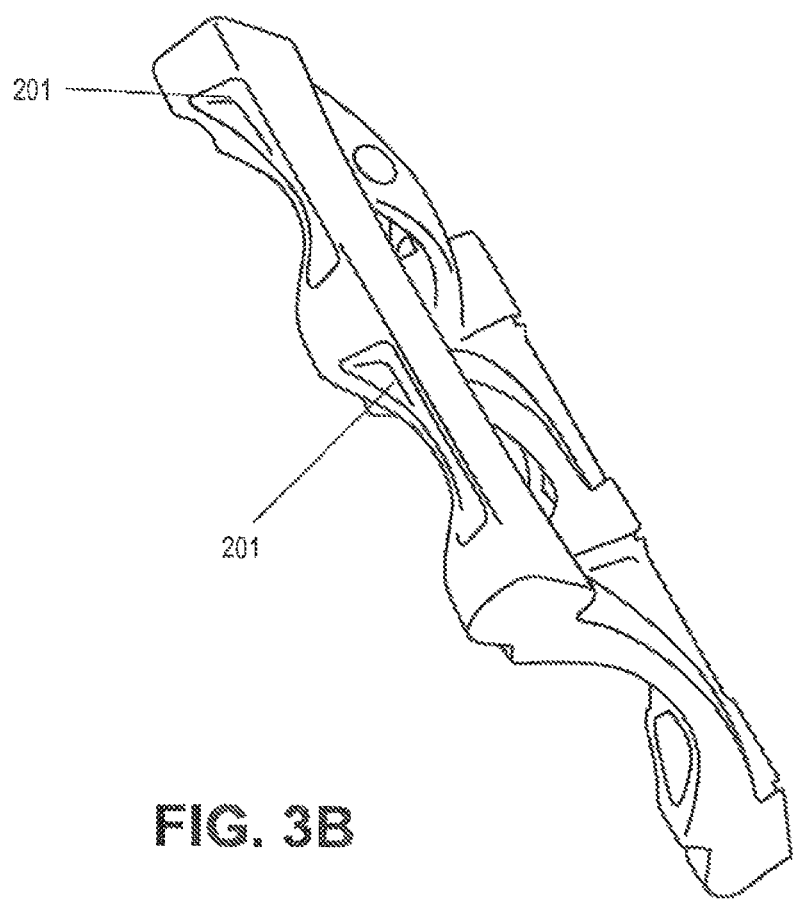
FIG. 3B is a lateral isometric view of a multi-level implantable bone plate.

FIG. 3B depicts a side view of a multilevel device and illustrates the presence of a receiving means 201 on the vertebral frame, thereby permitting the plate to accommodate the location and retention of soft tissue retractor blades.

Figure 4:
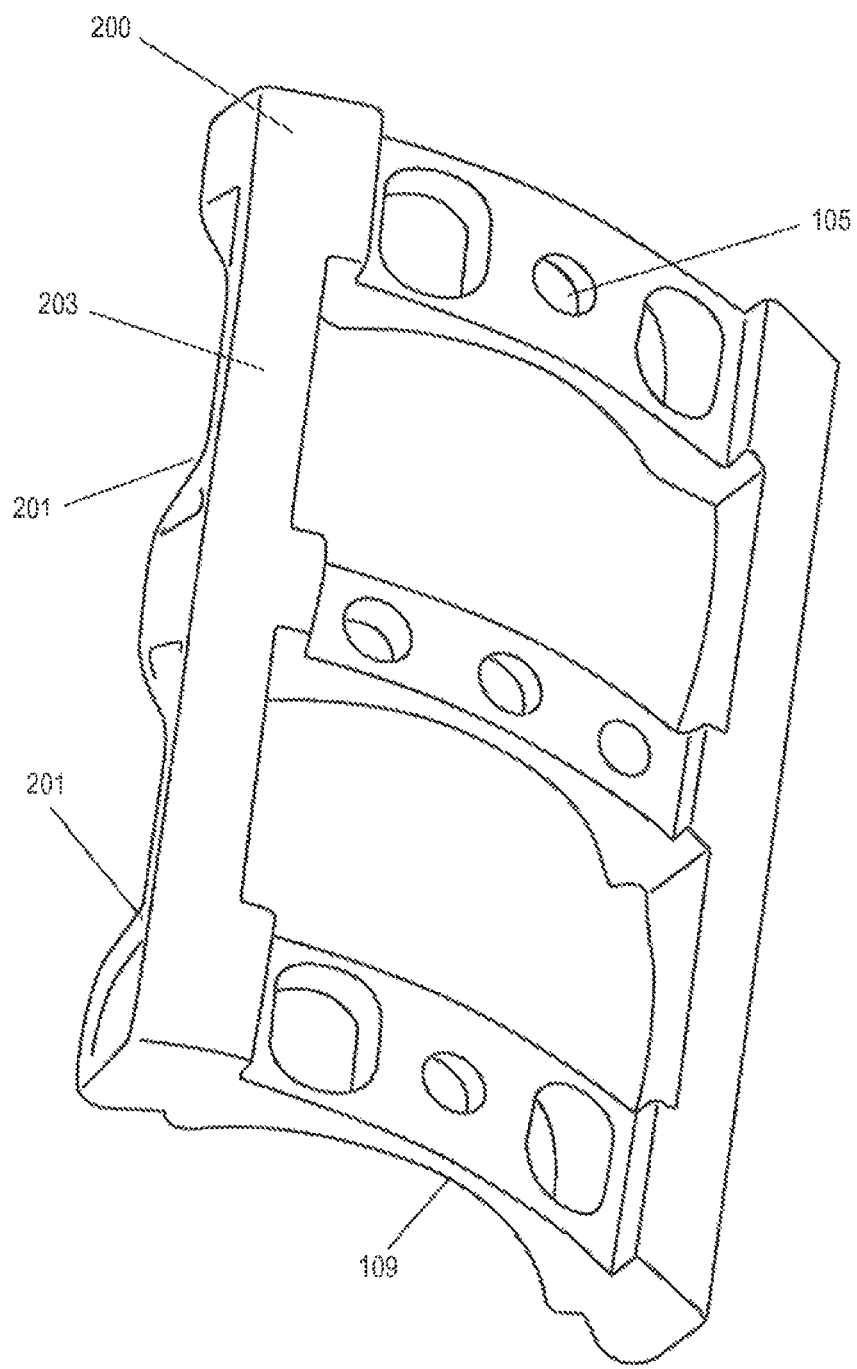
FIG. 4 is an oblique perspective view of a multi-level bone plate.
Figure 5:
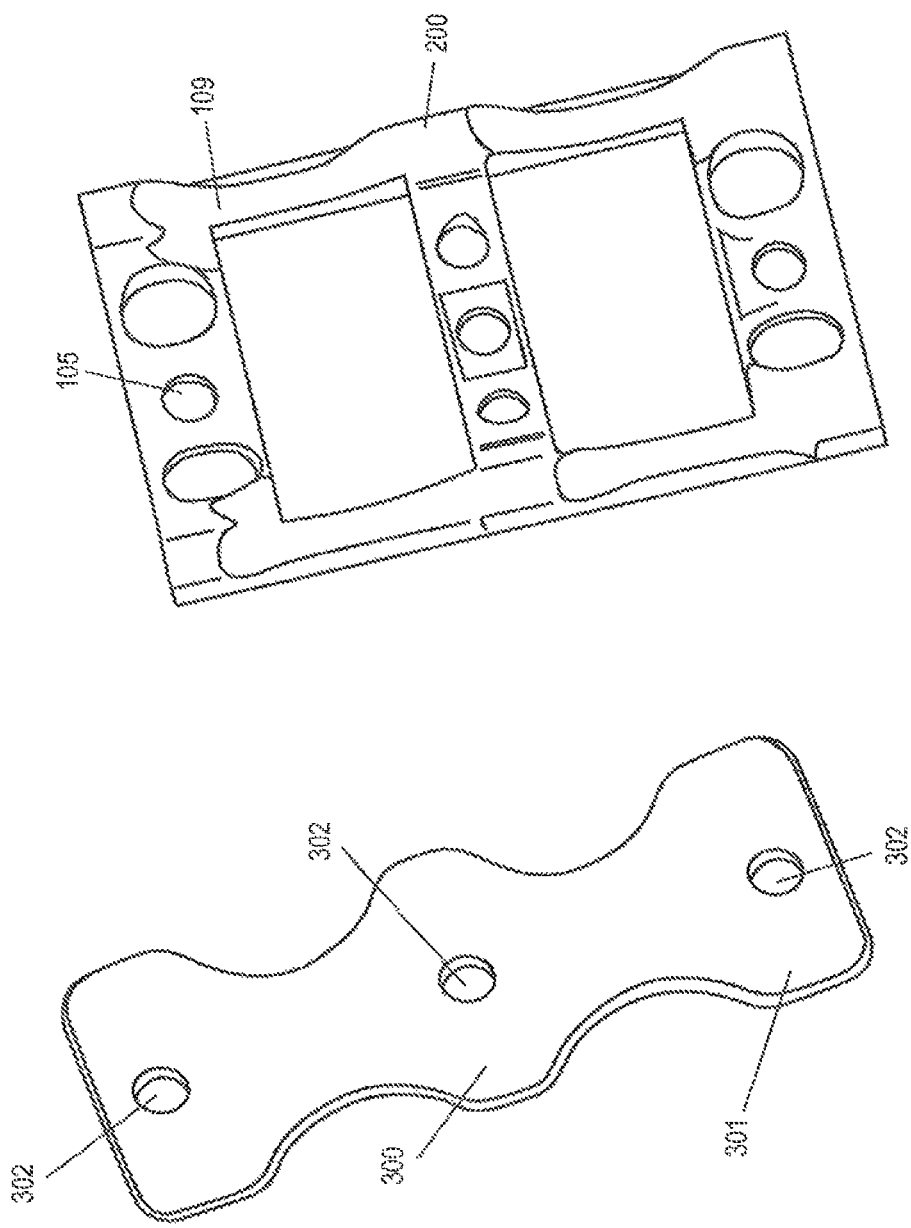
FIG. 5 illustrates a retention member relative to the vertebral frame.

Referencing FIGS. 4 and 5; the retention member 300 has a posterior surface 301 contoured to match the anterior surface of the vertebral frame 200 and through holes 302 which align with the receiving holes 105 in the vertebral frame, these holes being intended to secure the retention member 300 to the vertebral frame 200 in order to retain the interbody implant in position and to prevent the back-out of the bone screws used to secure frame 200 to the vertebral bone tissue.

Figure 6:
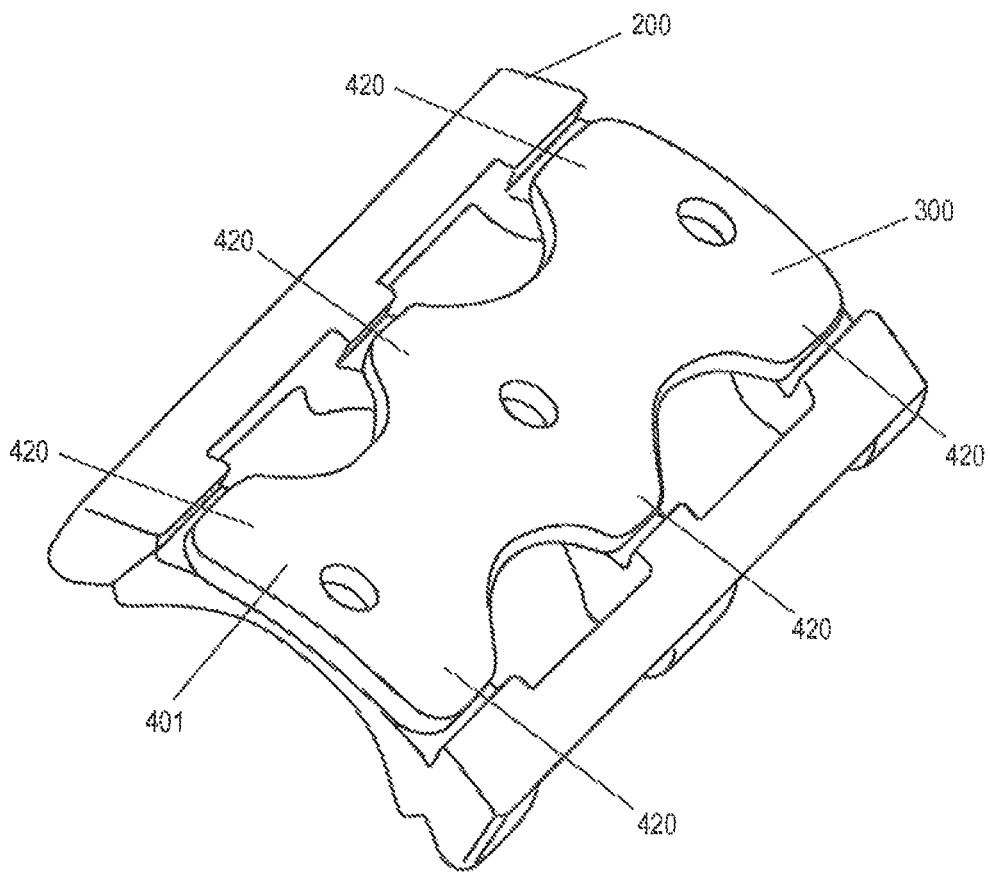
FIG. 6 depicts a retention member in an installed position on the vertebral frame.

FIG. 6 shows retention member 300 installed to the vertebral frame 200, the anterior surface of the retention member having a contour 401 which generally matches that of the vertebral frame 200 to create a smooth, continuous surface after installation.

FIG. 6 further shows the retention member having extensions 420 that cover the bone screws and thereby preventing screw back-out.

Figure 7:
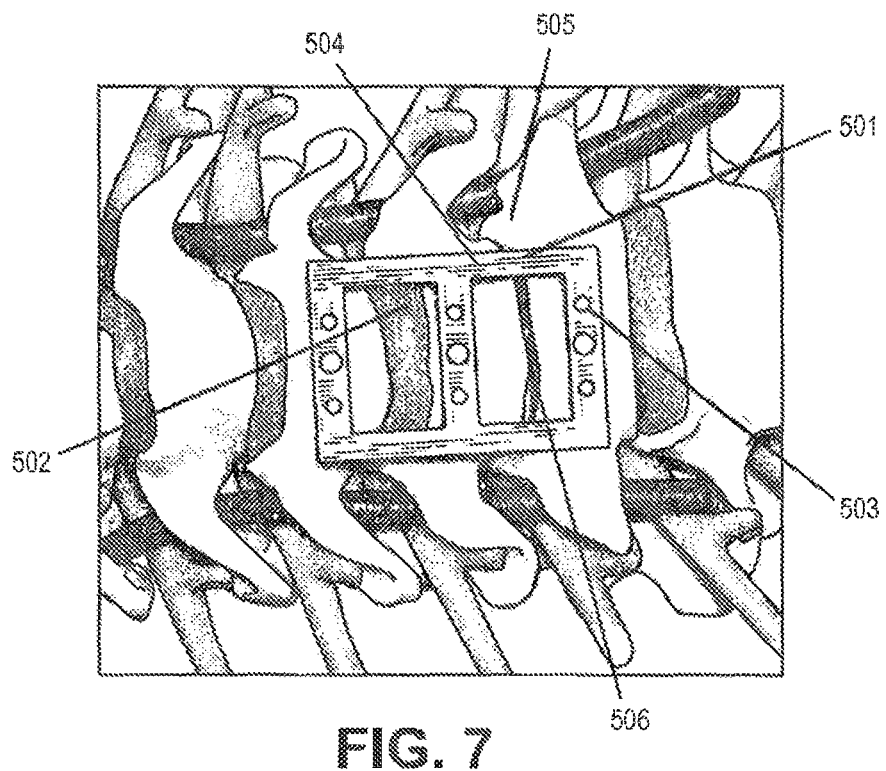
FIG. 7 is an anterior (surgical) view of a vertebral frame in its installed position on adjacent vertebrae.

FIG. 7 depicts the vertebral frame in position on adjacent vertebrae and illustrates the operating window in the region of the disk space. The operating window is defined by the cross members 503, 504, 505 and 506 respectively which produce a contained area through which all procedures may be executed. Further, these members act to restrain the surgeon during tissue excision and thereby minimize the risk of accidental damage to surrounding tissue.

FIG. 7 further illustrates how the device provides access to facilitate the removal of disk material 502 and the preparation of the intervertebral space 501 prior to the insertion of the interbody implant.

Figure 8:
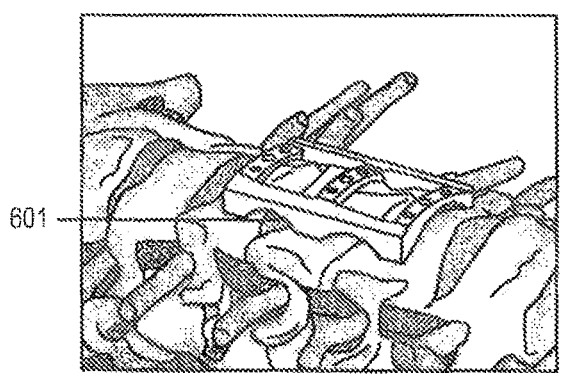
FIG. 8 is an anterolateral perspective view of the vertebral frame in its installed position on adjacent vertebrae.

FIG. 8 is a perspective side view of the vertebral frame in the installed position on adjacent vertebrae. The device has clearance spaces 601 in the region of the disk material to accommodate a better fit to the vertebral surfaces and to provide additional clearance to allow for the removal of unwanted bone material after device installation.

Figure 9:
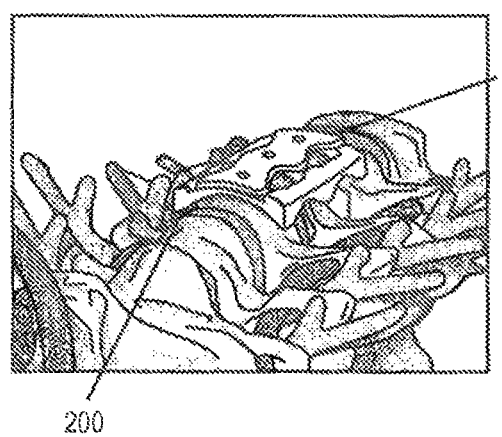
FIGS. 9 and 10 depict a retention member in-situ after installation onto the vertebral plate.
Figure 10:
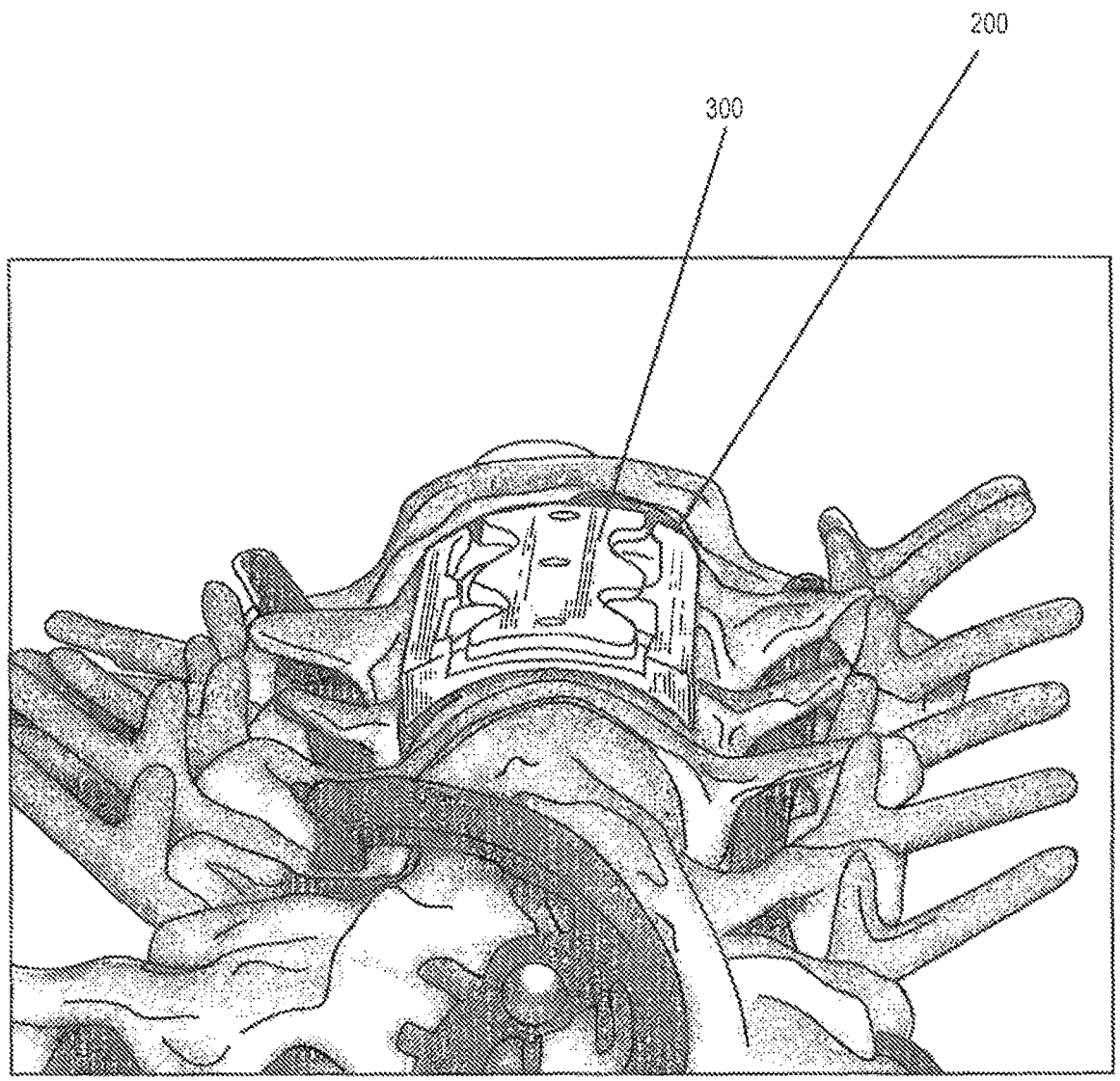

FIGS. 9 and 10 depict the retention member 300 placed in-situ on the vertebral frame 200 after the insertion of the interbody implant. The member 300 is located so as to prevent substantial movement of the interbody implant and thereby promote bone tissue growth therein.

Instead of screws, or in combination therewith, one or more snap lock devices may be used to attach retention member 300 to vertebral frame 200. Such devices may employ a compressible feature, such as a split barb, that locks into place when inserted sufficiently into hole 105 or other mating feature. By using snap lock device(s), member 300 can be simply aligned with frame 200 and pressed into place without requiring the surgeon to align screws and install them with a driver. One or more cam lock devices may also be used, alone or with screws and/or snap lock devices. In some cam lock embodiments a torsional force is applied to a component, inducing rotation and causing it to become engaged in a corresponding feature within a receiving element. This twisting action causes the component to turn and lock under another component, again with less effort than required when installing a screw.

The system offers substantial benefits over those previously disclosed and those currently employed. These benefits include, but are not limited to:

A novel method which allows for precise control and fixation of optimal vertebral position.

2 Constrained and controlled tissue removal

3 Elimination of patient to patient variation 4) integration of soft tissue retraction devices 5) Reduction in surgical time and maneuvers throughout the case.

Referring to FIGS. 11-16 another exemplary embodiment of an implantable vertebral frame system and method of use will be described. FIGS. 11A-11F show the vertebral frame itself and the associated screws of this embodiment. Frame 700 is similar in construction and method of use to previously described frame 100. In this embodiment, frame 700 is curved in the mediolateral direction (as best seen in FIG.

Figure 11A:
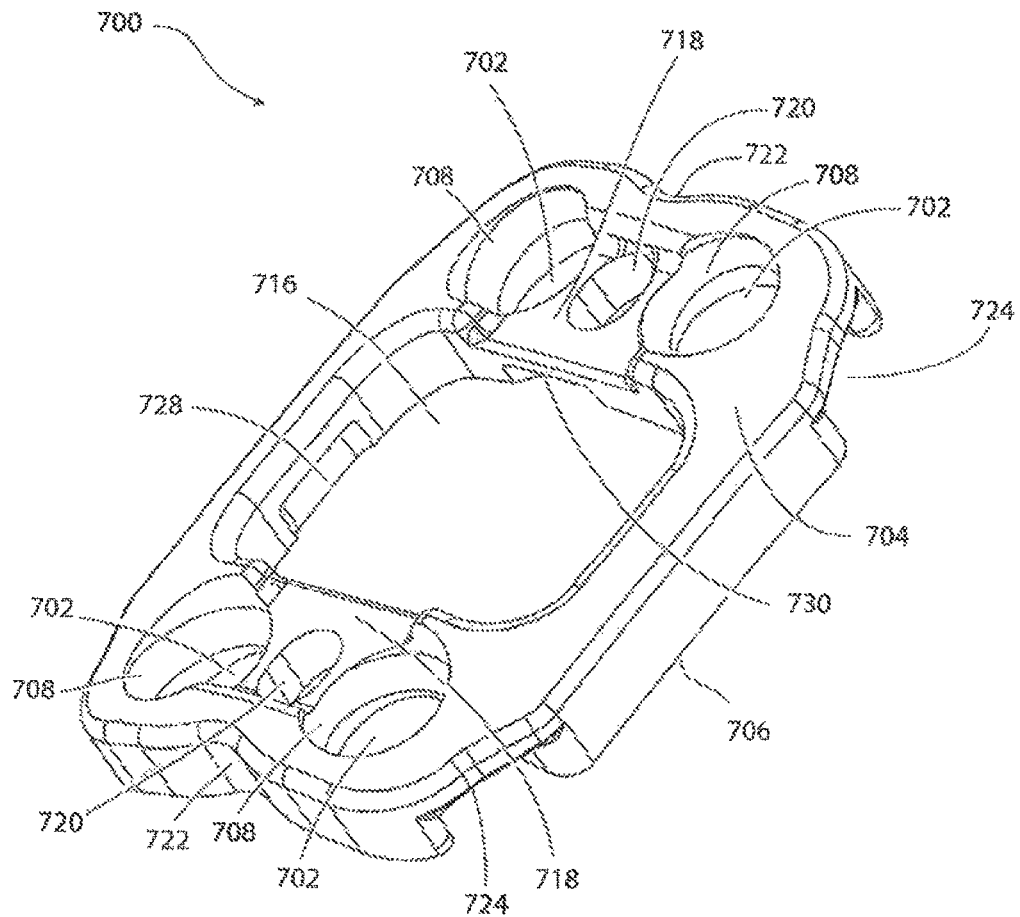
FIGS. 11A-11E show another embodiment of an implantable bone plate.
Figure 11B:
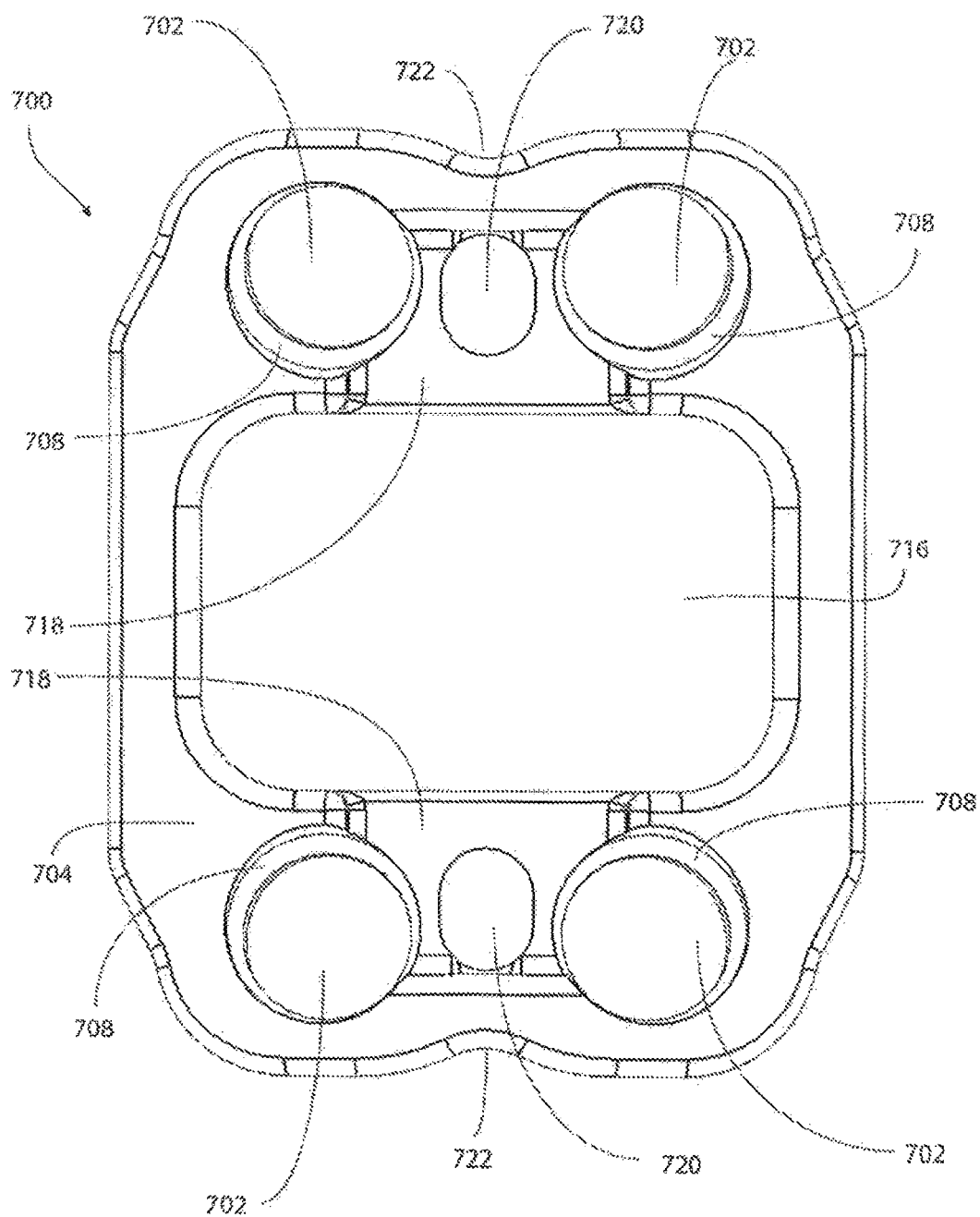
Figure 11C:
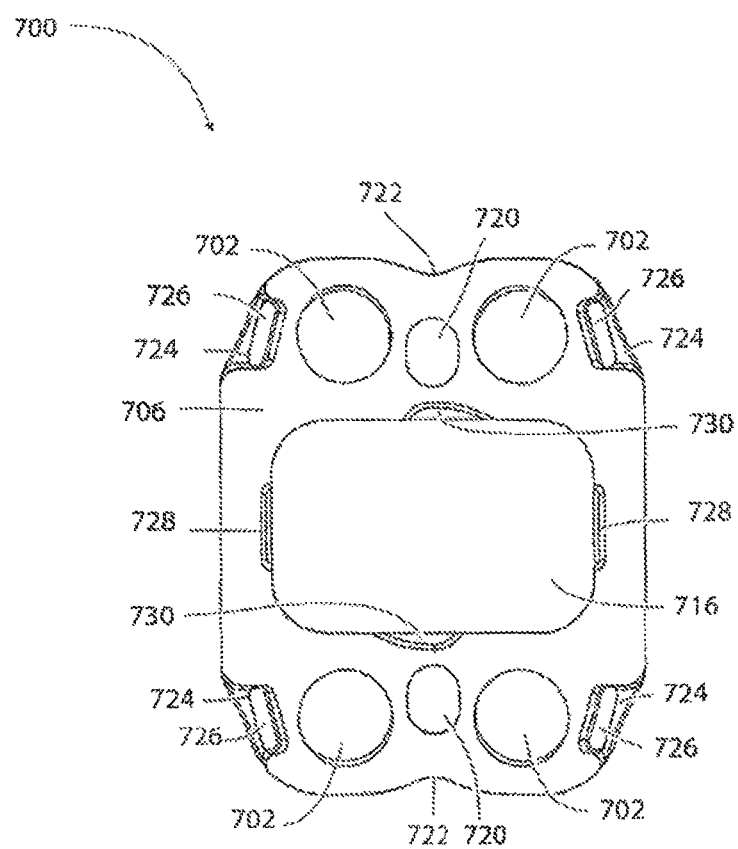
Figure 11D:
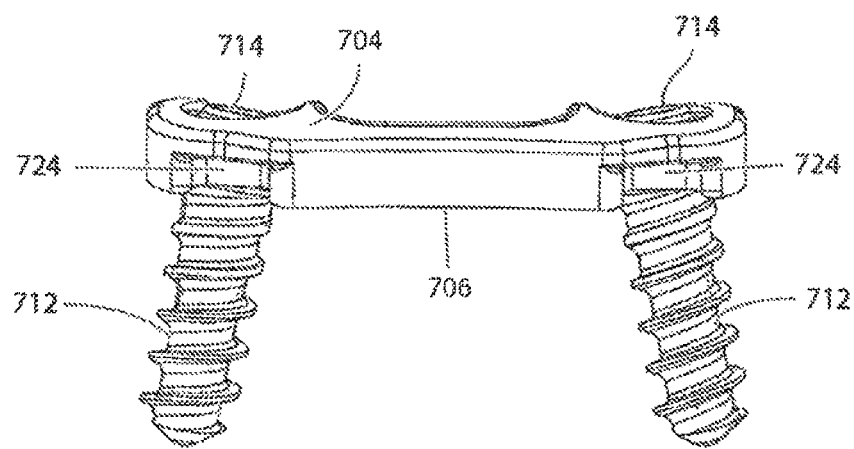
Figure 11E:
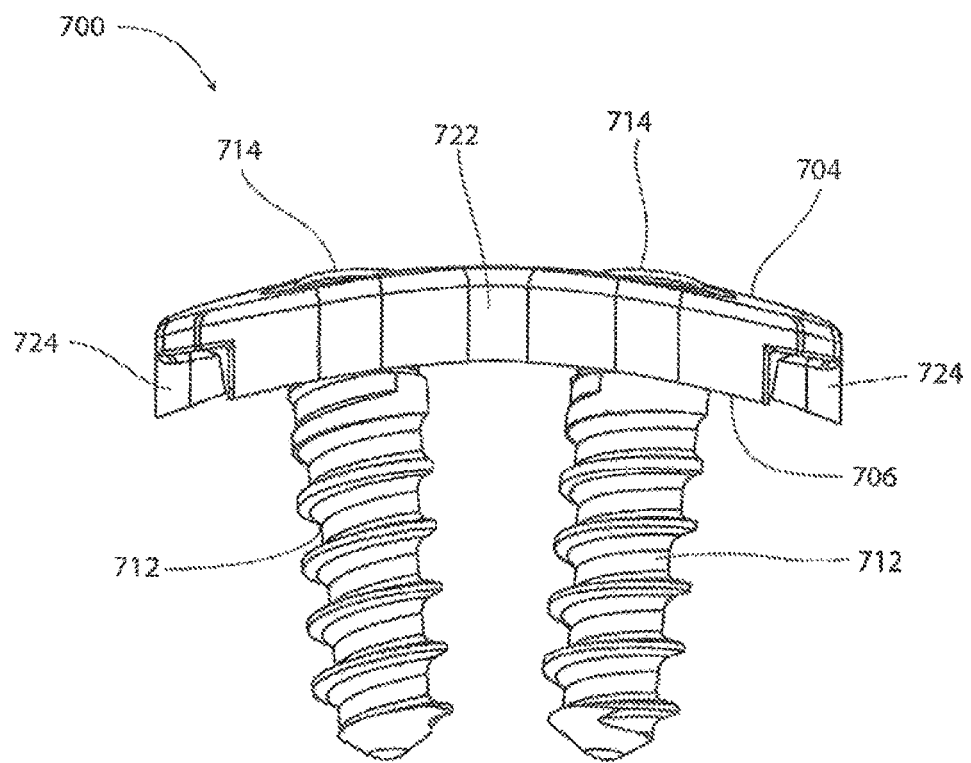
Figure 11F:
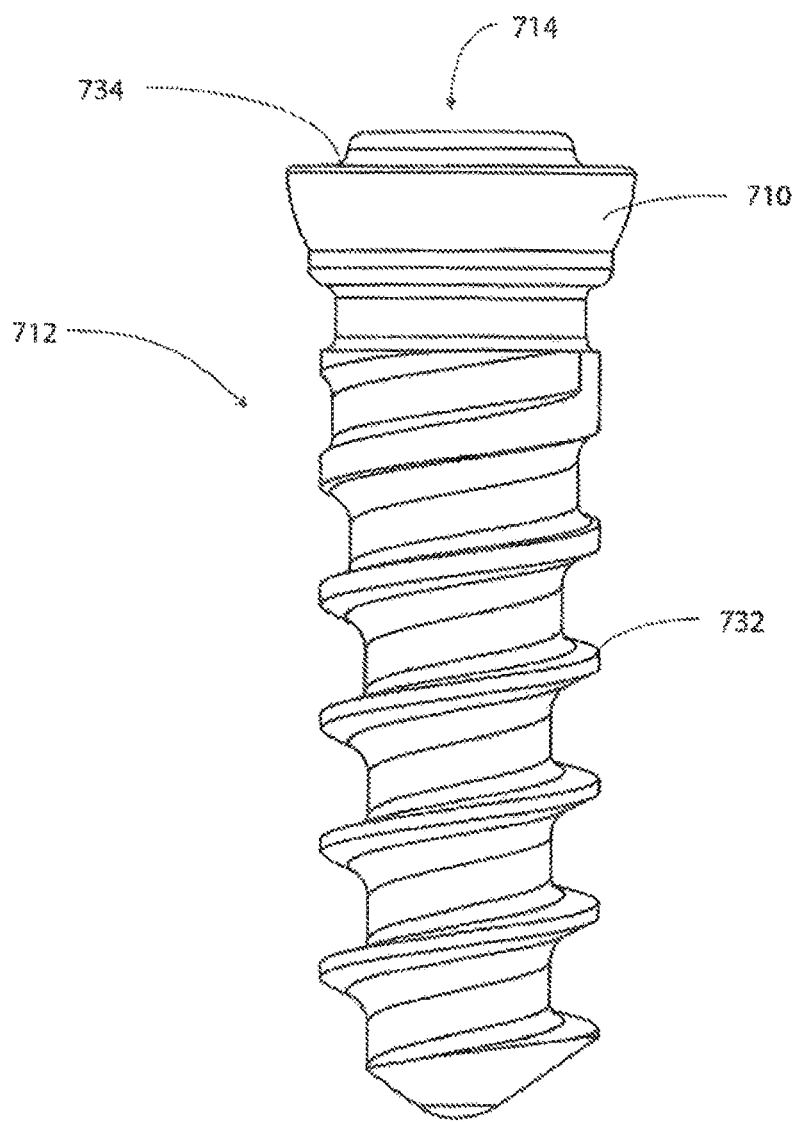
FIG. 11F is a side view showing an exemplary bone screw for use with the implantable bone plate of FIGS. 11A-11E.

11E) and generally straight in the craniocaudal direction (as best seen in FIG. 11D) to match the anterior surfaces of adjacent vertebrae to which frame 700 will be affixed. In other embodiments, the frame may also be curved in the craniocaudal direction. In some embodiments it is desirable to have the radius or radii of curvature as small or smaller than the associated radii of the adjacent vertebrae to ensure that the frame does not wobble when mounted on the vertebrae. In some embodiments, frame 700 has a radius of curvature of about 25 mm, an overall length of about 25 mm, an overall width of about 19 mm, and a plate thickness of about 2.5 mm. It is Frame 700 includes four bone screw holes 702 extending through frame 700 from its anterior face 704 to its posterior face 706. As best seen in FIG. 11A, the anterior side of each hole 702 may be provided with a spherically curved countersink 708. Spherical countersink 708 mates with a complementary shaped spherical shoulder 710 on bone screw 712, as shown in FIG. 11F. Countersink 708 and shoulder 710 cooperate to allow bone screw 712 to be inserted through screw hole 702 in a wide range of mediolateral and craniocaudal angles while still allowing the head 714 of screw 712 to remain firmly seated against frame 700 when installed to prevent movement of frame 700. As best seen in FIG. 11D, bone screw holes 702 and countersinks 708 can be configured to provide nominal screw angles such that screws 712 angle away from each other in the craniocaudal direction. As best seen in FIG. 11E, bone screw holes 702 and countersinks 708 can be configured to provide nominal screw angles such that screws 712 angle towards each other in the mediolateral direction. While the spherical countersinks 708 allow the surgeon to vary the screw angle from nominal as previously described, these nominal compound screw angles allow frame 700 to withstand greater extraction forces in the anterior direction than if each screw were perpendicular to frame 700, thereby allowing frame 700 to be affixed to the adjacent vertebral bodies more rigidly.

Referring to FIGS. 11A and 11B, frame 700 also includes an operating aperture 716 through its midsection, the purpose of which will be later described. In this exemplary embodiment, operating aperture 716 has a height of about 10.5 min and a width of about 15 mm. Coplanar reference surfaces 718 may also be provided, such as along the longitudinal centerline of frame 700 on opposite sides of operating aperture 716 as shown. Surfaces 718 may be held to high tolerances to provide accurate datum points for surgical tools and a cover plate that will be later described. Slotted through holes 720 or similar features may be provided on opposite sides of operating aperture 716 to allow frame 700 to be placed over distractor pins located in adjacent vertebrae. Slotted holes 720 may also serve as additional datum points. In this exemplary embodiment, all other critical features of frame 700 are formed in reference to surfaces 718, holes 720, and the edges of operating aperture 716 adjacent to surfaces 718. Frame 700 may be provided with indents 722 along the longitudinal centerline of frame 700 to aid the surgeon in placing frame 700 on the centers of adjacent vertebral bodies.

Referring to FIGS. 11A and 11C-11E, recesses 724 may be provided in each corner of frame 700 as shown for anchoring mating prongs of soft tissue retractors, as will be subsequently described in more detail. As shown ire FIG. 11C, an anteriorly extending pocket 726 may be formed in the generally posteriorly facing surface of each recess 724 to more positively engage the mating prongs of the retractors.

Referring to FIGS. 11A and 11C, two pairs of opposing undercuts 728 and 730 are shown on the posterior face 706. The first pair of undercuts 728 are on mediolaterally opposite sides of operating aperture 716 and each have a posteriorly facing surface located between the anterior face 704 and posterior face 706 of frame 700. These undercuts 728 serve to receive snap-fit protrusions of a cover plate to temporarily hold it in place, as will be subsequently described in more detail. The second pair of undercuts 730 are on craniocaudally opposite sides of operating aperture 716 and also each have a posteriorly facing surface located between the anterior face 704 and posterior face 706 of frame 700. These undercuts 730 serve to receive the distal ends of a rotatable locking arm of the cover plate to permanently hold the cover plate in place, as will also be subsequently described in more detail.

Referring to FIG. 11F, a proprietary bone screw 712 may be used with the inventive frame 700. Screw 712 includes a head 714 and a threaded shank 732. Threaded shank 732 may be configured to be self drilling and/or self tapping. As previously described, screw 712 also includes a shoulder portion 710. Screw 712 may be provided with head relief portion 734 to cooperate with a screw locking portion of a cover plate, as will be subsequently described in detail.

As shown in FIGS. 11A-11E, the vertebral frame 700 in this embodiment is completely symmetrical about the longitudinal and transverse centerlines. This allows the surgeon to install the plate on the vertebrae without having to first determine a proper craniocaudal orientation.

Referring to FIGS. 12A-12G, an exemplary cover plate 750 configured to interface with vertebral frame 700 is shown. In this exemplary embodiment, cover plate 750 serves to prevent an intervertebral implant from moving anteriorly, and prevents screws 712 from hacking out of the vertebral bodies.

Figure 12A:
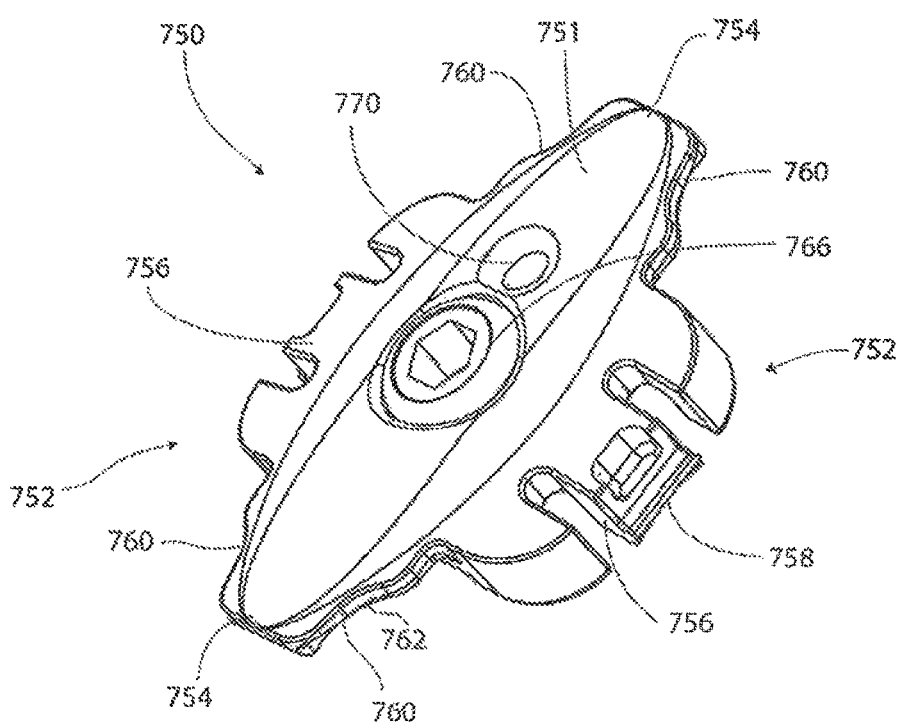
FIGS. 12A-12F show an exemplary cover plate for use with the implantable bone plate of FIGS. 11A-11E.
Figure 12B:
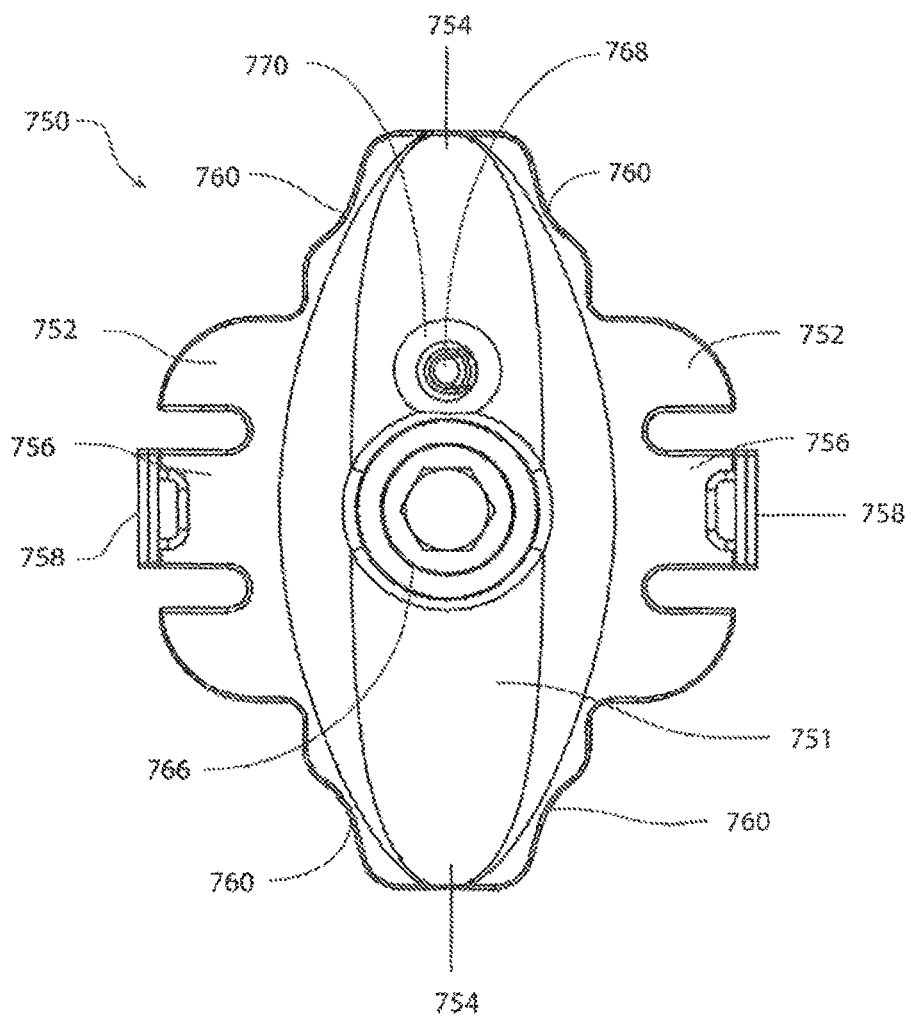
Figure 12C:
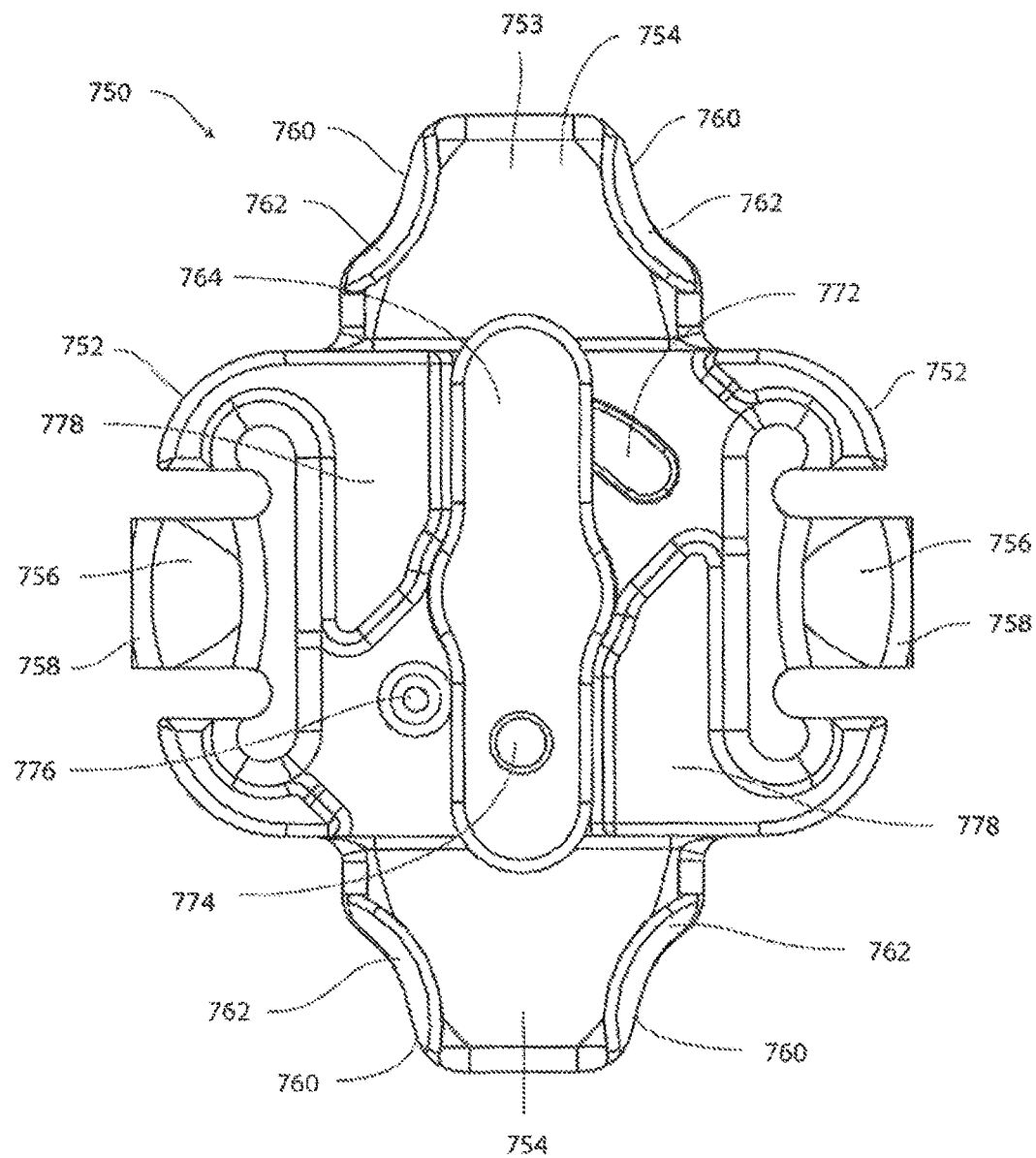
Figure 12D:
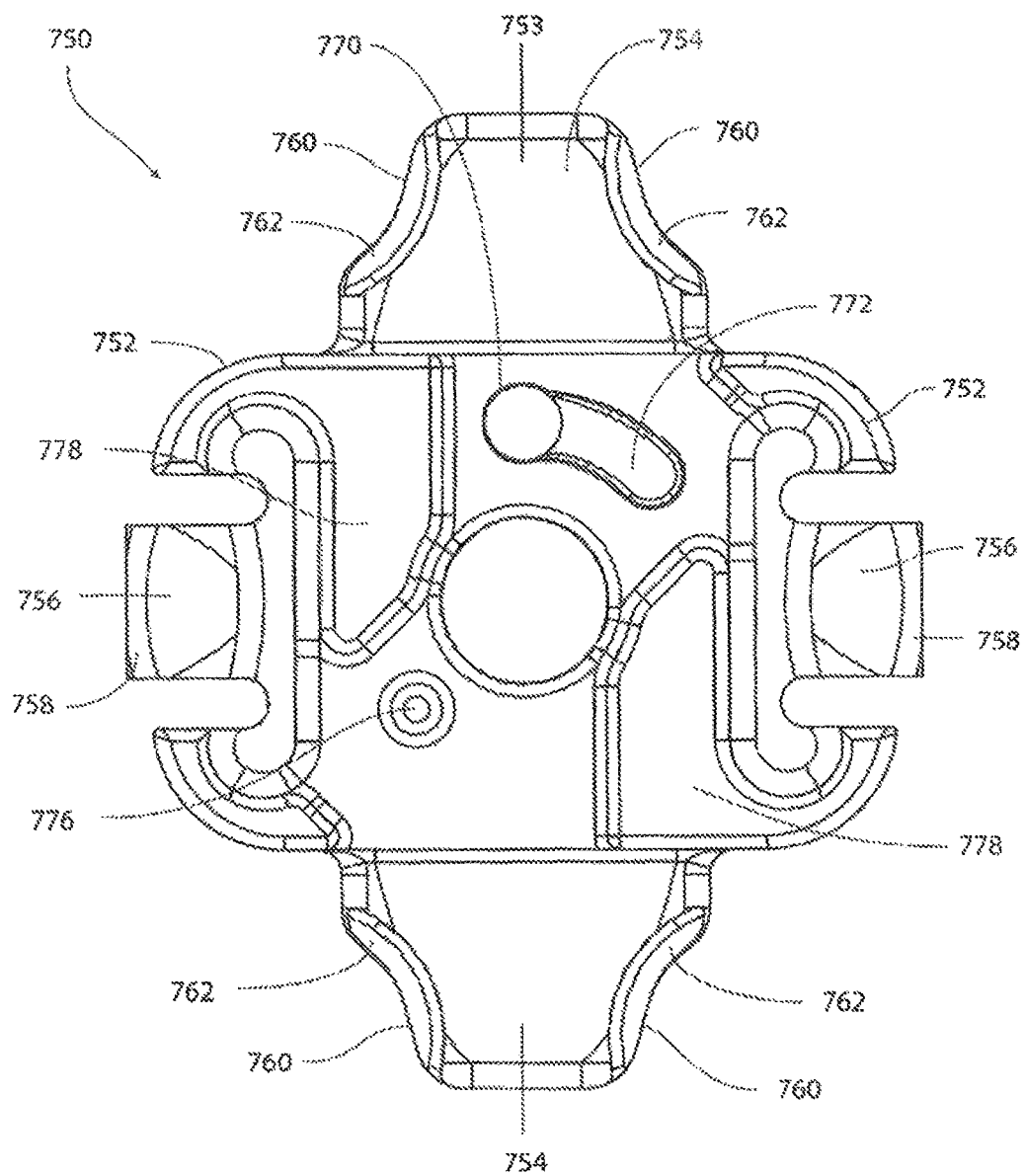
Figure 12E:
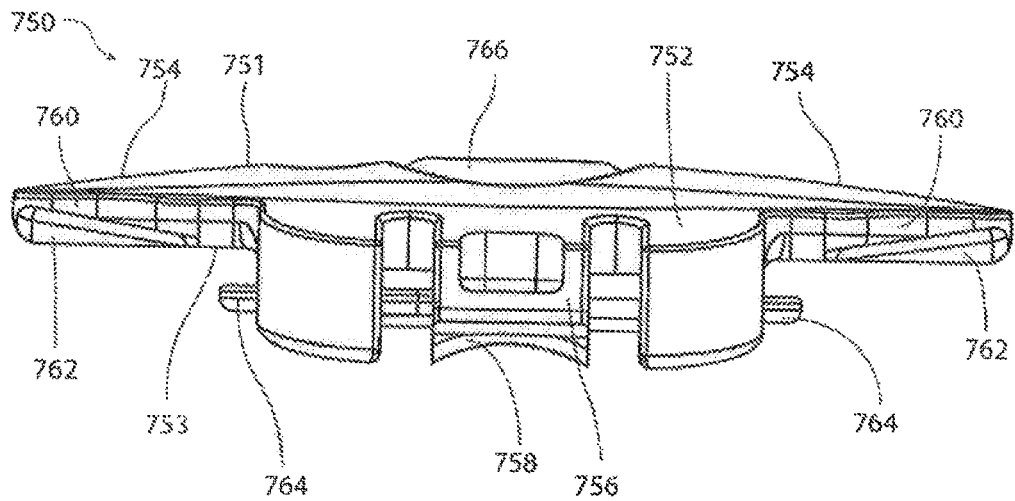
Figure 12F:
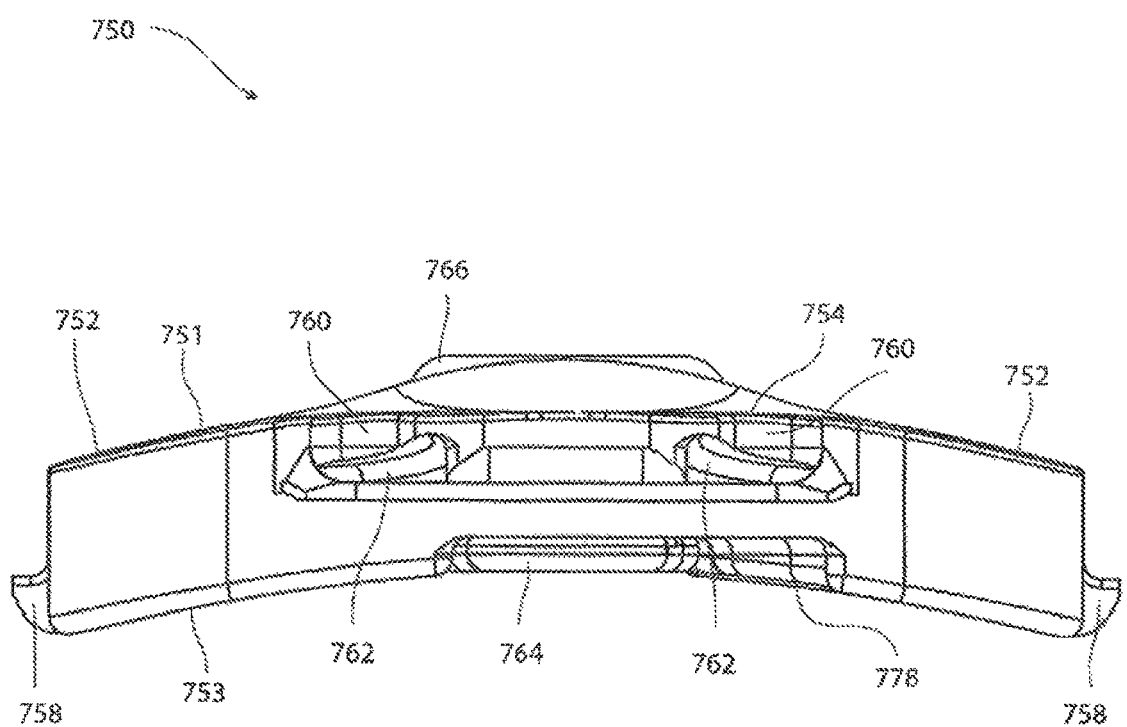

Cover plate 750 may be curved in mediolateral direction, as best seen in FIG. 12F, to generally match the curvature of frame 700. In this exemplary embodiment, cover plate has an anterior side 751 and a posterior side 753. Cover plate 750 may include a pair of opposing mediolateral wings 752 and a pair of opposing craniocaudal wings 754. When cover plate 750 is installed on frame 700, the central portion of cover plate 750 and the mediolateral wings 752 are received within the operating aperture 716 of frame 700 and serve to cover aperture 716. Mediolateral wings 752 each comprise a laterally extending arm 756 with a tongue 758 located at its distal posterior edge. Each tongue 758 is engagable with one of the previously described opposing undercuts 728 of frame 700. This arrangement allows a surgeon to snap cover plate 750 in place and have it temporarily held in place by tongues 758 locking into undercuts 728. In this embodiment, arms 756 have some resiliency, allowing them to flex as tongues 758 begin entering operating aperture 716 and before entering undercuts 728. Craniocaudal wings 754 cover reference surfaces 718 of frame 700 when installed. Additionally, distal portions 760 of craniocaudal wings cover a portion of screw heads 714, as will be subsequently described in more detail. As best seen in FIG. 12C, distal portions 760 include undercuts 762 for engaging head relief portions 734 of screws 712.

Figure 12G:
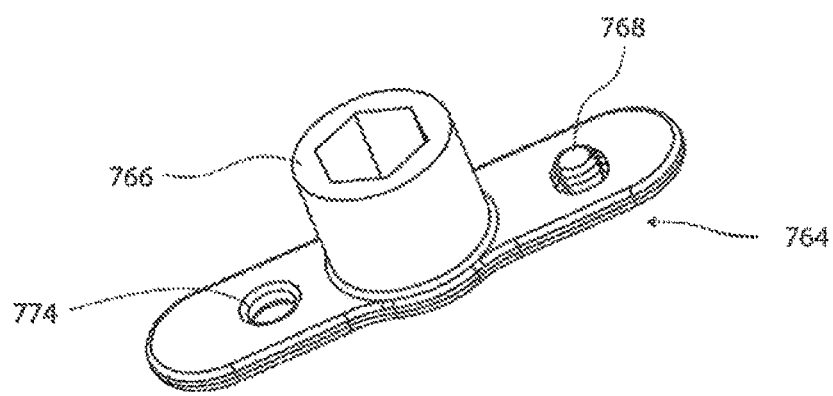
FIG. 12G is a perspective view showing an exemplary locking arm for use with the cover plate of FIGS. 12A-12F.

Referring to FIG. 12G, a locking arm 764 configured for permanent assembly with cover plate 750 is shown. Locking arm 764 may be a unitary member that snaps into a central bore of cover plate 750, or may comprise a separate arm that is swaged, press fit or otherwise fixedly secured to locking socket 766 before or during assembly with cover plate 750. Once assembled, locking arm 764 is rotably retained on cover plate 750 with locking socket 766 accessible from the anterior side 768 of cover plate 750, as shown in FIGS. 12A and 12B. Locking arm 764, which is driven by locking socket 766, is located on the posterior side 770 of cover plate 750, and is rotatable between a locked position, as shown in FIG. 12C, and an unlocked position, as shown in FIG. 165. When in the locked position, the distal ends of locking arm 764 are received within the second pair of undercuts 730 on opposite ends of operating aperture 716 in frame 700, shown in FIG. 11A. In this position, cover plate 750 is securely locked to frame 700 since reference surfaces 718 (FIG. 11A) are captured between locking arm 764 and the craniocaudal wings 754 of cover plate 750 (FIG. 12C). In other embodiments (not shown), the locking arm engages the frame on opposite mediolateral sides instead of craniocaudal sides.

Locking arm 764 may include a raised dimple 768, as shown in FIG. 12G, that extends from the locking arm towards the underside of cover plate 750. Cover plate 750 may be provided with a through-hole 770, as shown in FIG. 12D, for receiving the raised dimple 768 when locking arm 764 is in the locked position. Cover plate 750 may also be provided with a ramped recess 772 adjacent to hole 770. Recess 772 becomes deeper as it extends away from hole 770. This arrangement biases locking arm 764 toward the unlocked position as dimple 768 is urged toward the bottom of the ramp at the opposite end of recess 772 from hole 770. This arrangement also provides better tactile feedback to the surgeon, who feels increasing resistance when turning locking socket 766, until dimple 768 snaps into hole 770. Dimple 768 and/or locking arm 764 may have a different color that contrasts with cover plate 750 to provide visual feedback through hole 770 when locking arm 764 is in the fully locked position. Dimple 768 and arm 764 may be configured to click when entering hole 770. Accordingly, the surgeon may be provided with tactile, visual and audible confirmation when arm 764 is in the fully locked position.

Through hole 774 may be provided in locking arm 764, as shown in FIG. 12G, to align with blind hole 776 in cover plate 750, as shown in FIG. 12D, when locking arm 764 is in the unlocked position. Holes 774 and 776 may be used in conjunction with assembly tooling (not shown) when cover plate 750 is being manufactured. Raised portions 778 may be provided on the posterior side of cover plate 750, as shown in FIGS. 12C and 12D, to limit the travel of locking arm 764. In some embodiments, the travel of arm 764 between the unlocked and locked positions is about 45 degrees.

Cover plate 750 may be made of PEEK so as to be radiolucent. This allows bone growth into an implant beneath cover plate 750 (as will be subsequently described) to be viewed with various imaging techniques. Locking arm 764 may be made of titanium so its locked status can be confirmed by imaging.

Referring to FIGS. 13A-13G, an exemplary instrument guide 800 configured for use with vertebral frame 700 is shown. Instrument guide 800 has a proximal end 802 and a distal end 804. A handle 806 may be provided for holding guide 800 in place during a surgical procedure. In some embodiments, a removable divider or insert 808 is configured to be received within guide 800.

Figure 13A:
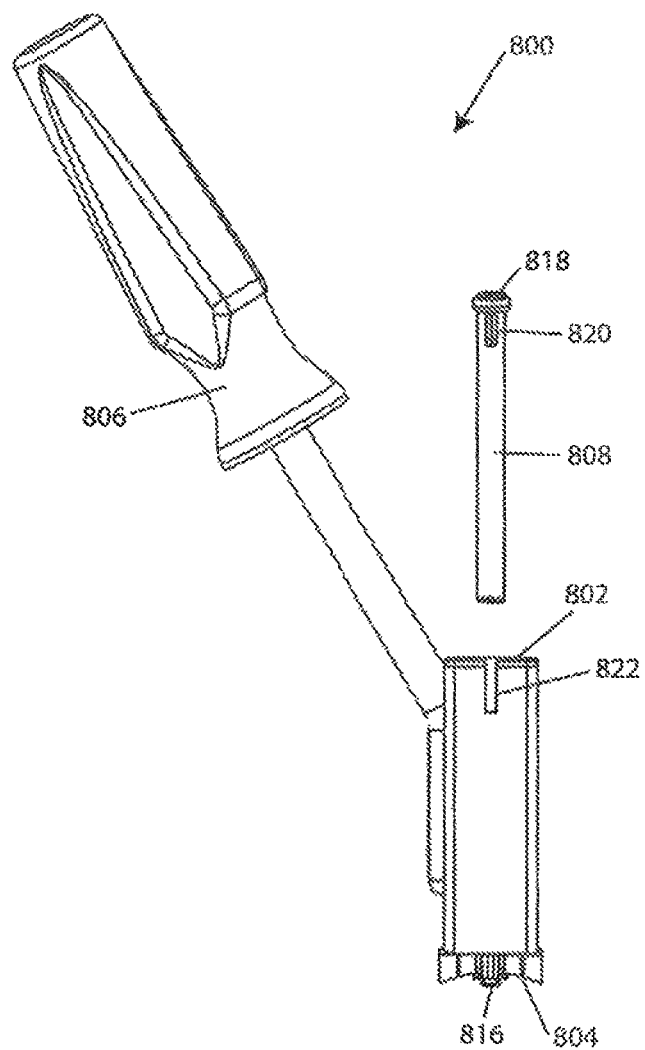
FIGS. 13A-13G show an exemplary instrument guide tool for use with the implantable bone plate of FIGS. 11A-11E.
Figure 13B:
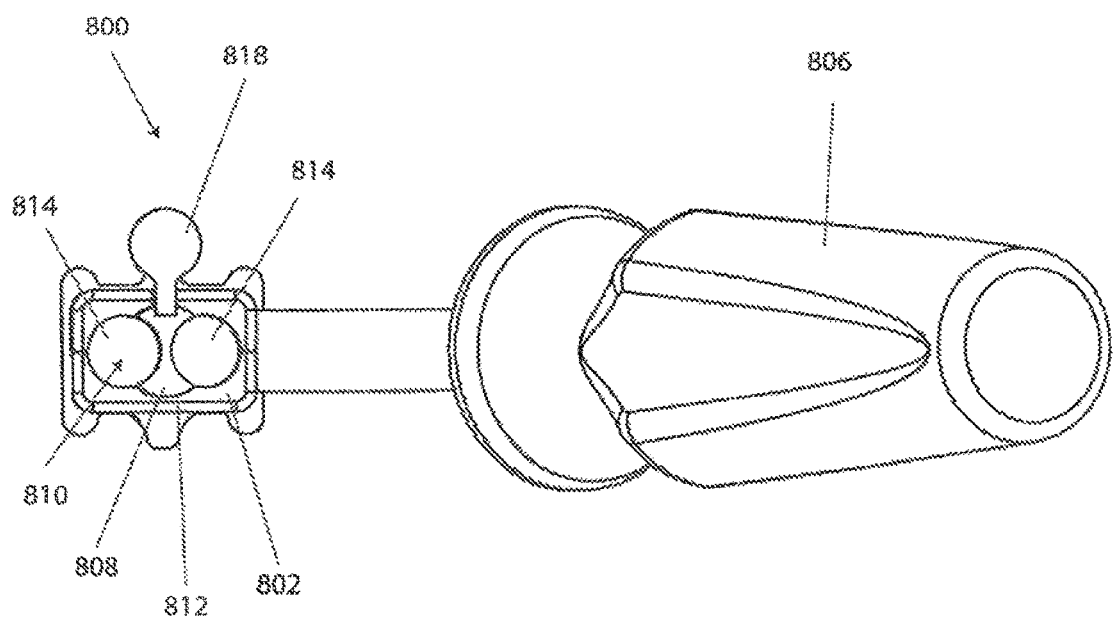
Figure 13C:
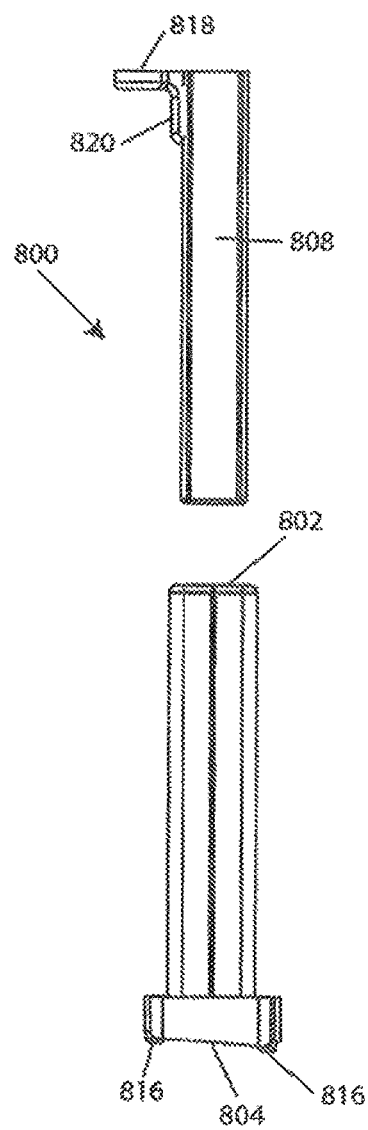
Figure 13D:
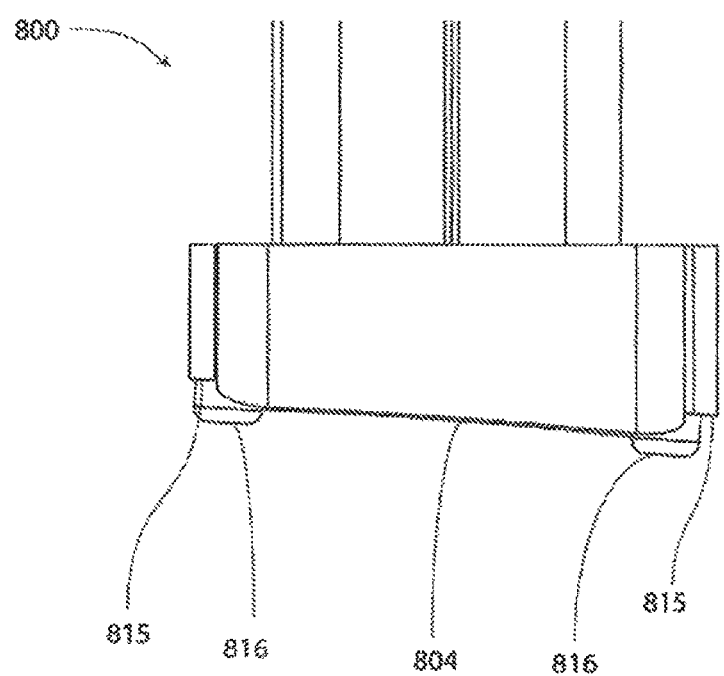
Figure 13E:
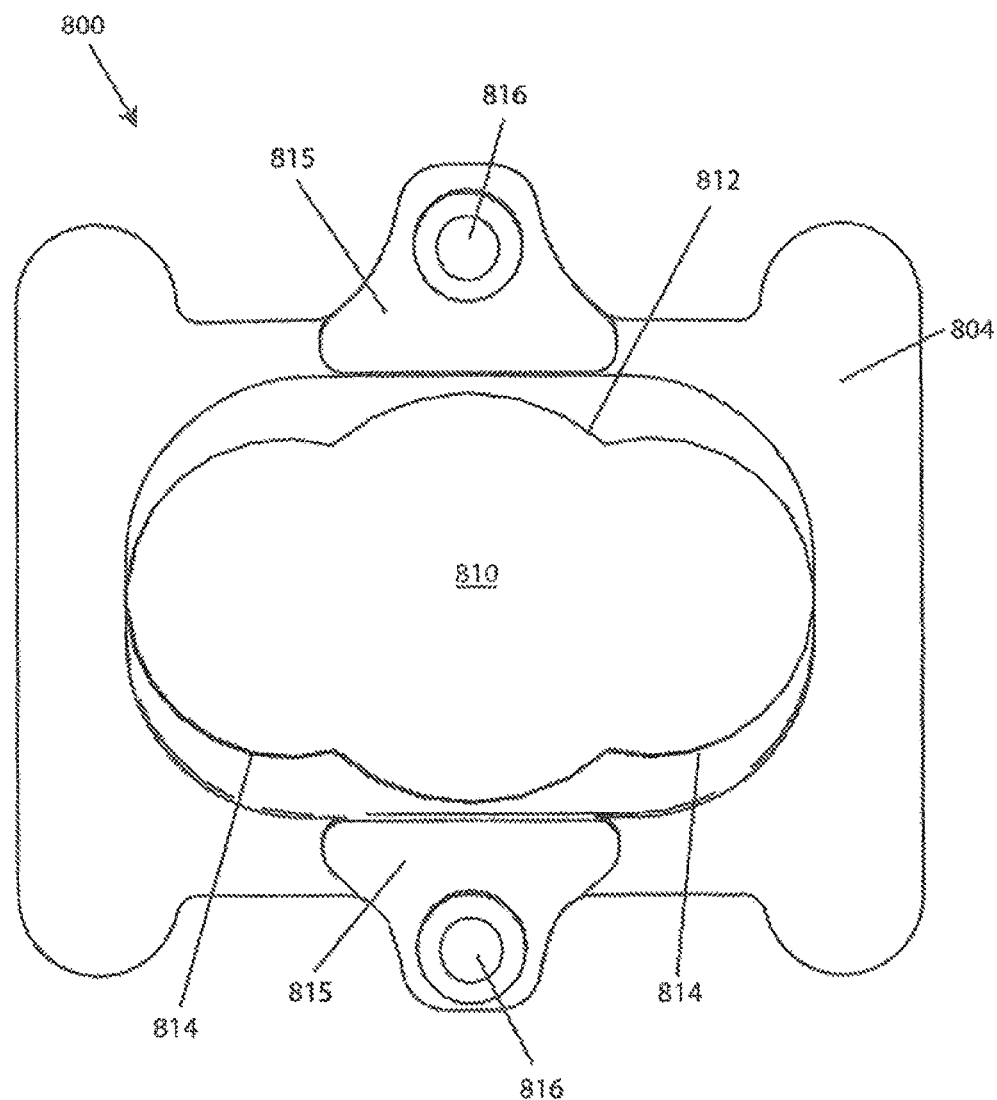

As best seen in FIG. 13E, instrument guide 800 includes a tri-lobe lumen 810 extending therethrough from the proximal end 802 to the distal end 804. Lumen 810 includes a central bore 812 overlapping two lateral bores 814.

The distal end 804 of guide 800 is configured to mate with the anterior side 704 of vertebral frame 700. As best seen in FIGS. 13A and 13G, distal end 804 may be curved in the mediolateral direction to match the curvature of frame 700, As best seen in FIGS. 13C and 13D, the body (and therefore lumen 810) of guide 800 may be angled in the caudal direction relative to the distal end 804. In some embodiments, this angle is about 3 degrees to correspond with the angle of the intervertebral space relative to the anterior surface of vertebral bodies in the cervical spine. When guide 800 is coupled to frame 700, lumen 810 of guide 800 lines up with operating aperture 716 of frame 700.

Figure 13F:
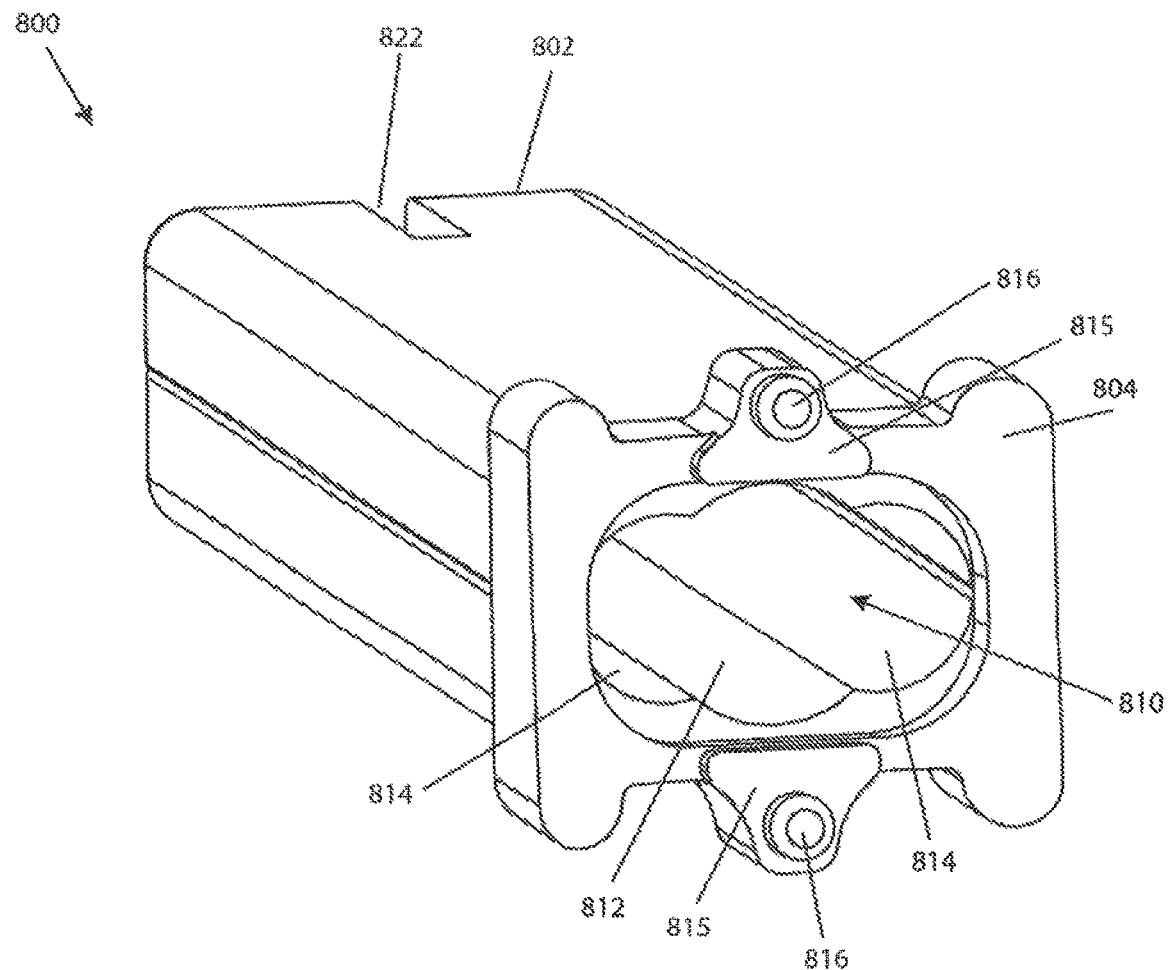
Figure 13G:
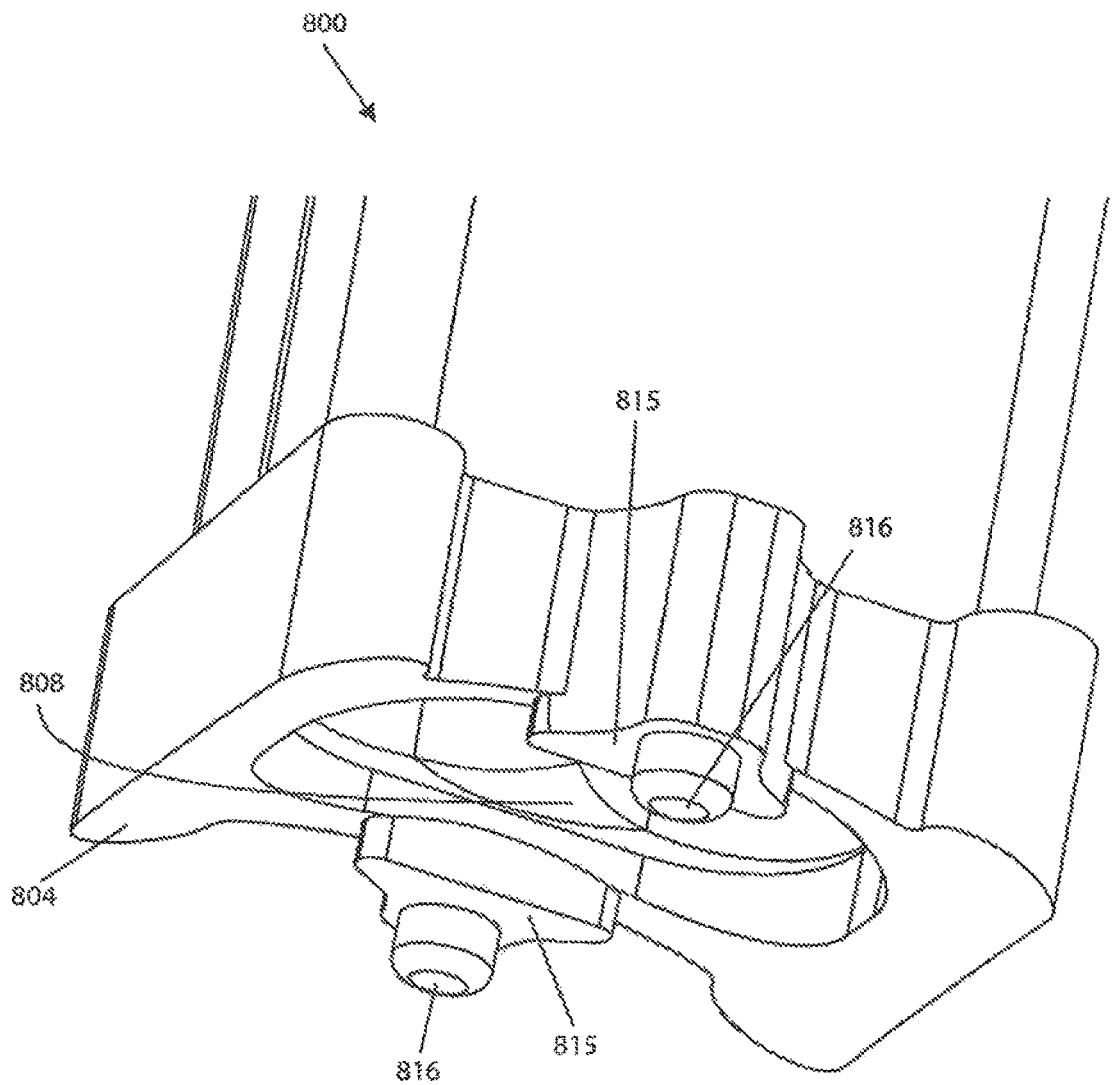

Referring to FIGS. 13E-13G, features of the distal end 804 of guide 800 are shown. Registration surfaces 815 are provided on guide 800 for contacting reference surfaces 718 of frame 700, shown in FIGS. 11A and 11B. Bosses 816 may be provided on registration surfaces 815 as shown for engaging holes 720 in reference surfaces 718. The above features cooperate to accurately align features on guide 800 that may be critical, such a lumen 810 and proximal surface 802, with features on frame 700 and underlying anatomical features.

Insert 808 has rounded sides corresponding with central bore 812, as best seen in FIG. 13B. When optional insert 808 in temporarily placed in central bore 812 in this exemplary embodiment, the tri-lobe lumen of guide 800 is converted into two individual lateral bores 814 as shown. Insert 808 may be provided with a handle 818. In this embodiment, handle 818 includes an elongated rib 820 which is received in slot 822 in the guide body, as shown in FIG. 13A. This arrangement allows insert 808 to be keyed with guide 800 in only one orientation. Insert handle 818 may also be provided with a direction indicator, such as an arrow pointing to the patient's feet and corresponding indicia, as shown in MG. 13B.

Figure 14A:
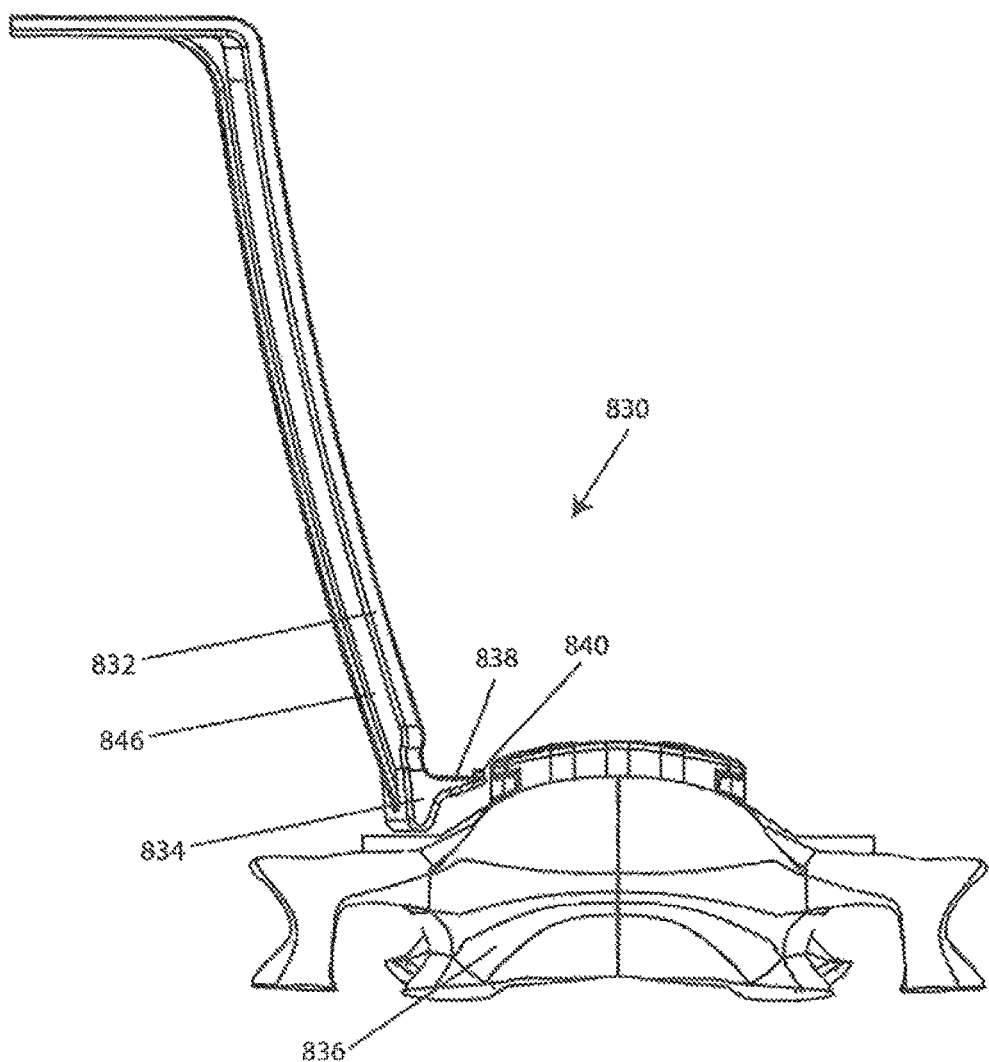
FIGS. 14A-14C show an exemplary tissue retractor being used with an implantable bone plate mounted on a vertebral body.
Figure 14B:
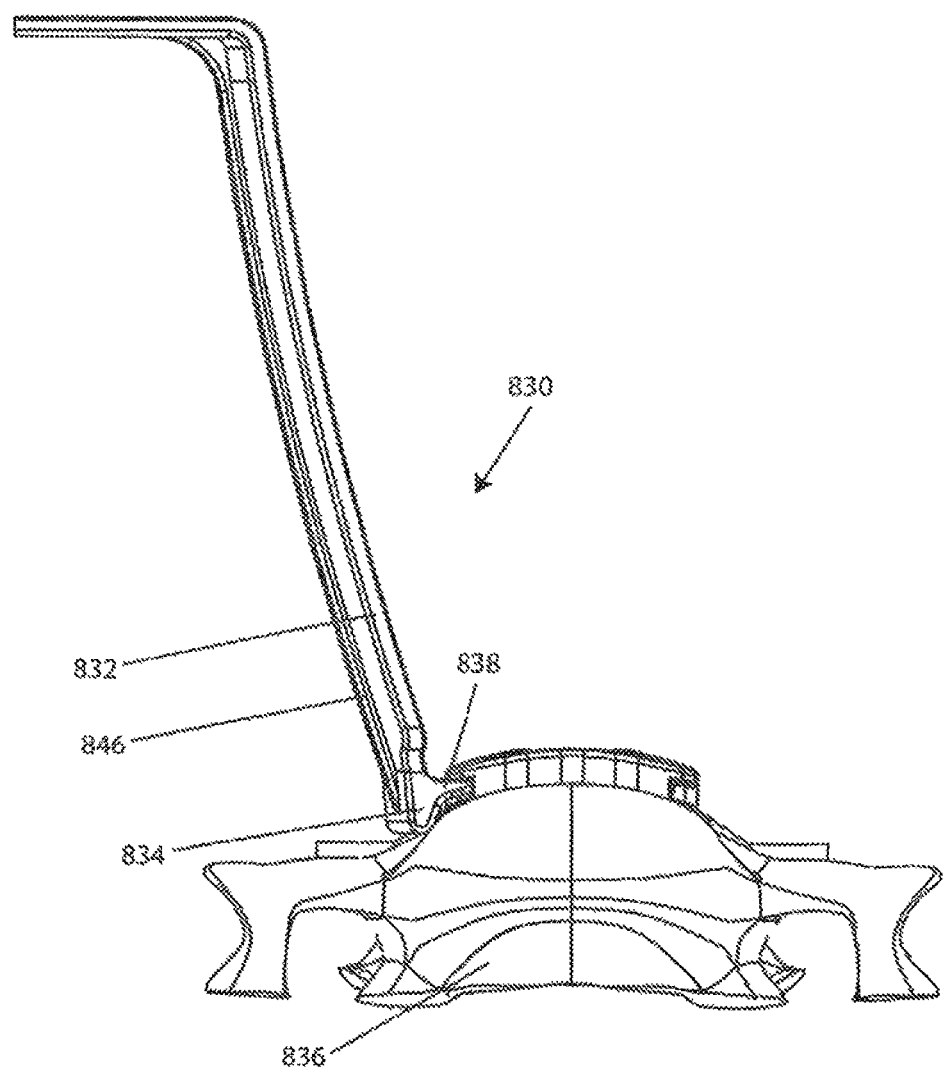
Figure 14C:
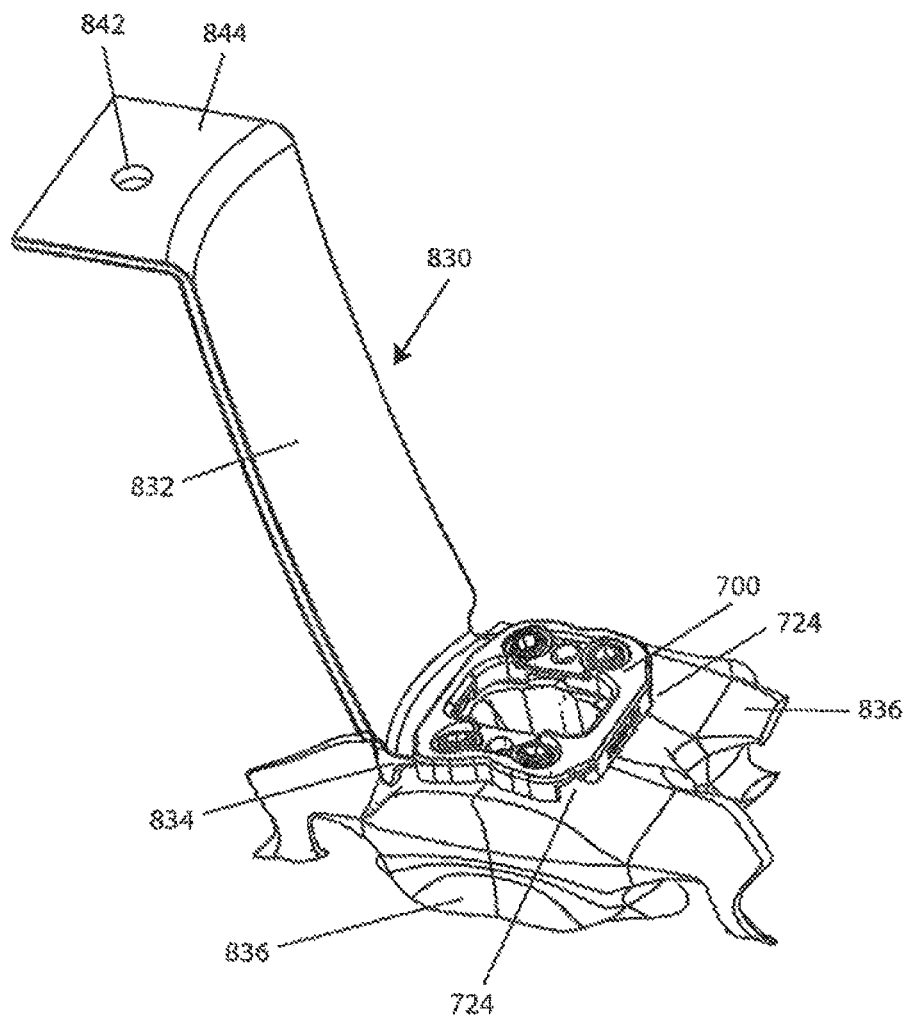

Referring to FIGS. 14A-14C, an exemplary soft tissue retractor 830 constructed according to aspects of the invention is shown. One or more retractors 830 may be used in conjunction with intervertebral frame 700 after it is installed on one or more vertebrae to retract soft tissue away from frame 700 during a surgical procedure. Retractor 830 includes a blade 832. The distal end of blade 832 may be provided with a fulcrum 834 for contacting vertebral body 836, and a pair of tongues 838 for engaging with previously described recesses 724 in frame 700. The distal ends of tongues 838 may be provided with protrusions 840 projecting in the anterior direction for engaging with previously described pockets 726 in recesses 724. As shown in FIG. 14A, the distal end of blade 832 may be placed adjacent to frame 700, and then tongues 838 may be inserted into recesses 724 as shown in FIG. 14B. The proximal end of blade 832 may be provided with a feature, such as hole 842 in flange 844, for attaching a handle or spreading device (not shown) to urge the proximal end of blade 832 in a lateral direction against soft tissue adjacent to frame 700. A single spreading device may be attached between a pair of opposing retractors 830 (only one shown for clarity) to keep them spread apart. Blade(s) 830 may be curved, as shown in FIG. 14C, and/or may be provided with a longitudinal rib 846, as shown in FIGS. 14A and 14B, for increased rigidity.

Referring to FIGS. 15A-15C, an exemplary interbody repair implant 850 constructed according to aspects of the invention is shown. In this embodiment, implant 850 has an elongated tri-lobe shape which includes a central cylindrical portion 852 and two lateral cylindrical portions 854 which overlap with the central portion 852. Cylindrical portions 852 and 854 correspond with central bore 812 and overlapping lateral bores 814, respectively, of instrument guide 800. Implant 850 may be provided with one or more graft windows 856 for receiving cages containing bone material and/or for promoting bony ingrowth between the vertebrae and implant 850. One or both ends of implant 850 may be provided with a central hole 858 and two lateral holes 860, or other suitable features, for engaging implant insertion instrumentation. In this exemplary embodiment, central hole 858 is threaded and lateral holes 860 are configured for sliding engagement with features on the instrumentation. One or more radio markers 862 may be provided on implant 850, such as shown in the four corners of the implant in FIGS. 15B and 15C. Radio markers 862 may comprise titanium, tantalum or other biocompatible, radio-opaque material(s) to assist in determining the position of implant 850 in imaging.

In some embodiments, the tri-lobe configuration of implant 850 helps resist undesirable axial rotation between axial vertebrae. In some embodiments this configuration minimizes the tissue that is removed from the adjacent vertebrae as compared with a rectangular or other shape implant. In some embodiments surgeons are provided with implants that are either 11 mm or 15 mm long, and 15 mm or 18 mm wide.

In some embodiments implant 850 is made of PEEK. Since PEEK is radiolucent, bony ingrowth into the implant may be monitored with imaging during the healing process. In other embodiments, the implant comprises titanium and/or stainless steel.

Referring to FIGS. 16A-16B, an exemplary intervertebral distraction device 870 constructed according to aspects of the invention is shown. Distraction device 870 includes a wedge portion 872 and a head portion 874. In this embodiment, wedge portion 872 includes a first pair of non-parallel surfaces 876, 878, and a second pair of non-parallel surfaces 880, 882. First surfaces 876 and 878 serve as lead-in surfaces when distraction device 870 is being introduced between the endplates of adjacent vertebral bodies. Second surfaces 880 and 882 serve to orient the vertebral endplates at a predetermined distraction distance h and lordosis angle α.

Head portion 874 of distraction device 870 may have a height H in a craniocaudal direction larger than the height F of wedge portion 872 in the same craniocaudal direction, as shown in FIG. 16C. This prevents head portion 874 from entering the intervertebral space between the adjacent vertebrae. In other words, shoulders 884 serve as a depth stop by contacting the anterior surfaces of the vertebrae, as will be subsequently described in more detail. In some embodiments, the surgical team may be provided with a kit comprising distraction devices each having the same head height H. and different wedge portion heights h, such as 4, 5, 6, 7, and 8 ram. As can also be seen in FIG. 16C, wedge portion 872 has a predetermined length L, which in some embodiments is 10 mm. Wedge portion 872 has a longitudinal axis that in some embodiments is not perpendicular to shoulders 884 in this exemplary embodiment, the angle of offset between wedge portion 872 and head portion 874 matches the previously described angle of the body (and therefore lumen 810 of guide 800 relative to the distal end 804. In some embodiments, this angle is about 3 degrees to correspond with the angle of the intervertebral space relative to the anterior surface of vertebral bodies in the cervical spine.

Head portion 874 of distraction device 870 may be provided with a central hole 858 and two lateral holes 860, or other suitable features, for engaging implant insertion instrumentation as previously described in relation to interbody repair implant 850.

Figure 17A:
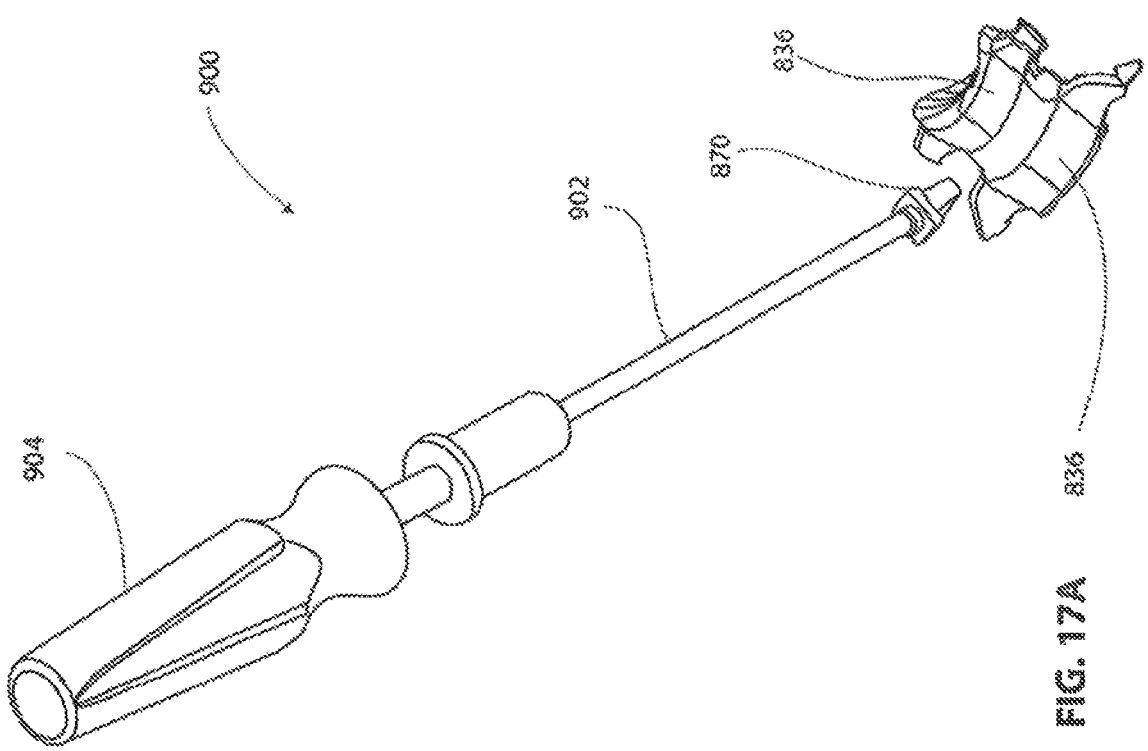
FIGS. 17A-17X show an exemplary spinal fusion surgical procedure.

Referring to FIGS. 17A-17X, an exemplary spinal fusion surgical procedure using the previously described components is depicted according to aspects of the invention.

FIG. 17A shows an exemplary distraction device 870 temporarily attached to an insertion instrument 900 and about to be inserted between adjacent vertebrae 836, 836. Insertion instrument 900 may include a separate shaft portion 902 removably attached to a handle 904, such as a handle having a standard "AO" interface.

Figure 17B:
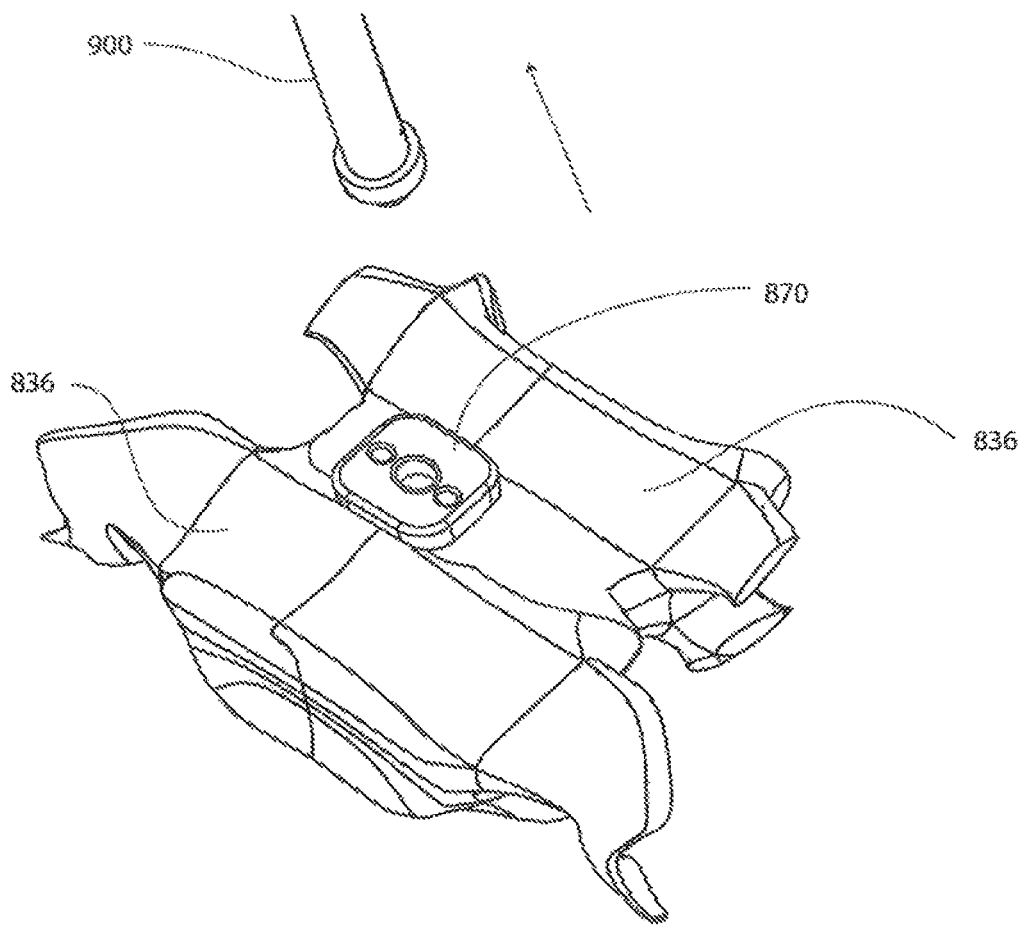

FIG. 17B shows distraction device 870 inserted between adjacent vertebrae 836, 836 as the insertion instrument is being removed.

FIG. 17C shows a cross-section of distraction device 870 inserted between adjacent vertebrae 836, 836 after the insertion instrument has been removed.

Figure 17D:
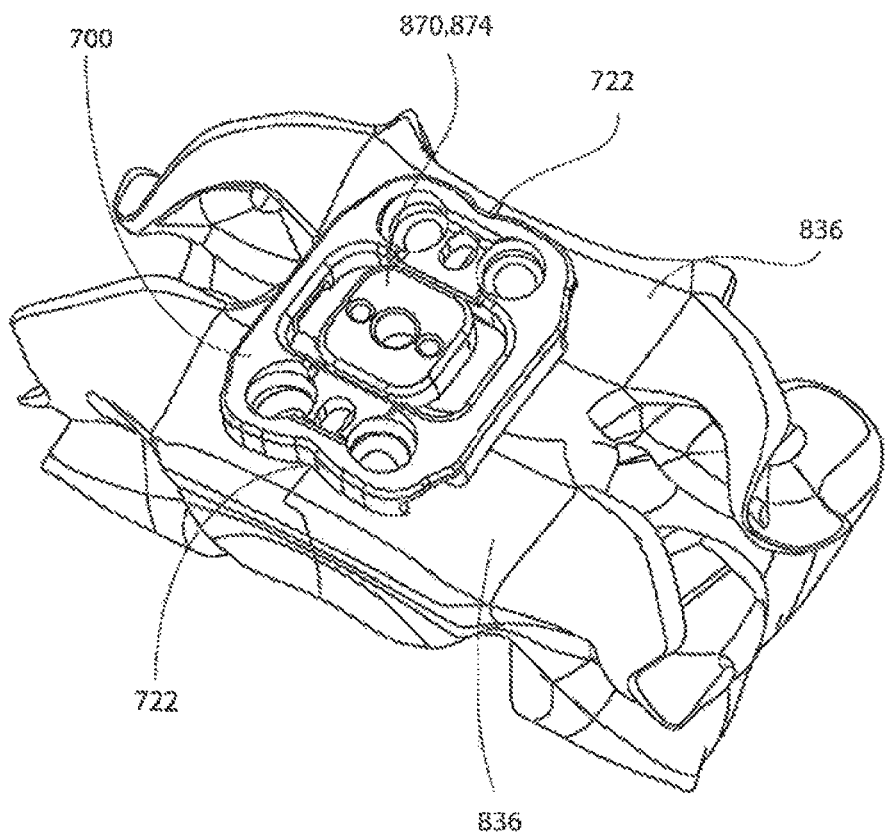

FIG. 17D shows intervertebral frame 700 placed on adjacent vertebrae 836, 836 over distraction device 870. Operating aperture 716 through frame 700 can be configured with a craniocaudal height just nominally larger than the craniocaudal height of head 874 of distraction device 870. This arrangement allows a surgeon to properly center frame 700 over the intervertebral space 906 between adjacent vertebrae 836, 836 merely by placing frame 700 over head 874. As previously described, indents 722 at the top and bottom of frame 700 can provide assistance to the surgeon when centering frame 700 in the mediolateral direction.

Figure 17E:
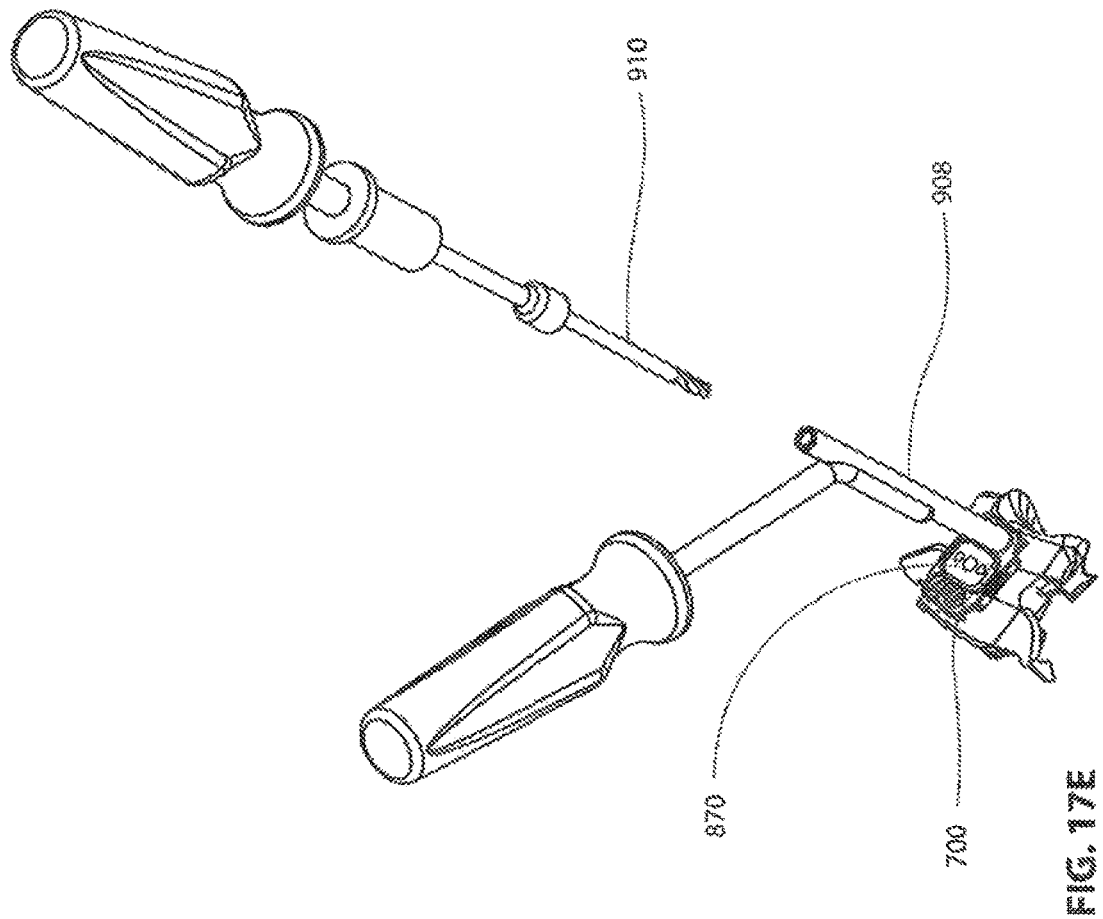

FIG. 17E shows a drill guide 908 placed over one of the screw holes 702 in frame 700 for guiding optional drill 910 to create holes in vertebrae 836 for receiving bone screws. A reamer, tap and/or other bone cutting instruments may also be optionally used to prepare screw holes. In some embodiments, self drilling and/or self-tapping screws may be used. The screws may be installed by hand or with a screw guide similar to drill guide 908. The screws may be fixed angle and/or variable angle. In some embodiments, the screws have an aggressive thread. In some embodiments a 4.0 mm standard size screw is used. In some embodiments a 4.5 mm recovery screw is used.

Figure 17F:
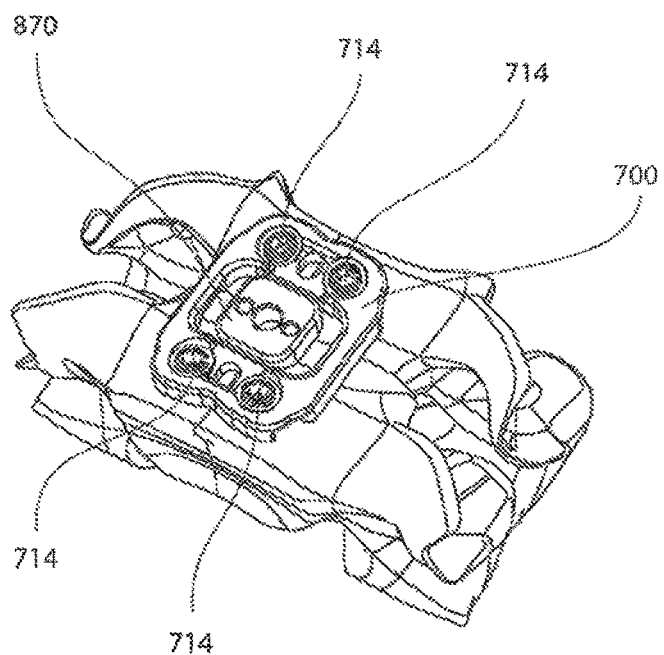

FIG. 17F shows frame 700 secured to adjacent vertebrae 836, 836 with four screws 712.

Figure 17G:
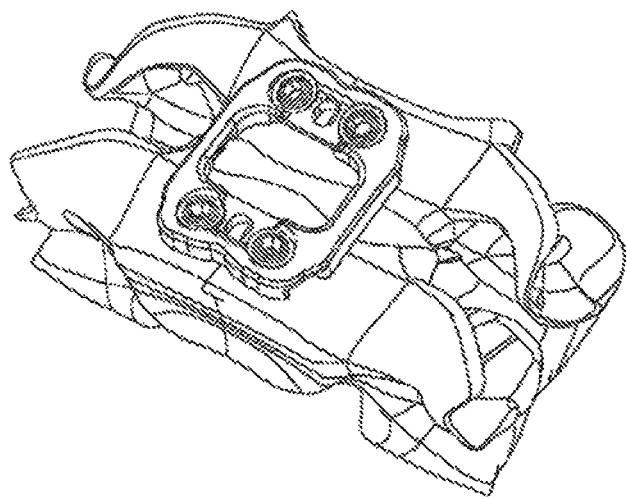

FIG. 17G shows frame 700 secured to adjacent vertebrae 836, 836 after distraction device 870 has been removed. Distraction and lordotic angle is now permanently set and locked in place by frame 700.

Figure 17H:
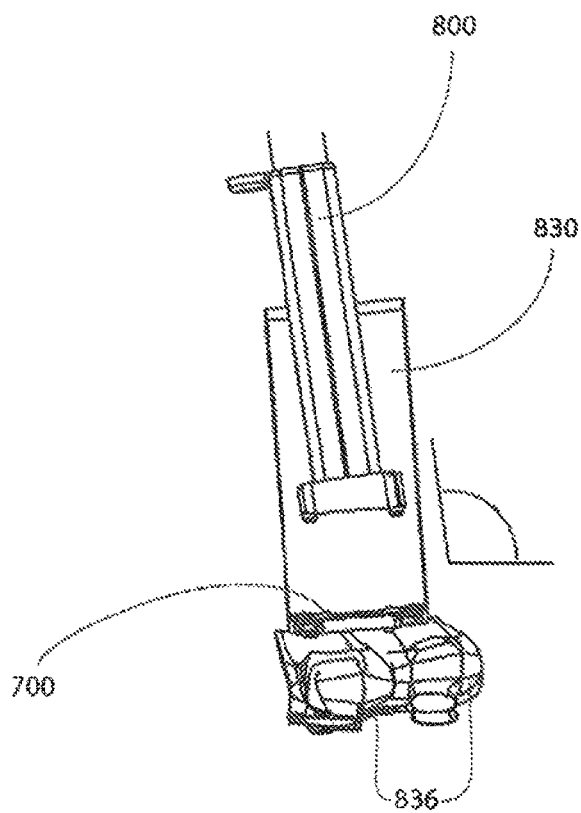

FIG. 17H shows frame 700 secured to adjacent vertebrae 836, 836 with retractor 830 attached and instrument guide 800 being lowered into position on top of frame 700.

Figure 17I:
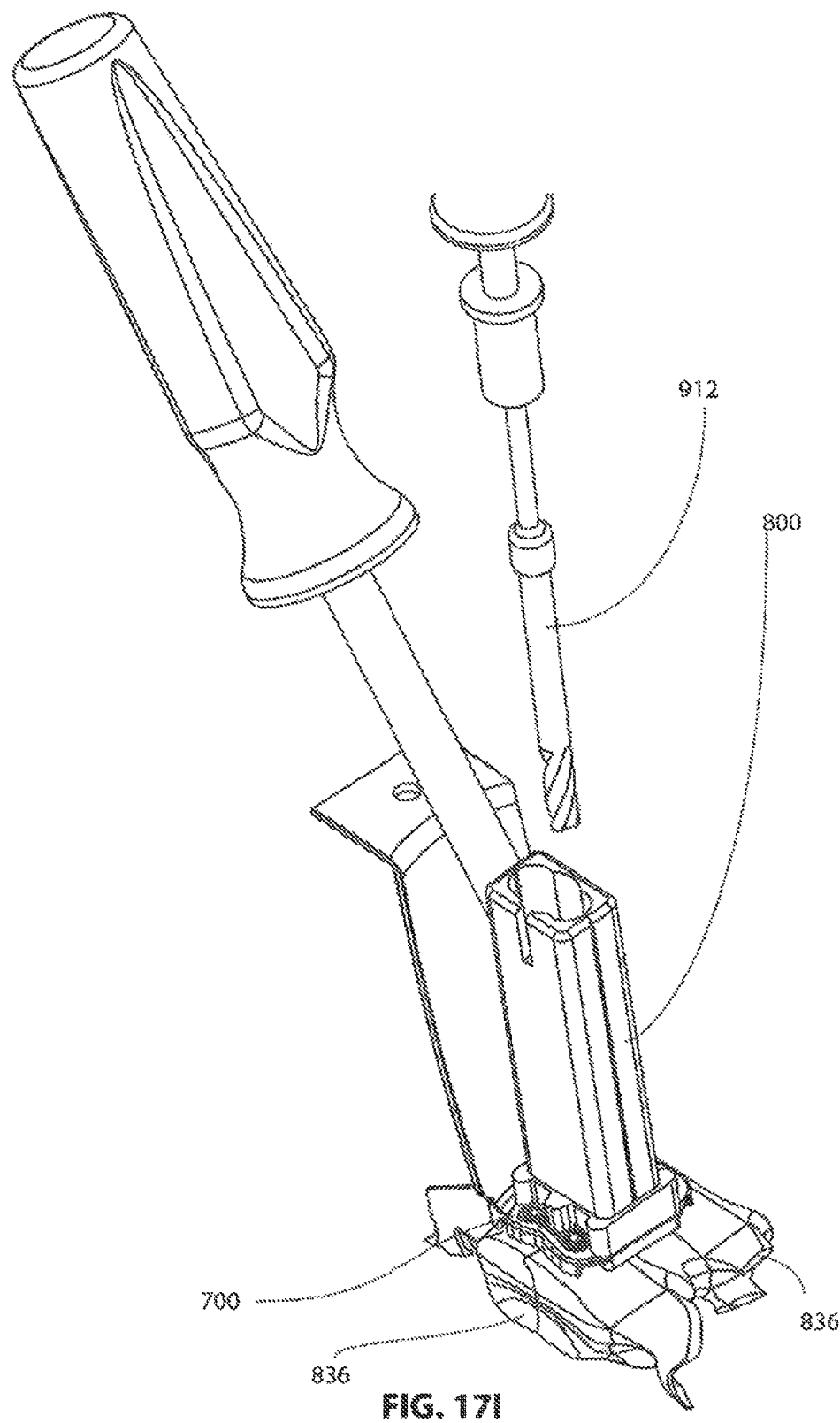

FIG. 17I shows instrument guide 800 in position on top of frame 700 and a large drill 912 being inserted into central bore 812 of guide 800 to begin preparing the intervertebral space between vertebrae 836, 836 by removing the disc and/or end plate material. A drill, trephine, reamer, other bone cutting tool, or a combination thereof may be used to prepare the intervertebral space. Standard sizes of 6, 7, 8 or 9 mm can all be produced using the same instrument guide. In some embodiments a custom cutter is used with cutting sides and face. In some embodiments, the natural bone material being removed is collected from the cutting tool(s) and packed into the interbody implant before it is implanted in the patient.

Figure 17J:
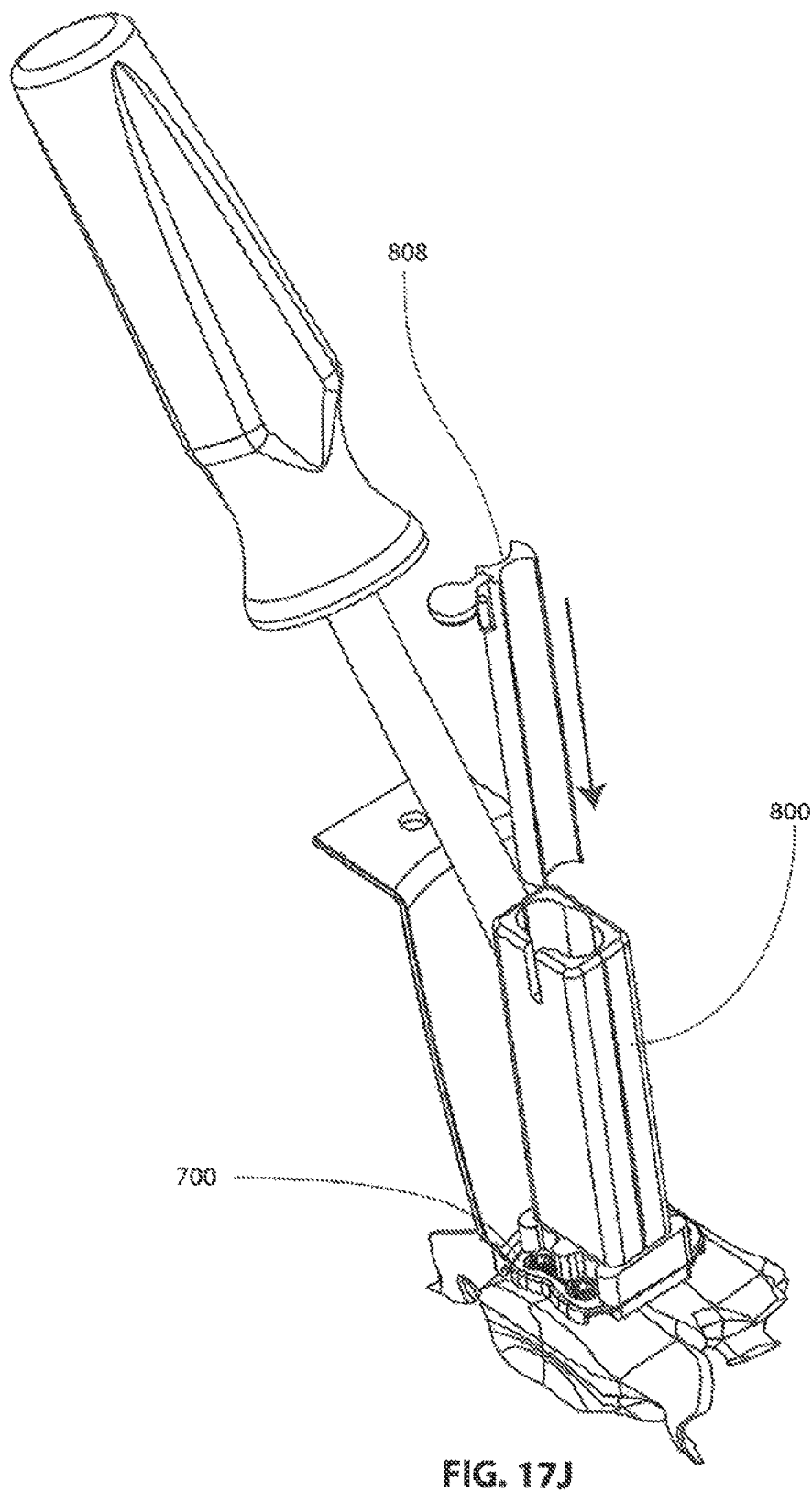

FIG. 17J shows instrument guide 800 in position on top of frame 700 and guide insert 808 being inserted into central bore 812 of guide 800.

Figure 17K:
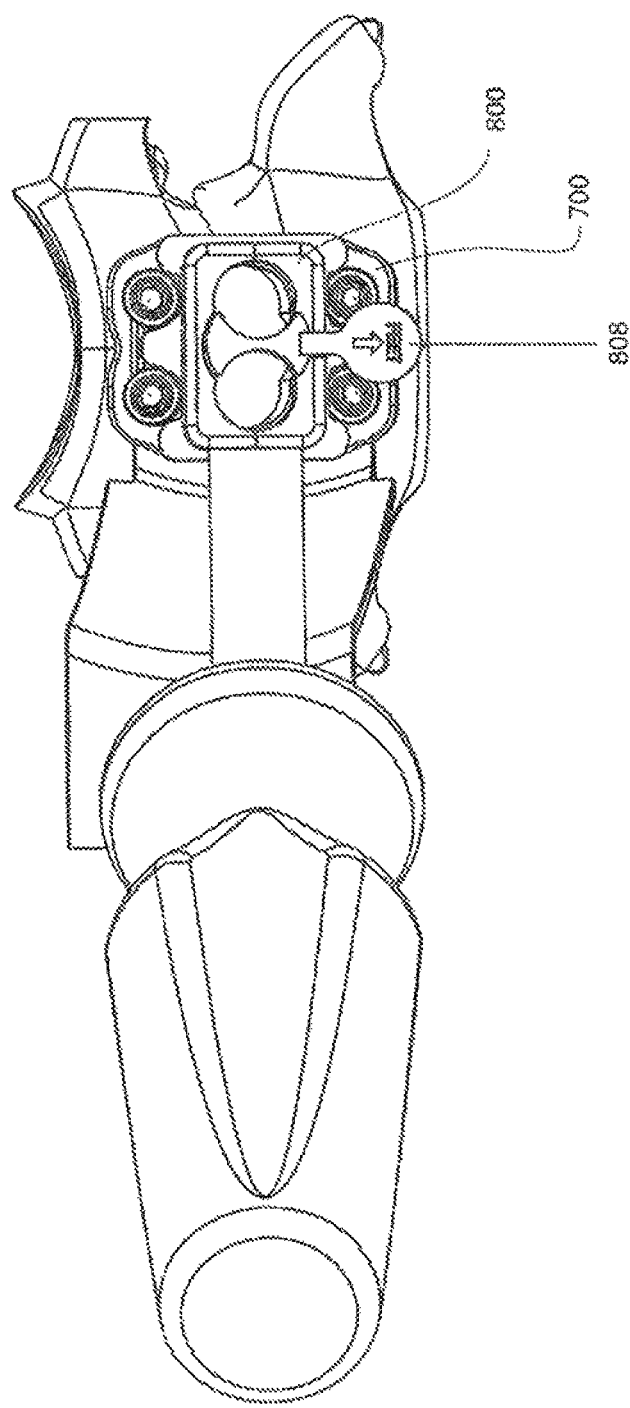

FIG. 17K shows instrument guide 800 in position on top of frame 700 and guide insert 808 fully inserted into central bore 812 of guide 800.

Figure 17L:
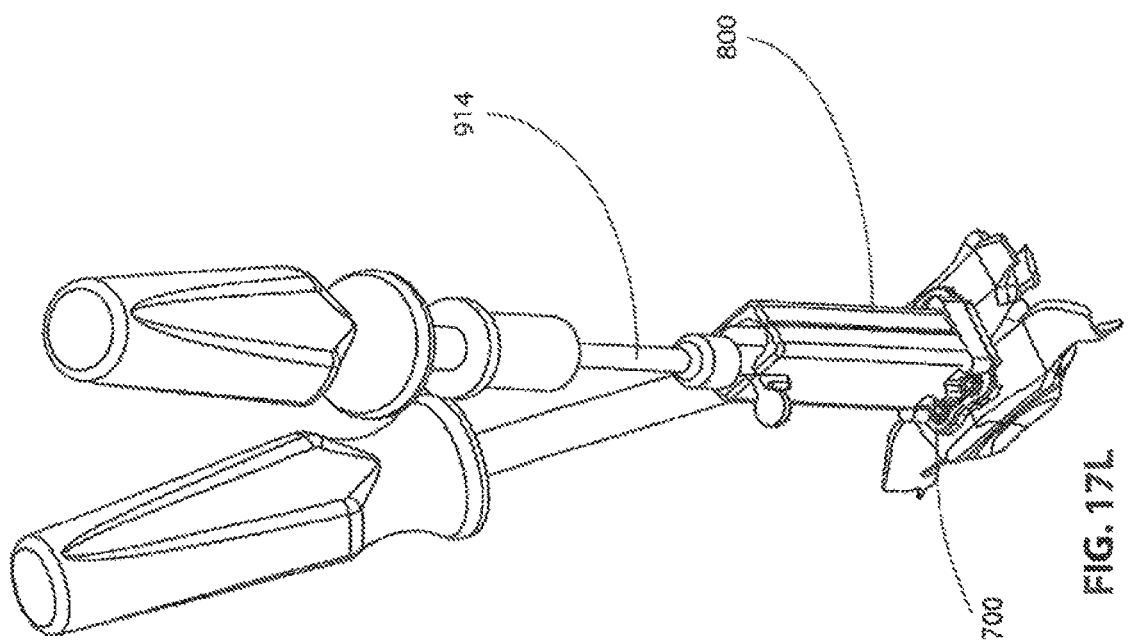

FIG. 17L shows instrument guide 800 in position on top of frame 700 and a small drill 914 being inserted into one of the lateral bores 814 of guide 800 to further prepare the intervertebral space between vertebrae 836, 836. As with the central bore, a drill, trephine, reamer, other bone cutting tool, or a combination thereof may be used in the lateral bores, and the harvested bone tissue may be packed into the implant. In some embodiments, the lateral bores are prepared without the use of an insert 808, and/or the lateral bores may be prepared before or after the central bore.

Figure 17M:
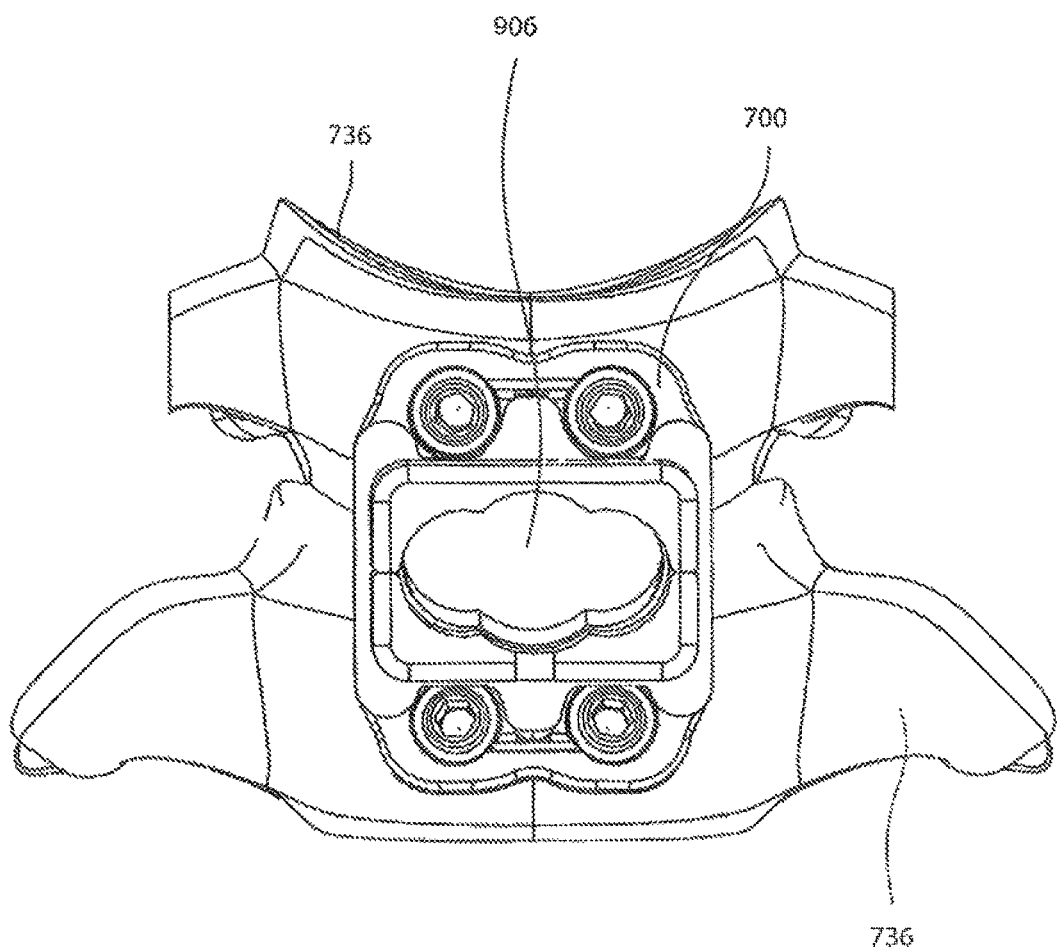

FIG. 17M shows frame 700 secured to adjacent vertebrae 836, 836 with the intervertebral space 906 prepared for receiving a tri-lobe intervertebral implant.

Figure 17N:
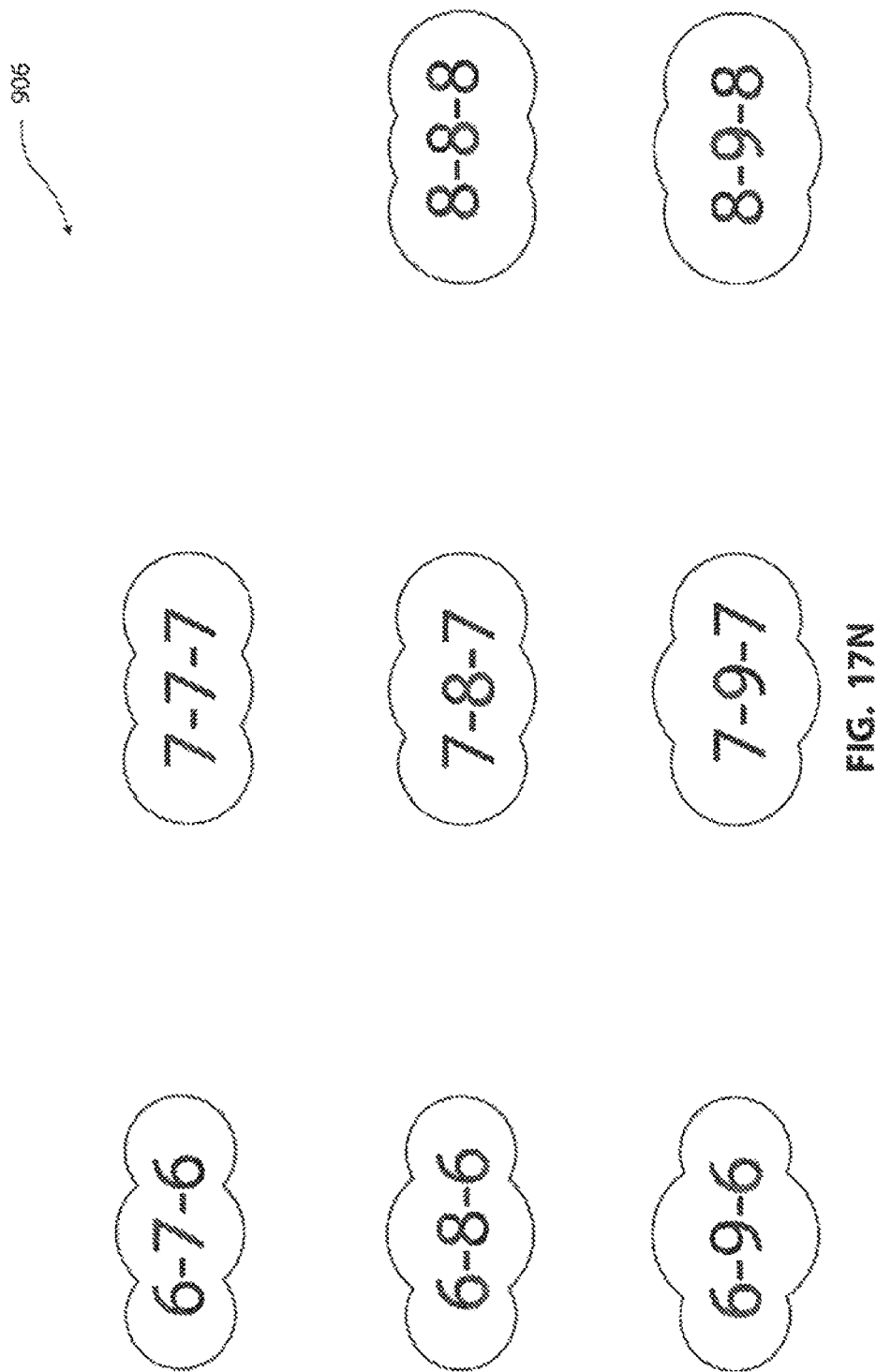

FIG. 17N depicts the nominal diameters (in millimeters) of the central and lateral bores for preparing the intervertebral space in various exemplary embodiments. In some embodiments, a variety of implant and guide configurations are made available to the surgical team in a single kit. Each configuration may have the same overall width. In other words, the distance between the outer circumferences of the lateral bores remains fixed across multiple configurations rather than the distance between the centers of the axial bores. Lobe sizes may be surgeon selected based on physiology and disk condition. Standard kerrisons and curettes may be used through the channel.

In some embodiments, the intervertebral space 906 is configured to be nominally smaller than the associated interbody implant, requiring the implant to compressively engage the vertebrae endplates when implanted. This arrangement can provide immediate structural stability of the repaired spine segment and can promote honey ingrowth into the implant.

Figure 17O:
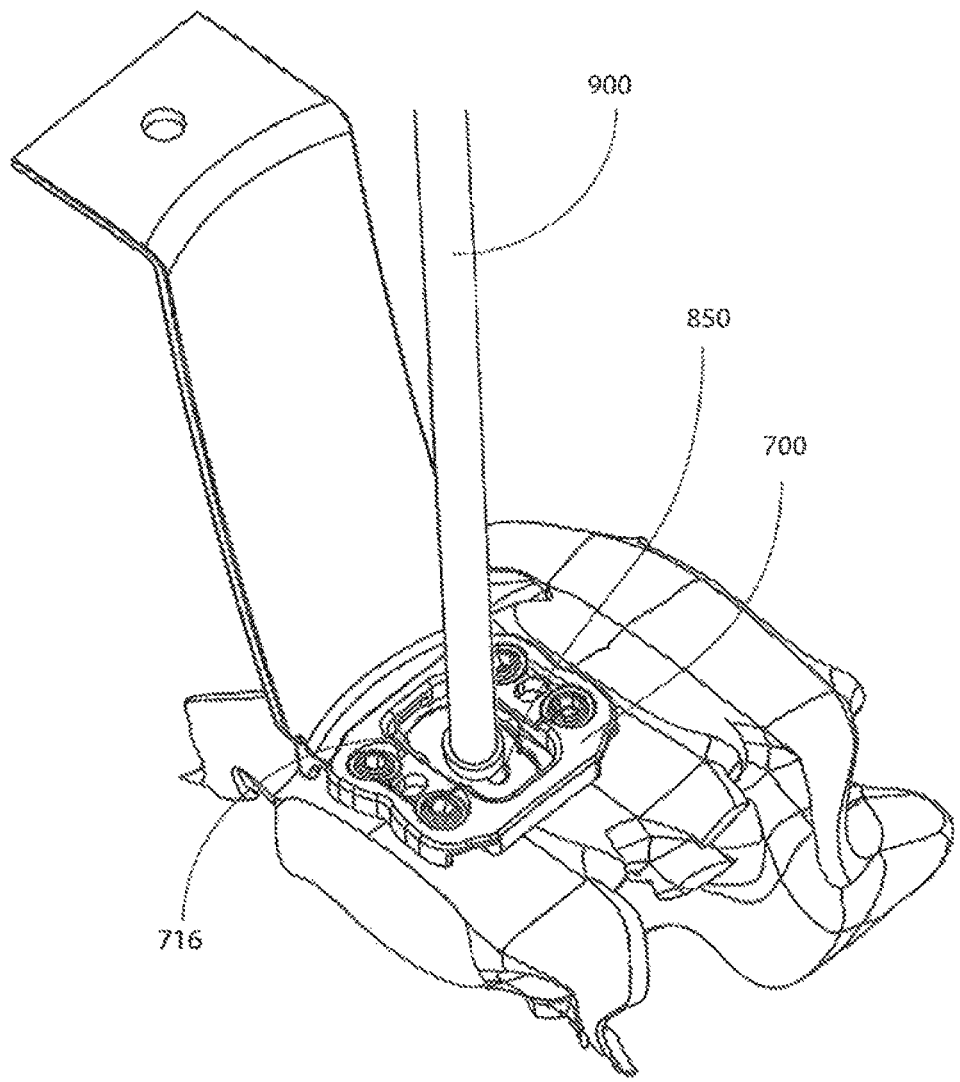

FIG. 17O shows an interbody implant 850 attached to an insertion tool 900 and being inserted through the operating aperture 716 of frame 700 into the prepared intervertebral space. Insertion stops may be provided on the implant and/or insertion tool to limit the depth of insertion of the implant.

Figure 17P:
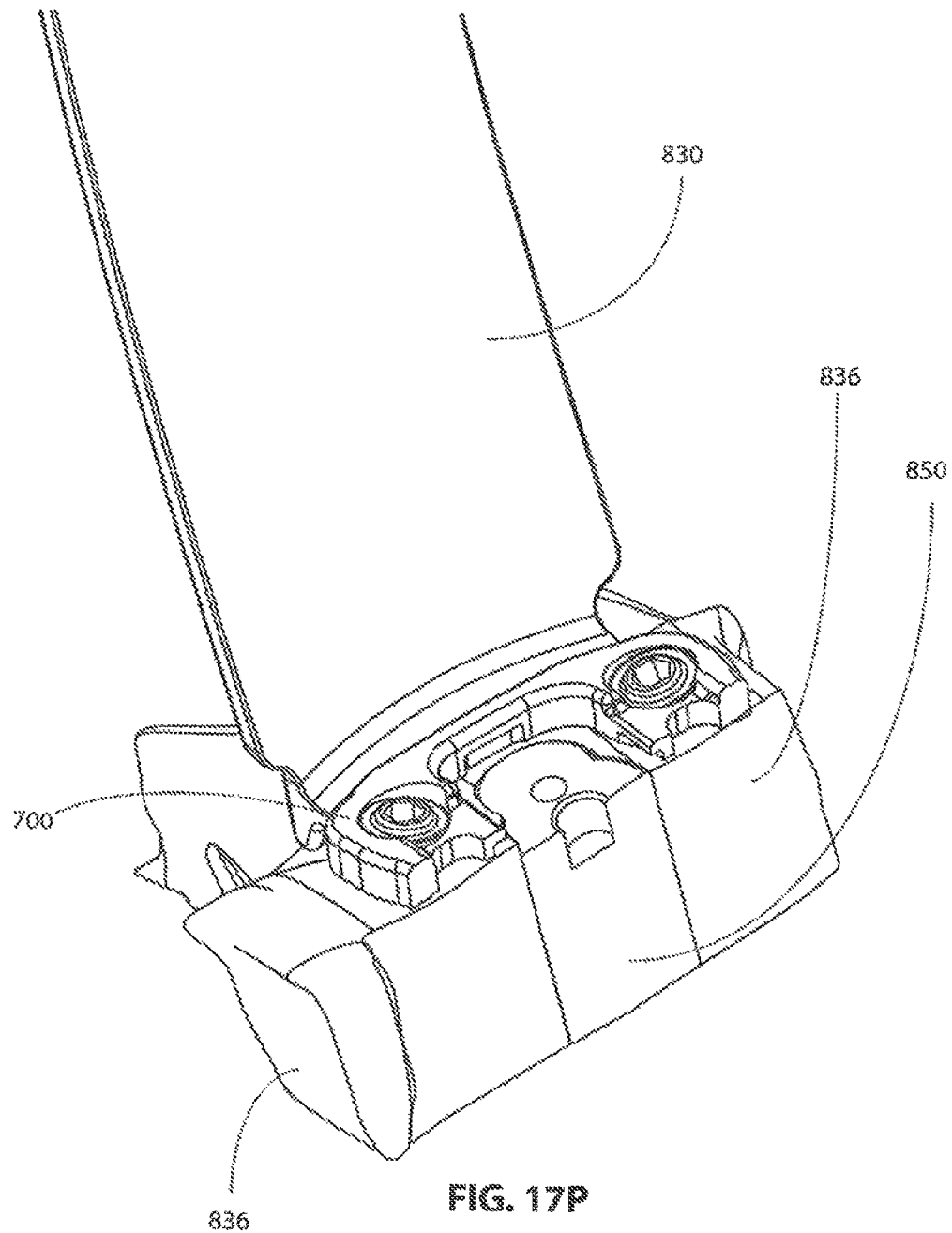

FIG. 17P shows a craniocaudal cross section of interbody implant 850 in place in the prepared intervertebral space.

Figure 17Q:
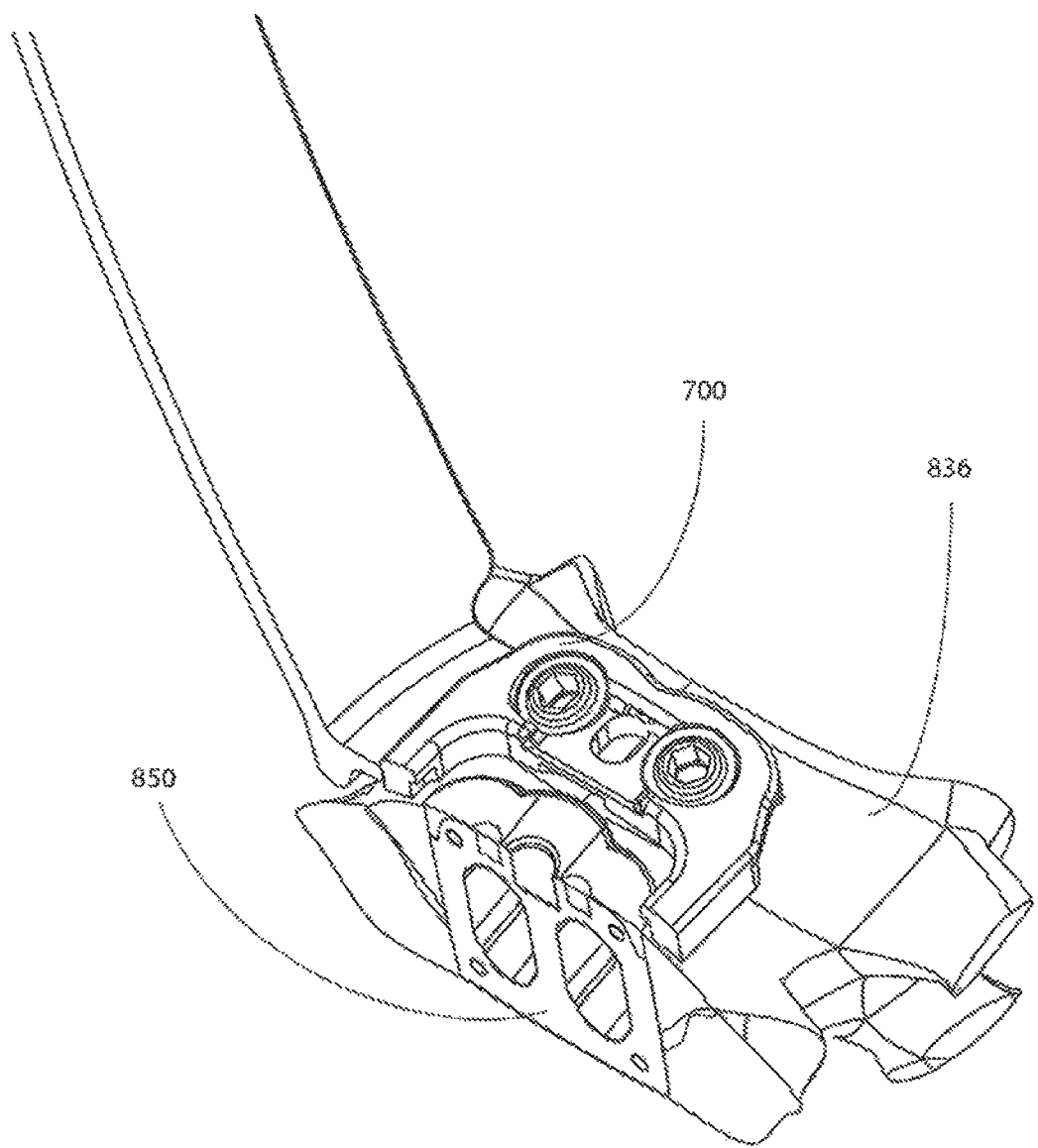

FIG. 17Q shows a mediolateral cross section of interbody implant 850 in place in the prepared intervertebral space.

Figure 17R:
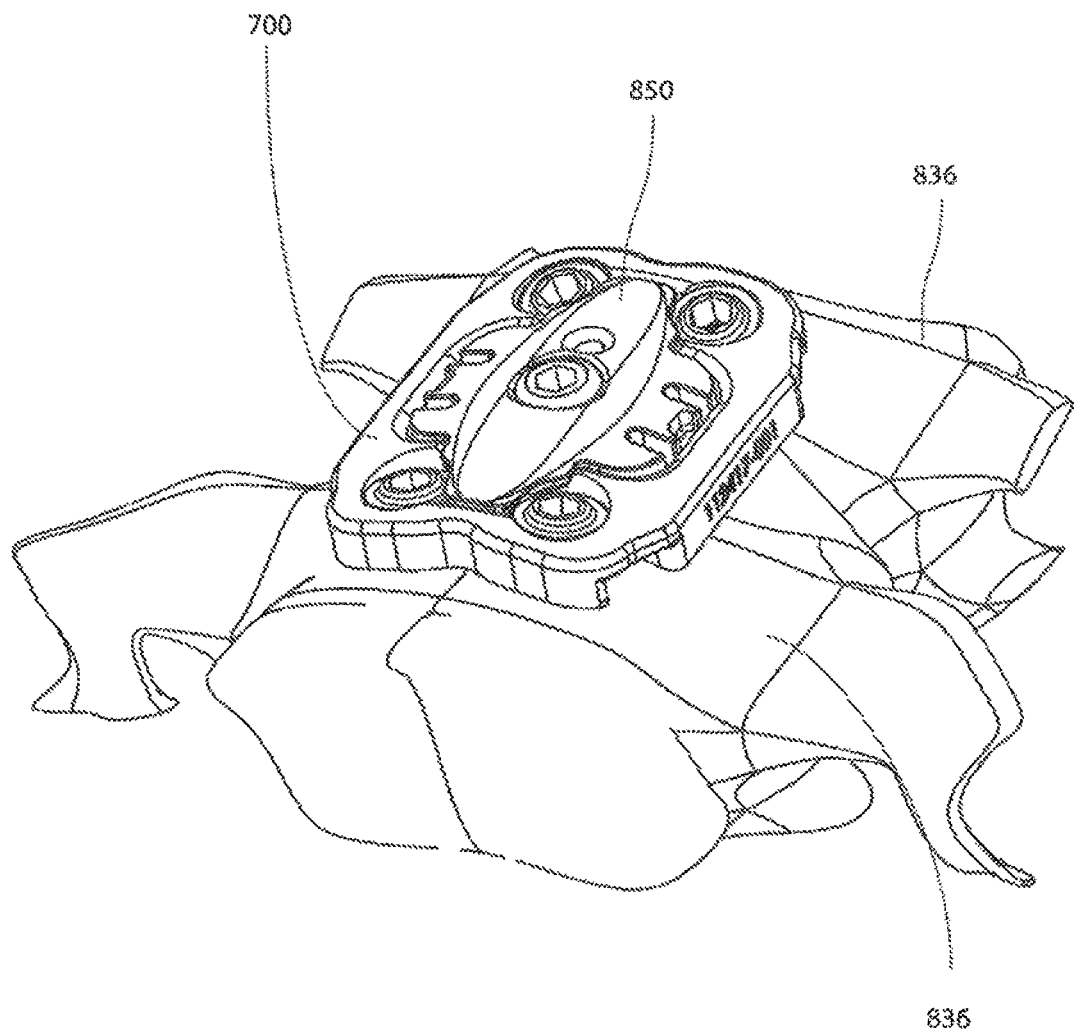

FIG. 17R shows cover plate 750 in position over frame 700.

Figure 17S:
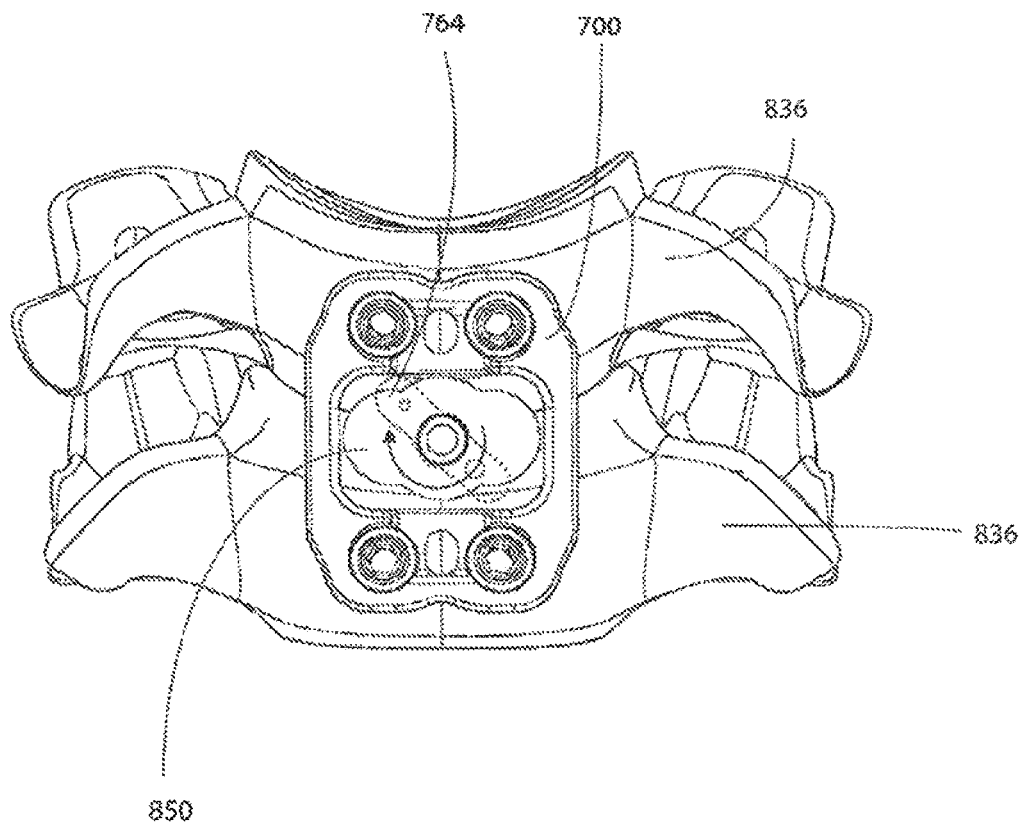

FIG. 17S depicts locking arm 764 of cover plate 750 in the unlocked position and moving towards the locked position.

Figure 17T:
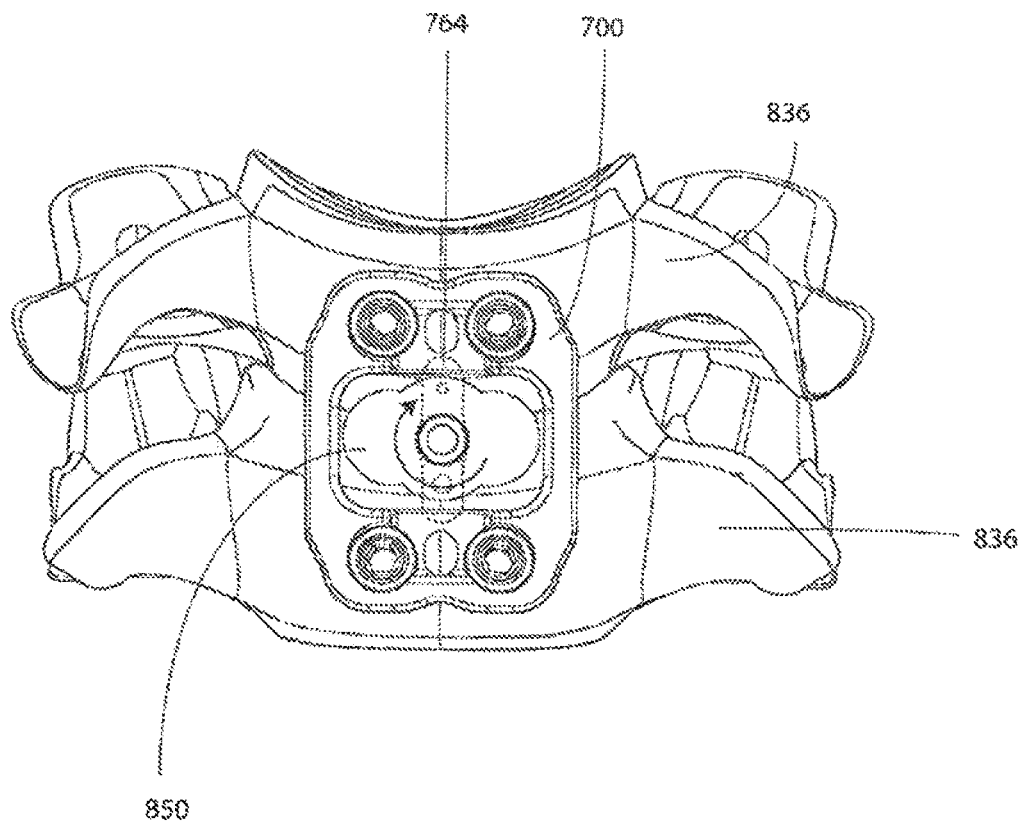

FIG. 17T depicts locking arm 764 of cover plate 750 in the locked position.

FIG. 17U shows an oblique posterior view of a craniocaudal cross-section of cover plate 750 coupled to frame 700 with locking arm 764 in the locked position.

FIG. 17V shows an oblique anterior view of a craniocaudal cross-section of cover plate 750 coupled to frame 700 mounted on adjacent vertebrae 736, 736, with locking arm 764 in the locked position.

Figure 17W:
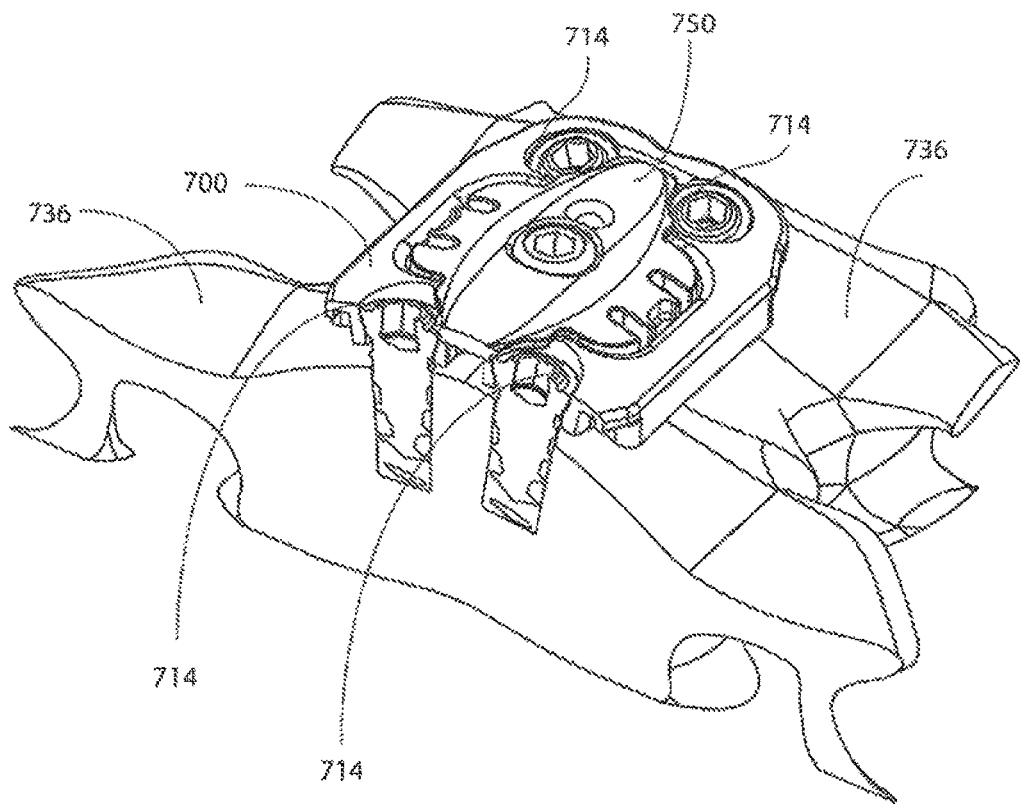

FIG. 17W shows an oblique mediolateral cross-sectional view of a coverplate 750 coupled to frame 700 and covering a portion of screw heads 714.

FIG. 17X shows a mediolateral cross-sectional end view of a coverplate 750 coupled to frame 700 and covering a portion of screw heads 714.

In some embodiments, not every step shown in FIGS. 17A-17X is performed. In some embodiments, additional and/or alternative steps may be performed.

In summary, an exemplary trans-plate cervical decompression and fusion procedure may include at least the following steps:
Anterior incision
Retraction
Distraction and pre-lordosing
Vertebral frame installation over the distraction device
Removal of distraction device
Discectomy and end plate preparation through the frame
Decompression
Implant insertion
Cover implant and lock
Close incision All publications and patent applications mentioned in this specification are herein incorporated by reference to the same extent as if each individual publication or patent application was specifically and individually indicated to be incorporated by reference.

We claim:

1. A method of fusing two or more adjacent vertebral bodies in a portion of a spinal column, the method comprising:
    inserting a distraction device between two adjacent ones of the two or more adjacent vertebral bodies of the spinal column to distract the two adjacent vertebral bodies, the distraction device having a head portion that protrudes from the two adjacent vertebral bodies in an anterior direction;
    centering a vertebral fixation frame relative to the distraction device in a craniocaudal direction by aligning a central aperture of the vertebral fixation frame with the head portion of the inserted distraction device, the vertebral fixation frame configured to contact a surface of each of the two adjacent vertebral bodies and comprising an implantable plate;
    securing the vertebral fixation frame to the distracted two adjacent vertebral bodies over the inserted distraction device in an originally secured position such that the distracted two adjacent vertebral bodies are maintained in a final prescribed spatial relationship after the vertebral fixation frame has been secured;
    after securing the vertebral fixation frame, removing the inserted distraction device from between the distracted two adjacent vertebral bodies through the central aperture of the secured vertebral fixation frame;
    after removing the inserted distraction device, removing vertebral disc material through the central aperture of the secured vertebral fixation frame;
    inserting an interbody fusion implant through the central aperture and into a vertebral interspace formed by the removed vertebral disc material, and
    maintaining the vertebral fixation frame in the originally secured position on the distracted two adjacent vertebral bodies permanently.

2. The method of claim 1, further comprising a step of excising bone material through the central aperture of the secured vertebral fixation frame.

3. The method of claim 2, wherein the step of excising bone material is performed entirely through the central aperture of the secured vertebral fixation frame.

4. The method of claim 1, further comprising installing an interbody implant retention member onto the secured vertebral fixation frame.

5. The method of claim 1, wherein the securing the vertebral fixation frame includes securing the vertebral fixation frame to more than two of the two or more adjacent vertebral bodies.

6. A method of fusing two or more adjacent vertebral bodies in a portion of a spinal column, the method comprising:
    axially distracting two adjacent ones of the two or more adjacent vertebral bodies of the spinal column into a final prescribed spatial relationship using a distraction device placed between the two adjacent vertebral bodies and engaging upon vertebral end plate tissue, the distraction device having a head portion that protrudes from between the two adjacent vertebral bodies in an anterior direction;

centering a vertebral fixation frame relative to the distraction device in a craniocaudal direction by aligning an operating aperture through the vertebral fixation frame with the head portion of the distraction device, the vertebral fixation frame configured to contact a surface of each of the two adjacent vertebral bodies and comprising an implantable plate;

securing the vertebral fixation frame to the distracted two adjacent vertebral bodies over the distraction device in an originally secured position such that the distracted two adjacent vertebral bodies are maintained in their final prescribed spatial relationship after the vertebral fixation frame securing step is complete;

after the vertebral fixation frame securing step is complete, removing the distraction device from between the distracted two adjacent vertebral bodies through the operating aperture in the secured vertebral fixation frame;

after the distraction device removing step, preparing a vertebral interspace to receive an interbody fusion implant by removing vertebral disc material through the operating aperture in the secured vertebral fixation frame, the distracted two adjacent vertebral bodies remaining in their final prescribed spatial relationship during the preparing step;

inserting the interbody fusion implant through the operating aperture and into the prepared vertebral interspace, and maintaining the vertebral fixation frame in its originally secured position on the distracted two adjacent vertebral bodies postoperatively.

7. The method of claim 6, further comprising a step of excising bone material through the operating aperture in the secured vertebral fixation frame.

8. The method of claim 7, wherein the step of excising bone material is performed entirely through the operating aperture in the secured vertebral fixation frame.

9. The method of claim 6, further comprising a step of installing an interbody implant retention member onto the secured vertebral fixation frame.

10. The method of claim 6, wherein the vertebral fixation frame is secured to more than two of the two or more adjacent vertebral bodies.

11. The method of claim 6, wherein the vertebral fixation frame is maintained in the originally secured position permanently.

\* \* \* \* \*